(12) United States Patent
Pesach et al.

(10) Patent No.: US 11,690,701 B2
(45) Date of Patent: Jul. 4, 2023

(54) INTRAORAL SCANNER

(71) Applicant: Dentlytec G.P.L. LTD., Tel-Aviv (IL)

(72) Inventors: Benny Pesach, Rosh Haayin (IL); Amitai Reuvenny, Kfar-Saba (IL)

(73) Assignee: DENTLYTEC G.P.L. LTD., Tel-Aviv (IL)

( * ) Notice: Subject to any disclaimer, the term of this patent is extended or adjusted under 35 U.S.C. 154(b) by 0 days.

(21) Appl. No.: 16/634,152

(22) PCT Filed: Jul. 24, 2018

(86) PCT No.: PCT/IL2018/050825
§ 371 (c)(1),
(2) Date: Jan. 26, 2020

(87) PCT Pub. No.: WO2019/021285
PCT Pub. Date: Jan. 31, 2019

(65) Prior Publication Data
US 2020/0205942 A1 Jul. 2, 2020

Related U.S. Application Data

(60) Provisional application No. 62/537,340, filed on Jul. 26, 2017.

(51) Int. Cl.
A61C 9/00 (2006.01)
A61C 7/00 (2006.01)
(Continued)

(52) U.S. Cl.
CPC .............. A61C 9/006 (2013.01); A61C 7/002 (2013.01); A61C 9/0066 (2013.01);
(Continued)

(58) Field of Classification Search
CPC ..... A61C 9/0053; A61C 9/006; A61C 9/0066; A61C 7/002; A61C 13/0004;
(Continued)

(56) References Cited

U.S. PATENT DOCUMENTS 3,634,938 A 1/1972 Hutchinson
4,279,598 A 7/1981 Scheicher
(Continued)

FOREIGN PATENT DOCUMENTS

CN 101677757 A 3/2010
EP 1901033 A1 3/2008
(Continued)

OTHER PUBLICATIONS

Applicant-Initiated Interview Summary dated Aug. 2, 2017 From the US Patent and Trademark Office Re. U.S. Appl. No. 15/115,196. (3 pages).
(Continued)

Primary Examiner — Vincent Rudolph
Assistant Examiner — Timothy Choi
(74) Attorney, Agent, or Firm — Cooley LLP

(57) ABSTRACT

A method of scanning an oral cavity including: acquiring, using an intraoral scanner (IOS) head, without changing a position of the IOS head, a first image of a first region of interest (ROI) and a second image of a second ROI where the first and the second ROIs are of different portions of a dental arch of the oral cavity and do not overlap; reconstructing depth information for the first and the second ROI; and generating a single model of the dental arch by combing the depth information.

20 Claims, 39 Drawing Sheets

(51) Int. Cl.
*G06T 19/20* (2011.01)
*G01B 11/25* (2006.01)
*A61C 13/00* (2006.01)
*G06V 20/64* (2022.01)

(52) U.S. Cl.
CPC ...... *A61C 13/0004* (2013.01); *G01B 11/2518* (2013.01); *G06T 19/20* (2013.01); *G06V 20/653* (2022.01); *G06T 2207/30036* (2013.01); *G06T 2219/2004* (2013.01)

(58) Field of Classification Search
CPC ........... G06K 9/00208; G06K 9/00214; G06K 9/2036; G06K 9/2054; G06K 9/2027; G06K 2009/2045; G06K 9/228; G06T 19/20; G06T 2219/2004
See application file for complete search history.

(56) References Cited

U.S. PATENT DOCUMENTS

| | | | |
|---|---|---|---|
| 4,478,580 A | 10/1984 | Barrut | |
| 4,571,180 A | 2/1986 | Kulick | |
| 4,665,621 A | 5/1987 | Ackerman et al. | |
| 4,764,114 A | 8/1988 | Jeffcoat et al. | |
| 4,790,751 A | 12/1988 | Reinhardt et al. | |
| 4,823,809 A | 4/1989 | Gott, Jr. et al. | |
| 4,873,651 A | 10/1989 | Raviv | |
| 4,883,425 A | 11/1989 | Zimble | |
| 4,935,635 A | 6/1990 | O'Harra | |
| 5,049,070 A | 9/1991 | Ademovic | |
| 5,051,823 A | 9/1991 | Cooper et al. | |
| 5,176,687 A | 1/1993 | Hasson et al. | |
| 5,178,536 A | 1/1993 | Werly et al. | |
| 5,178,537 A | 1/1993 | Currie | |
| 5,215,521 A | 6/1993 | Cochran et al. | |
| 5,224,049 A | 6/1993 | Mushabac | |
| 5,230,621 A | 7/1993 | Jacoby | |
| 5,244,387 A | 9/1993 | Fuierer | |
| 5,257,184 A | 10/1993 | Mushabac | |
| 5,313,053 A | 5/1994 | Koenck et al. | |
| 5,318,442 A | 6/1994 | Jeffcoat et al. | |
| 5,320,462 A | 6/1994 | Johansson et al. | |
| 5,368,597 A | 11/1994 | Pagedas | |
| 5,372,502 A | 12/1994 | Massen et al. | |
| 5,423,677 A | 6/1995 | Brattesani | |
| 5,435,722 A | 7/1995 | Mandell | |
| 5,618,296 A | 4/1997 | Sorensen et al. | |
| 5,634,790 A | 6/1997 | Pathmanabhan et al. | |
| 5,743,731 A | 4/1998 | Lares et al. | |
| 5,850,289 A | 12/1998 | Fowler et al. | |
| 5,862,559 A | 1/1999 | Hunter | |
| 5,897,509 A | 4/1999 | Toda et al. | |
| 5,919,129 A | 7/1999 | Vandre | |
| 5,944,523 A | 8/1999 | Badoz | |
| 5,969,321 A | 10/1999 | Danielson et al. | |
| 5,993,209 A | 11/1999 | Matoba et al. | |
| 6,000,939 A | 12/1999 | Ray et al. | |
| 6,007,333 A | 12/1999 | Callan et al. | |
| 6,116,899 A | 6/2000 | Takeuchi | |
| 6,142,936 A | 11/2000 | Beane et al. | |
| 6,179,611 B1 | 1/2001 | Everett et al. | |
| 6,257,889 B1 | 7/2001 | Boston | |
| 6,276,934 B1 | 8/2001 | Rakocz | |
| 6,309,219 B1 | 10/2001 | Robert | |
| 6,406,440 B1 | 6/2002 | Stefanchik | |
| 6,468,079 B1 | 10/2002 | Fischer et al. | |
| 6,819,318 B1* | 11/2004 | Geng .................. | G06T 17/00 345/420 |
| 6,885,464 B1 | 4/2005 | Pfeiffer et al. | |
| 7,041,056 B2 | 5/2006 | Deslauriers et al. | |
| 7,056,329 B2 | 6/2006 | Kerr | |
| 7,346,417 B2 | 3/2008 | Lueth et al. | |
| 7,494,338 B2 | 2/2009 | Durbin et al. | |
| 7,625,335 B2 | 12/2009 | Deichmann et al. | |
| 7,668,583 B2 | 2/2010 | Fegert et al. | |
| 7,813,591 B2 | 10/2010 | Paley et al. | |
| 8,280,152 B2 | 10/2012 | Thiel et al. | |
| 8,371,848 B2 | 2/2013 | Okawa et al. | |
| 8,439,682 B1 | 5/2013 | Heath et al. | |
| 8,744,194 B2 | 6/2014 | Kawasaki et al. | |
| 8,936,470 B2 | 1/2015 | Pruckner et al. | |
| 9,137,511 B1* | 9/2015 | LeGrand, III ........ | G06T 19/006 |
| 9,179,987 B2 | 11/2015 | Goodacre | |
| 9,463,081 B2 | 10/2016 | Urakabe | |
| 9,522,054 B2 | 12/2016 | Kim et al. | |
| 9,603,675 B2 | 3/2017 | Pruckner | |
| 9,918,805 B2 | 3/2018 | Pruckner | |
| 10,136,970 B2 | 11/2018 | Pesach | |
| 10,299,880 B2 | 5/2019 | Ramirez Luna et al. | |
| 10,470,846 B2 | 11/2019 | Kopelman et al. | |
| 10,695,150 B2 | 6/2020 | Kopelman et al. | |
| 2002/0037490 A1 | 3/2002 | Oyamada et al. | |
| 2002/0103420 A1* | 8/2002 | Coleman ............. | A61B 1/00087 600/173 |
| 2002/0133096 A1 | 9/2002 | Toda et al. | |
| 2004/0041996 A1* | 3/2004 | Abe ......................... | G01C 3/08 356/3.01 |
| 2004/0087937 A1 | 5/2004 | Eggers et al. | |
| 2004/0097792 A1 | 5/2004 | Moll et al. | |
| 2004/0106868 A1 | 6/2004 | Liew et al. | |
| 2004/0117052 A1 | 6/2004 | Geng | |
| 2004/0158261 A1 | 8/2004 | Vu | |
| 2004/0191725 A1 | 9/2004 | Szymaitis | |
| 2005/0116673 A1 | 6/2005 | Carl et al. | |
| 2006/0085005 A1 | 4/2006 | Kenealy, III et al. | |
| 2006/0154198 A1 | 7/2006 | Durbin et al. | |
| 2007/0037125 A1 | 2/2007 | Maev et al. | |
| 2007/0042315 A1 | 2/2007 | Boutoussov et al. | |
| 2007/0064242 A1 | 3/2007 | Childers | |
| 2007/0065782 A1 | 3/2007 | Maschke | |
| 2007/0172112 A1 | 7/2007 | Paley et al. | |
| 2007/0225744 A1 | 9/2007 | Nobles et al. | |
| 2007/0260231 A1 | 11/2007 | Rose et al. | |
| 2008/0002011 A1 | 1/2008 | Mizutani et al. | |
| 2008/0002869 A1 | 1/2008 | Scharlack et al. | |
| 2008/0038688 A1 | 2/2008 | Kopelman et al. | |
| 2008/0145817 A1 | 6/2008 | Brennan et al. | |
| 2008/0160477 A1 | 7/2008 | Stookey et al. | |
| 2008/0201101 A1 | 8/2008 | Hebert et al. | |
| 2008/0255498 A1 | 8/2008 | Houle | |
| 2008/0261165 A1 | 10/2008 | Steingart et al. | |
| 2009/0017416 A1 | 1/2009 | Nguyen et al. | |
| 2009/0043314 A1 | 2/2009 | Sevensson et al. | |
| 2009/0061383 A1 | 3/2009 | Kang | |
| 2009/0087050 A1 | 4/2009 | Gandyra | |
| 2009/0306506 A1 | 12/2009 | Heger et al. | |
| 2009/0326383 A1 | 12/2009 | Barnes et al. | |
| 2010/0047733 A1 | 2/2010 | Nahlieli | |
| 2010/0092908 A1 | 4/2010 | Rothenwaender et al. | |
| 2010/0189341 A1 | 7/2010 | Oota et al. | |
| 2010/0238279 A1 | 9/2010 | Thoms et al. | |
| 2010/0239136 A1* | 9/2010 | Gandyra ............ | G01B 11/2513 382/128 |
| 2010/0239996 A1 | 9/2010 | Ertl | |
| 2010/0268069 A1 | 10/2010 | Liang | |
| 2010/0268071 A1 | 10/2010 | Kim | |
| 2010/0303341 A1* | 12/2010 | Hausler .............. | G01B 11/2513 382/154 |
| 2010/0305435 A1 | 12/2010 | Magill | |
| 2011/0190781 A1 | 8/2011 | Collier et al. | |
| 2011/0301419 A1 | 12/2011 | Craft et al. | |
| 2012/0015329 A1 | 1/2012 | Gross et al. | |
| 2012/0040305 A1 | 2/2012 | Karazivan et al. | |
| 2012/0046536 A1 | 2/2012 | Cheung et al. | |
| 2012/0062557 A1 | 3/2012 | Dillon et al. | |
| 2012/0097002 A1 | 4/2012 | Thiedig | |
| 2012/0179281 A1 | 7/2012 | Steingart et al. | |
| 2012/0189182 A1 | 7/2012 | Liang et al. | |
| 2012/0270177 A1 | 10/2012 | Nakashima et al. | |
| 2012/0271176 A1 | 10/2012 | Moghaddam et al. | |
| 2013/0000666 A1 | 1/2013 | Hu | |
| 2013/0017507 A1 | 1/2013 | Moffson et al. | |
| 2013/0027515 A1 | 1/2013 | Vinther et al. | |

(56) References Cited

U.S. PATENT DOCUMENTS

| | | |
|---|---|---|
| 2013/0188012 A1 | 7/2013 | Bellis et al. |
| 2013/0209953 A1 | 8/2013 | Arlinsky et al. |
| 2013/0253278 A1 | 9/2013 | Smith |
| 2013/0273492 A1 | 10/2013 | Suttin, Sr. et al. |
| 2014/0066784 A1 | 3/2014 | Yokota |
| 2014/0093835 A1 | 4/2014 | Levin |
| 2014/0111616 A1 | 4/2014 | Blayvas |
| 2014/0120492 A1 | 5/2014 | Ioannidis et al. |
| 2014/0120493 A1 | 5/2014 | Levin |
| 2014/0146142 A1* | 5/2014 | Duret ............... A61B 5/065 348/46 |
| 2014/0178832 A1 | 6/2014 | Choi et al. |
| 2014/0194696 A1 | 7/2014 | Fischvogt |
| 2014/0199650 A1 | 7/2014 | Moffson et al. |
| 2014/0221819 A1 | 8/2014 | Sarment |
| 2014/0276055 A1 | 8/2014 | Barthe et al. |
| 2014/0248577 A1 | 9/2014 | Tahmasebi et al. |
| 2014/0309523 A1 | 10/2014 | Daon et al. |
| 2014/0330285 A1 | 11/2014 | Rosenblatt et al. |
| 2014/0343395 A1 | 11/2014 | Choi et al. |
| 2015/0015701 A1* | 1/2015 | Yu ............... G01B 11/2513 348/136 |
| 2015/0118638 A1 | 4/2015 | Cowburn |
| 2015/0182299 A1 | 7/2015 | Koubi et al. |
| 2015/0223910 A1 | 8/2015 | Pruckner |
| 2015/0223916 A1 | 8/2015 | Kim et al. |
| 2015/0229911 A1* | 8/2015 | Ge ............... H04N 13/239 348/47 |
| 2015/0297254 A1 | 10/2015 | Sullivan et al. |
| 2015/0348320 A1 | 12/2015 | Pesach et al. |
| 2016/0120615 A1 | 5/2016 | Scurtescu |
| 2016/0163115 A1 | 6/2016 | Furst |
| 2016/0259515 A1 | 9/2016 | Sabina et al. |
| 2016/0262856 A1 | 9/2016 | Atiya et al. |
| 2016/0270878 A1 | 9/2016 | Fulton, III |
| 2016/0338682 A1 | 11/2016 | Hoyte et al. |
| 2016/0338803 A1 | 11/2016 | Pesach |
| 2017/0007377 A1 | 1/2017 | Pesach et al. |
| 2017/0202483 A1 | 7/2017 | Sorimoto et al. |
| 2018/0318051 A1* | 11/2018 | Lu ............... G06V 10/44 |
| 2018/0360481 A1 | 12/2018 | Bonadio et al. |
| 2019/0125297 A1 | 5/2019 | Chan et al. |
| 2019/0192262 A1 | 6/2019 | Pesach |
| 2019/0247033 A1 | 8/2019 | Yaari |
| 2019/0343598 A1 | 11/2019 | Knobel et al. |
| 2020/0060550 A1 | 2/2020 | Pesach et al. |
| 2020/0268410 A1 | 8/2020 | Yaari et al. |
| 2022/0071737 A1 | 3/2022 | Pesach et al. |
| 2022/0151756 A1 | 5/2022 | Peasch et al. |

FOREIGN PATENT DOCUMENTS

| | | |
|---|---|---|
| EP | 2 165 674 A1 | 3/2010 |
| EP | 2630929 B1 | 8/2013 |
| ES | 2115544 A1 | 6/1998 |
| FR | 2692773 A1 | 12/1993 |
| GB | 2495522 A1 | 3/2013 |
| JP | 63-005742 A | 1/1988 |
| JP | 07-155297 A | 6/1995 |
| JP | 10-165425 A | 6/1998 |
| JP | H10-262996 A | 10/1998 |
| JP | 11-192207 A | 7/1999 |
| JP | 2003-325451 A | 11/2003 |
| JP | 2006-102497 A | 4/2006 |
| JP | 2007-152004 A | 6/2007 |
| JP | 2007-296249 A | 11/2007 |
| JP | 2009-268614 A | 11/2009 |
| JP | 2010-104652 A | 5/2010 |
| JP | 2012-016573 A | 1/2012 |
| JP | 5016311 B1 | 6/2012 |
| JP | 5016311 B2 | 9/2012 |
| JP | 2014-236957 A | 12/2014 |
| JP | 5661255 A | 1/2015 |
| KR | 10 1782740 B1 | 9/2017 |
| KR | 10-1782740 B1 | 9/2017 |
| WO | WO 98/06352 A1 | 2/1998 |
| WO | WO 2005/104959 A1 | 11/2005 |
| WO | WO 2007/063980 A1 | 5/2007 |
| WO | WO 2007/063980 A1 | 6/2007 |
| WO | WO 2008/013181 A1 | 1/2008 |
| WO | WO 2014/020247 A1 | 2/2014 |
| WO | WO 2014/102779 A2 | 7/2014 |
| WO | WO 2015/028646 A1 | 3/2015 |
| WO | WO 2015/107520 A1 | 7/2015 |
| WO | WO 2016/028789 A2 | 2/2016 |
| WO | WO 2016/064617 A1 | 4/2016 |
| WO | WO 2016/110855 A1 | 7/2016 |
| WO | WO 2016/113745 A1 | 7/2016 |
| WO | WO 2016/178212 A1 | 11/2016 |
| WO | WO 2017/125926 A2 | 7/2017 |
| WO | WO 2017/216803 A1 | 12/2017 |
| WO | WO 2018/047180 A1 | 8/2018 |
| WO | WO 2019/008586 A1 | 1/2019 |
| WO | WO 2019/021285 A1 | 1/2019 |
| WO | WO 2019/049152 A1 | 3/2019 |
| WO | WO 2020/144692 A2 | 7/2020 |

OTHER PUBLICATIONS

Communication Pursuant to Article 94(3) EPC dated Aug. 10, 2017 From the European Patent Office Re. Application No. 13830124.7. (6 Pages).

Communication Pursuant to Article 94(3) EPC dated Nov. 19, 2018 From the European Patent Office Re. Application No. 13830124.7. (8 Pages).

Communication Relating to the Results of the Partial International Search and the Provisional Opinion dated Jun. 14, 2017 From the International Searching Authority Re. Application No. PCT/IL2017/050072. (12 Pages).

Communication Relating to the Results of the Partial International Search dated May 8, 2014 From the International Searching Authority Re. Application No. PCT/IL2013/051059.

European Search Report and the European Search Opinion dated Feb. 4, 2020 From the European Patent Office Re. Application 19211372.8. (10 Pages).

International Preliminary Report on Patentability dated Aug. 2, 2018 From the International Bureau of WIPO Re. Application No. PCT/IL2017/050072. (10 Pages).

International Preliminary Report on Patentability dated Feb. 6, 2020 From the International Bureau of WIPO Re. Application No. PCT/IL2018/050825. (10 Pages).

International Preliminary Report on Patentability dated Jul. 9, 2015 From the International Bureau of WIPO Re. Application No. PCT/IL2013/051059.

International Preliminary Report on Patentability dated Jan. 16, 2020 From the International Bureau of WIPO Re. Application No. PCT/IL2018/050731. (9 Pages).

International Preliminary Report on Patentability dated Nov. 16, 2017 From the International Bureau of WIPO Re. Application No. PCT/IL2016/050449. (11 Pages).

International Preliminary Report on Patentability dated Jul. 20, 2017 From the International Bureau of WIPO Re. Application No. PCT/IL2016/050023. (10 Pages).

International Preliminary Report on Patentability dated Jul. 27, 2017 From the International Bureau of WIPO Re. Application No. PCT/IL2016/050058. (7 Pages).

International Search Report and the Written Opinion dated Oct. 1, 2018 From the International Searching Authority Re. Application No. PCT/IL2018/050731. (16 Pages).

International Search Report and the Written Opinion dated Sep. 2, 2014 From the International Searching Authority Re. Application No. PCT/IL2013/051059. (22 Pages).

International Search Report and the Written Opinion dated Aug. 8, 2017 From the International Searching Authority Re. Application No. PCT/IL2017/050072. (17 Pages).

International Search Report and the Written Opinion dated Apr. 18, 2016 From the International Searching Authority Re. Application No. PCT/IL2016/050058.

(56) References Cited

OTHER PUBLICATIONS

International Search Report and the Written Opinion dated Apr. 21, 2016 From the International Searching Authority Re. Application No. PCT/IL2016/050023.
International Search Report and the Written Opinion dated Aug. 23, 2016 From the International Searching Authority Re. Application No. PCT/IL2016/050449.
Notice Of Allowance dated Aug. 9, 2018 From the US Patent and Trademark Office Re. U.S. Appl. No. 15/571,231. (17 pages).
Notice Of Allowance dated May 12, 2016 From the US Patent and Trademark Office Re. U.S. Appl. No. 14/655,286.
Notice of Reasons for Rejection dated May 7, 2019 From the Japan Patent Office Re. Application No. 2017-228103 and Its Translation Into English. (8 Pages).
Notice of Reasons for Rejection dated Jul. 11, 2017 From the Japan Patent Office Re. Application No. 2015-548888 and Its Translation Into English. (5 Pages).
Notice of Reasons for Rejection dated Feb. 14, 2017 From the Japan Patent Office Re. Application No. 2015-548888 and Its Translation Into English. (10 Pages).
Notice of Reasons for Rejection dated Sep. 25, 2018 From the Japan Patent Office Re. Application No. 2017-228103 and Its Translation Into English. (15 Pages).
Notice Requesting Submission of Opinion dated Jan. 21, 2020 From the Korean Intellectual Property Office Re. Application No. 10-2019-7034814. (3 Pages).
Notice Requesting Submission of Opinion dated Apr. 26, 2019 From the Korean Intellectual Property Office Re. Application No. 10-2015-7020305. (4 Pages).
Notification of Office Action and Search Report dated Jan. 5, 2017 From the State Intellectual Property Office ofthe People's Republic of China Re. Application No. 201380071840.0. (7 Pages).
Notification of Office Action dated Apr. 15, 2016 From the State Intellectual Property Office of the People's Republic of China Re. Application No. 201380071840.0.
Office Action dated Aug. 6, 2019 From the Israel Patent Office Re. Application No. 264237 and Its Translation Into English. (6 Pages).
Official Action dated Mar. 9, 2017 From the US Patent and Trademark Office Re. U.S. Appl. No. 15/115,196. (26 pages).
Official Action dated Dec. 13, 2017 From the US Patent and Trademark Office Re. U.S. Appl. No. 15/115,196.(26 pages).
Official Action dated Jun. 13, 2019 From the US Patent and Trademark Office Re. U.S. Appl. No. 15/274,756. (39 pages).
Official Action dated Sep. 28, 2016 From the US Patent and Trademark Office Re. U.S. Appl. No. 15/115,196. (19 pages).
Requisition by the Examiner Dated Oct. 4, 2019 From the Innovation, Science and Economic Development Canada, Canadian Intellectual Property Office Re. Application No. 2,896,210. (3 Pages).
Restriction Official Action dated Nov. 14, 2019 From the US Patent and Trademark Office Re. U.S. Appl. No. 16/199,954. (6 pages).
Restriction Official Action dated Sep. 26, 2018 From the US Patent and Trademark Office Re. U.S. Appl. No. 15/274,756. (10 pages).
Supplementary European Search Report and the European Search Opinion dated Aug. 21, 2018 From the European Patent Office Re. Application No. 16789407.0. (6 Pages).
Translation Dated Feb. 2, 2020 of Notice Requesting Submission of Opinion dated Jan. 21, 2020 From the Korean Intellectual Property Office Re. Application No. 10-2019-7034814. (3 Pages).
Translation Dated May 9, 2019 of Notice Requesting Submission of Opinion Dated Apr. 26, 2019 From the Korean Intellectual Property Office Re. Application No. 10-2015-7020305. (4 Pages).
Translation of Notification of Apr. 15, 2016 From the State Intellectual Property Office of the People's Republic of China Re. Application No. 201380071840.0. (2 pages).
Translation of Notification of Office Action dated Jan. 5, 2017 From the State Intellectual Property Office of the People's Republic of China Re. Application No. 201380071840.0. (4 Pages).
Bouget et al. "3D Photography Using Shadows in Dual-Space Geometry", The International Journal of Computer Vision, 35(2): 129-149, Nov./Dec. 1999.

Fluegge et al. "Precision of Intraoral Digital Dental Impressions With iTero and Extraoral Digitization With the iTero and A Model Scanner", American Journal of Orthodontics and Dentofacial Orthopedics, 144(3): 471-478, Sep. 2013.
Geng "Structured-Light 3D Surface Imaging: A Tutorial", Advances in Optics and Photonics, 3:128-160, 2011.
Goshtasby et al. "A System for Digital Reconstruction of Gypsum Dental Casts", IEEE Transactions On Medical Imaging, 16(5): Oct. 1997.
Logozzo et al. "Recent Advances in Dental Optics—Part I: 3D Intraoral Scanners for Restorative Dentistry", Optics and Lasers in Engineering, 54: 203-221, Mar. 2014.
Maintz et al. "A Survey of Medical Image Registration", Medical Image Analysis, 2(1): 1-36, Mar. 1998.
Medeiros et al. "Coded Structred Light for 3D-Photography: An Overview", IEEE-RITA, (Latin-American Learning Technologies Journal), IV(2): 109-124, Jul. 1999.
OmniVision "OVM6946 400x400. Compact, Cost-Effective Wafer-Level Camera Module for Single-Use Endoscopes", OmniVision, Product Brief, 2 P., Aug. 10, 2016.
Paperno et al. "A New Method for Magnetic Position and Orientation Tracking", IEEE Transactions on Magnetics, XP011033696, 37(4): 1938-1940, Jul. 2001.
Salvi et al. "Pattern Codification Strategies in Structured Light Systems", Pattern Recognition, 37(4): 827-849, 2004.
Savarese et al. "3D Reconstruction by Shadow Carving: Theory and Practical Evaluation", International Journal of Computer Vision, 71(3): 305-336, Published Online Jun. 1, 2006.
Toshiba "IK-CT2: 0.7 x 0.7 mm, 220x220, CMOS", Toshiba Information Systems, Product Sheet, 1 P., Dec. 2016.
International Search Report and Written Opinion dated Nov. 7, 2018 for International Application No. PCT/IL2018/050825, 15 pages.
Official Action dated Apr. 3, 2020 from the US Patent and Trademark Office Re. U.S. Appl. No. 16/199,954. (31 pages).
International Search Report and the Written Opinion dated Nov. 7, 2018 From the International Searching Authority Re. Application No. PCT/IL2018/050825. (17 Pages).
Official Action dated May 15, 2020 from the US Patent and Trademark Office Re. U.S. Appl. No. 16/071,058. (31 pages).
Invitation to Pay Additional Fees Dated May 12, 2020 From the International Searching Authority Re. Application No. PCT/IL2020/050040. (3 Pages).
International Search Report and the Written Opinion dated Jul. 23, 2020 From the International Searching Authority Re. Application No. PCT/IL2020/050040. (14 Pages).
Official Action dated Feb. 19, 2021 From the US Patent and Trademark Office Re. U.S. Appl. No. 16/227,995. (27 Pages).
Notice Requesting Submission of Opinion dated Feb. 3, 2021 From the Korean Intellectual Property Office Re. Application No. 10-2020-7032325 and Its Translation Into English. (14 Pages).
Communication Pursuant to Article 94(3) EPC dated Nov. 19, 2020 From the European Patent Office Re. Application No. 13830124.7. (6 Pages).
Official Action dated Nov. 4, 2020 From the US Patent and Trademark Office Re. U.S. Appl. No. 15/274,756. (19 Pages).
Notice of Allowance dated Jul. 13, 2021 from the US Patent and Trademark Office Re. U.S. Appl. No. 16/227,995. (7 pages).
Communication Pursuant to Article 94(3) EPC dated Oct. 5, 2021 From the European Patent Office Re. Application No. 18759184.7, (6 Pages).
Communication Pursuant to Article 94(3) EPC dated Oct. 7, 2020 From the European Patent Office Re. Application No. 177805300.6. (5 Pages).
Communication Pursuant to Article 94(3) EPC dated Nov. 16, 2021 From the European Patent Office Re. Application No. 17707964.7, (4 Pages).
Communication Pursuant to Article 94(3) EPC dated Jan. 29, 2021 From the European Patent Office Re. Application No. 18769813.9, (9 Pages).
Communication Pursuant to Article 94(3) EPC dated Nov. 30, 2021 From the European Patent Office Re. Application No. 17780530.6, (4 Pages).

(56) References Cited

OTHER PUBLICATIONS

Communication Pursuant to Article 94(3) EPC dated Jan. 31, 2020 From the European Patent Office Re. Application No. 17780530.6, (3 Pages).
English Translation Dated Nov. 30, 2021 of Ground(s) of Reason of Rejection dated Nov. 19, 2021 From the Korean Intellectual Property Office Re. Application No. 2010-7032325, (2 Pages).
European Search Report and the European Search Opinion dated Jan. 3, 2022 From the European Patent Office Re. Application No. 21200149.9, (10 Pages).
Ground(s) of Reason of Rejection dated Nov. 19, 2021 From the Korean Intellectual Property Office Re. Application No. 2010-7032325, (2 Pages).
International Preliminary Report on Patentability dated Mar. 19, 2020 From the International Bureau of WIPO Re. Application No. PCT/IL2017/051014. (10 Pages).
International Preliminary Report on Patentability dated Mar. 21, 2019 From the International Bureau of WIPO Re. Application No. PCT/IL2017/051015. (13 Pages).
International Preliminary Report on Patentability dated Jul. 22, 2021 From the International Bureau of WIPO Re. Application No. PCT/IL2020/050040. (10 Pages).
International Search Report and the Written Opinion dated Dec. 11, 2018 From the International Searching Authority Re. Application No. PCT/IL2017/051014. (18 Pages).
International Search Report and the Written Opinion dated Jan. 24, 2018 From the International Searching Authority Re. Application No. PCT/IL2017/051015. (23 Pages).
Invitation to Pay Additional Fees, Communication Relating to the Results of the Partial International Search and the Provisional Opinion dated Nov. 17, 2017 From the International Searching Authority Re. Application No. PCT/IL2017/051015. (17 Pages).
Restriction Official Action dated May 25, 2022 From the US Patent and Trademark Office Re. U.S. Appl. No. 16/628,656, (7 Pages).
Summons to Attend Oral Proceedings Pursuant to Rule 115(1) EPC Dated Mar. 18, 2022 From the European Patent Office Re. Application No. 18769813.9. (9 Pages).
Summons to Attend Oral Proceedings Pursuant to Rule 115(1) EPC Dated Mar. 19, 2021 From the European Patent Office Re. Application No. 17780530.6. (7 Pages).
Summons to Attend Oral Proceedings Pursuant to Rule 115(1) EPC Dated Apr. 20, 2021 From the European Patent Office Re. Application No. 17780530.6, (2 Pages).
Supplementary European Search Report and the European Search Opinion dated Feb. 19, 2021 From the European Patent Office Re. Application No. 18837606.5, (7 Pages).
Translation Dated Nov. 30, 2021 of Ground(s) of Reason of Rejection dated Nov. 19, 2021 From the Korean Intellectual Property Office Re. Application No. 2010-7032325, (2 Pages).
Communication Pursuant to Article 94(3) EPC dated Jul. 1, 2022 From the European Patent Office Re. Application No. 18837606.5, (4 Pages).
Official Action dated Aug. 11, 2022 from US Patent and Trademark Office Re. U.S. Appl. No. 16/628,656, (36 pages).
Supplementary European Search Report and the European Search Opinion dated Aug. 24, 2022 From the European Patent Office Re. Application No. 20739036.0. (9 Pages).
Official Action dated Oct. 26, 2022 from the US Patent and Trademark Office Re. U.S. Appl. No. 16/634,152. (15 pages).
Final Official Action dated Nov. 9, 2021 from US Patent and Trademark Office Re. U.S. Appl. No. 15/274,756. (15 pages).
Notice of Allowance dated Nov. 9, 2022 from the US Patent and Trademark Office Re. U.S. Appl. No. 15/274,756. (8 pages).
Official Action dated Jun. 17, 2021 from the US Patent and Trademark Office Re. U.S. Appl. No. 15/274,756. (16 pages).
Official Action dated Jul. 20, 2022 from US Patent and Trademark Office Re. U.S. Appl. No. 15/274,756. (25 pages).
Requisition by the Examiner Dated Apr. 7, 2021From the Innovation, Science and Economic Development Canada, Canadian Intellectual Property Office Re. Application No. 2,896,210. (16 Pages).
Supplementary European Search Report and the European Search Opinion dated Feb. 2, 2023 from the European Patent Office for Application No. 22207979.0, (7 Pages).

* cited by examiner

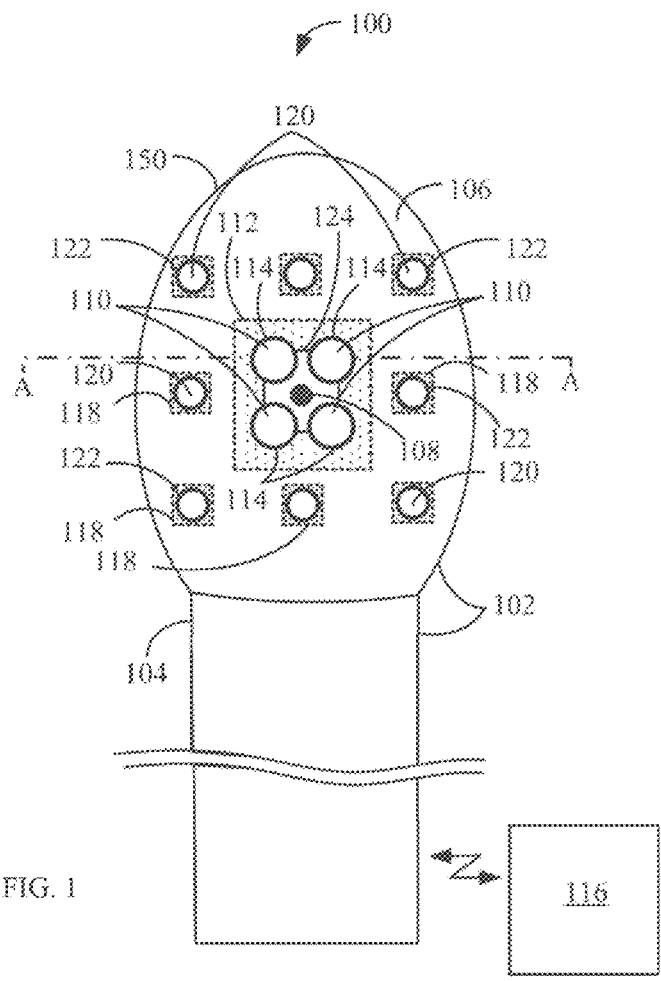
FIG. 1
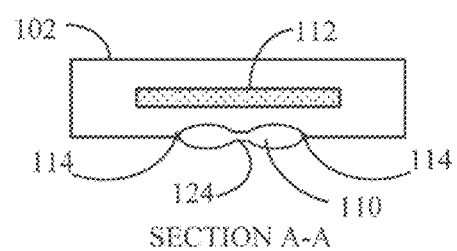
SECTION A-A

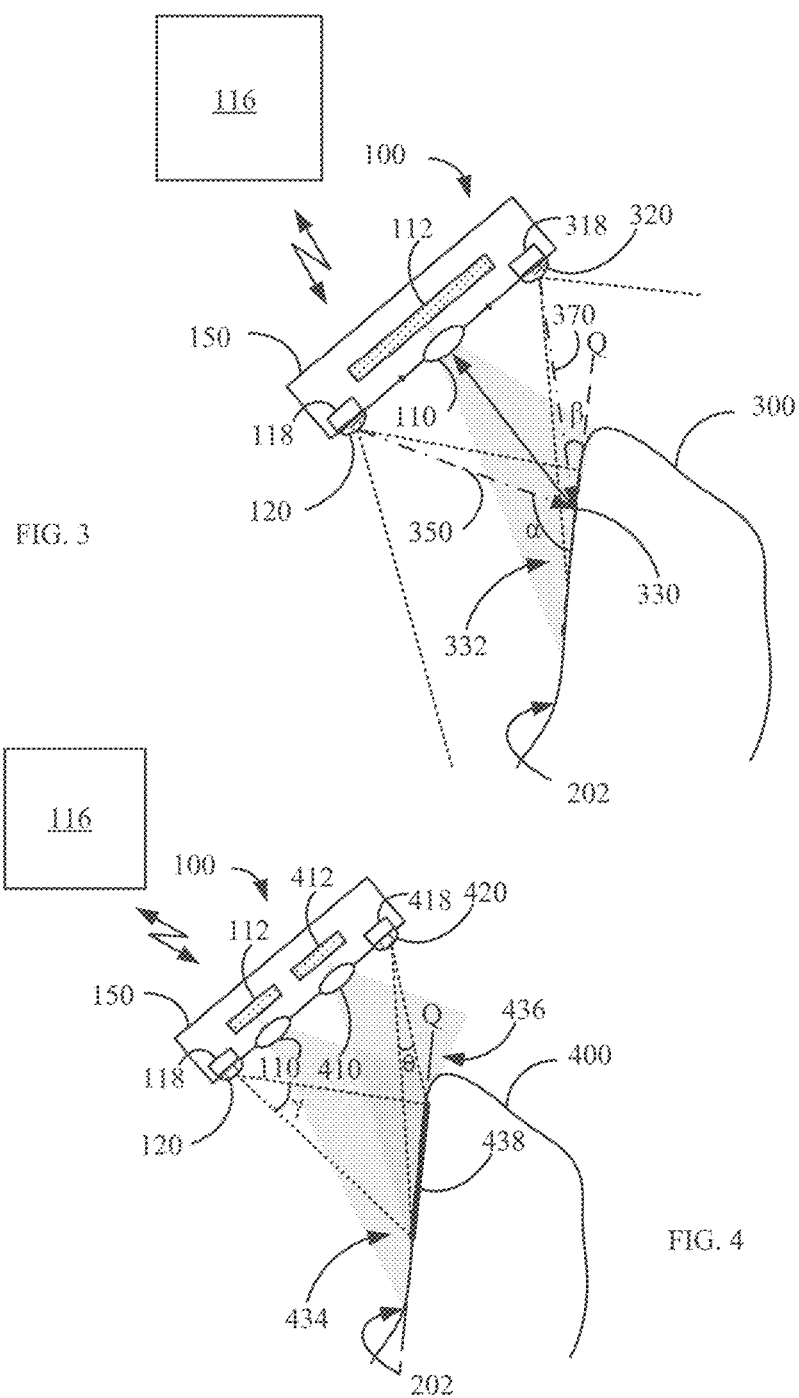

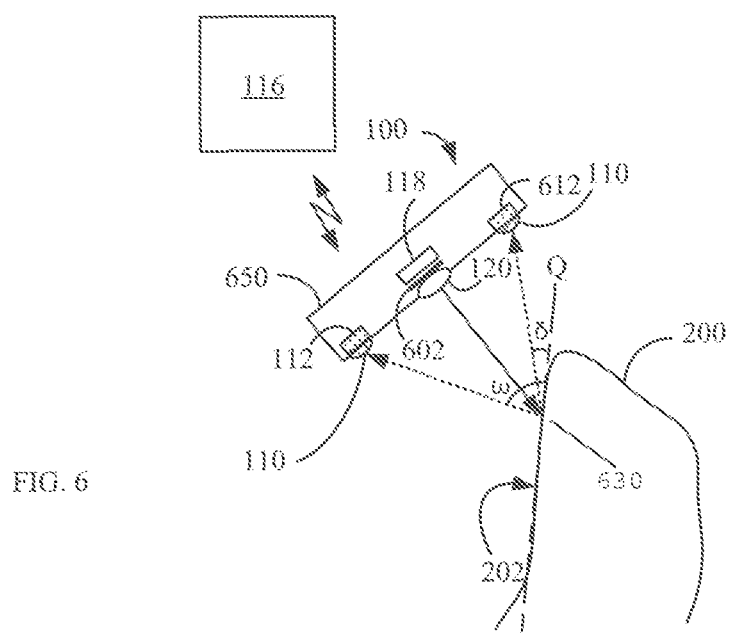
FIG. 6
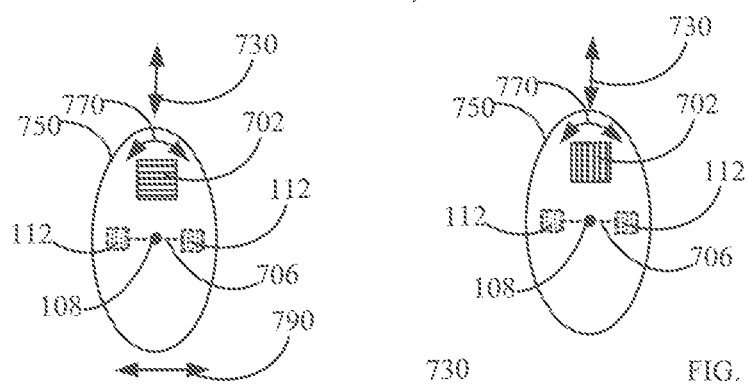
FIG. 7A
FIG. 7B
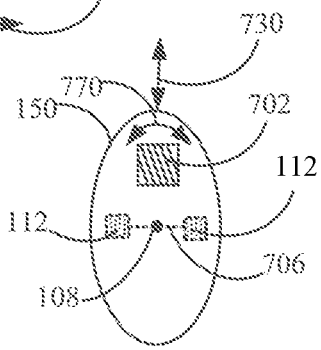
FIG. 7C

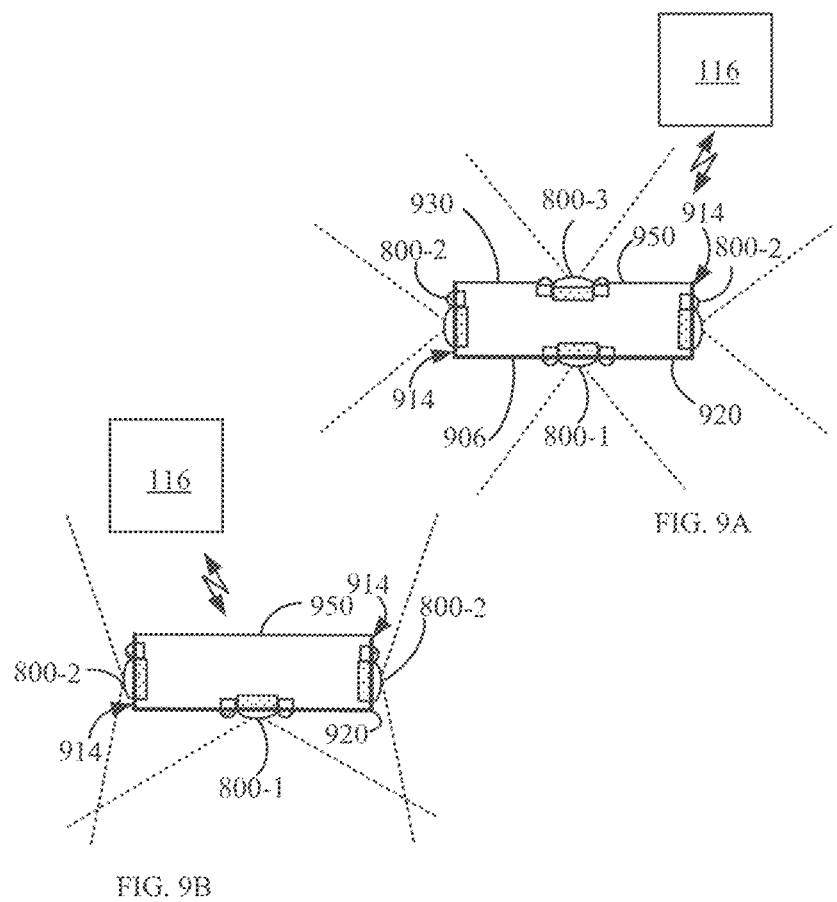
FIG. 9A
FIG. 9B
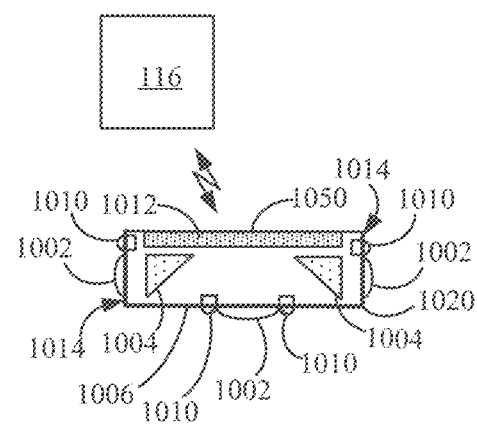
FIG. 10

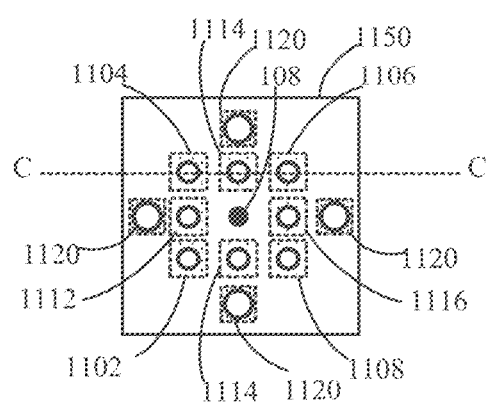
FIG. 11
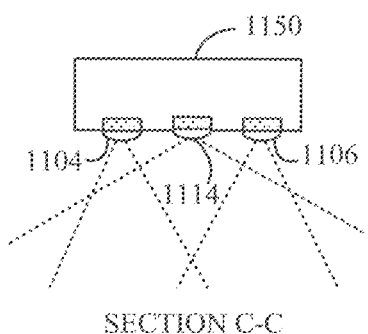
SECTION C-C
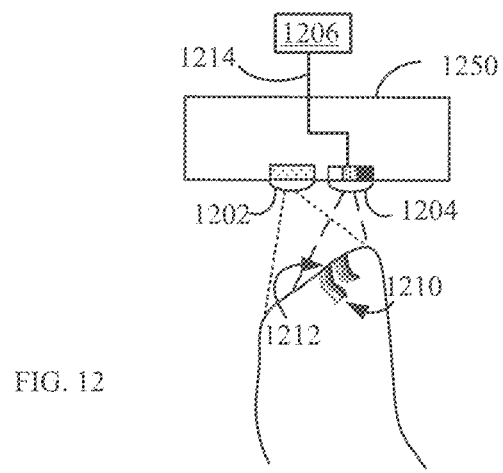
FIG. 12

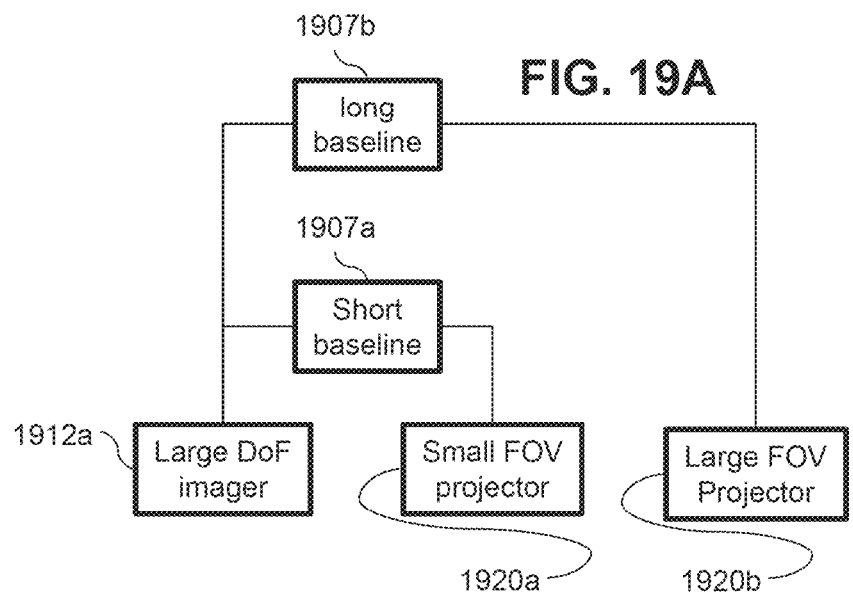
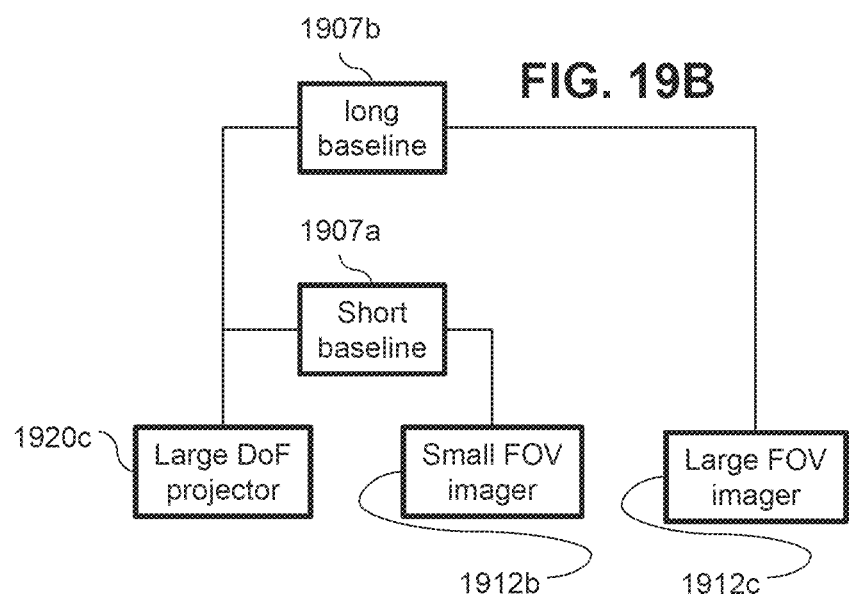

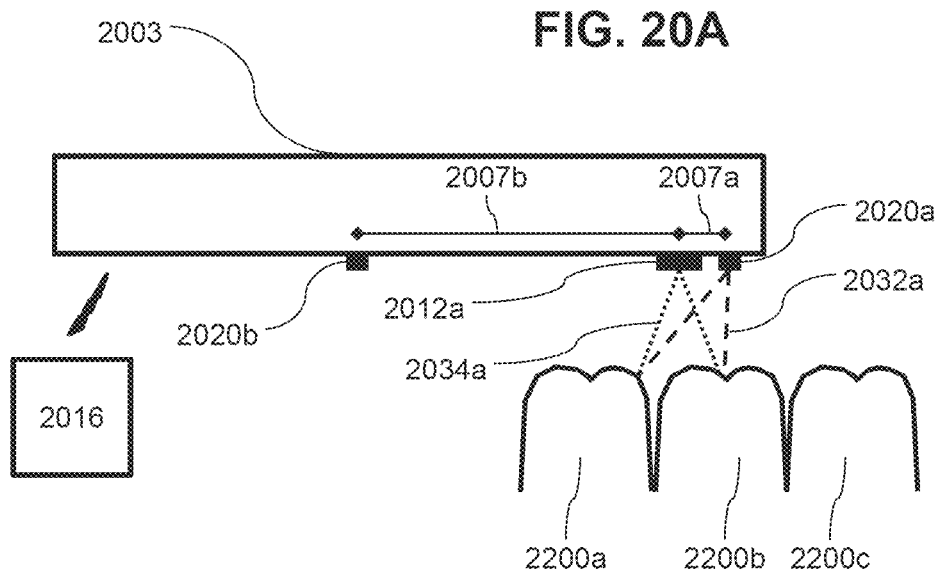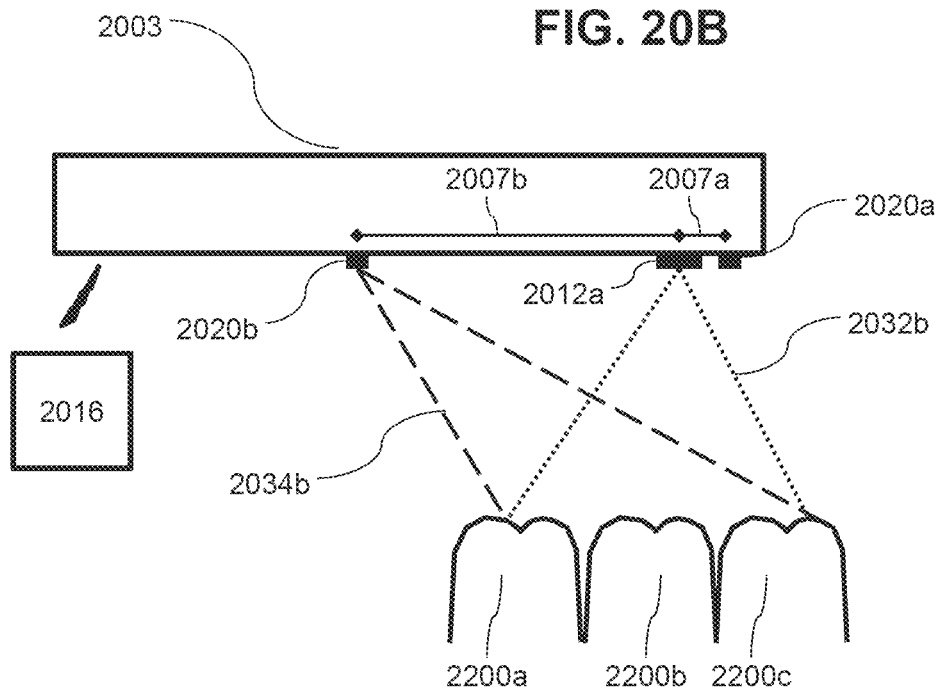

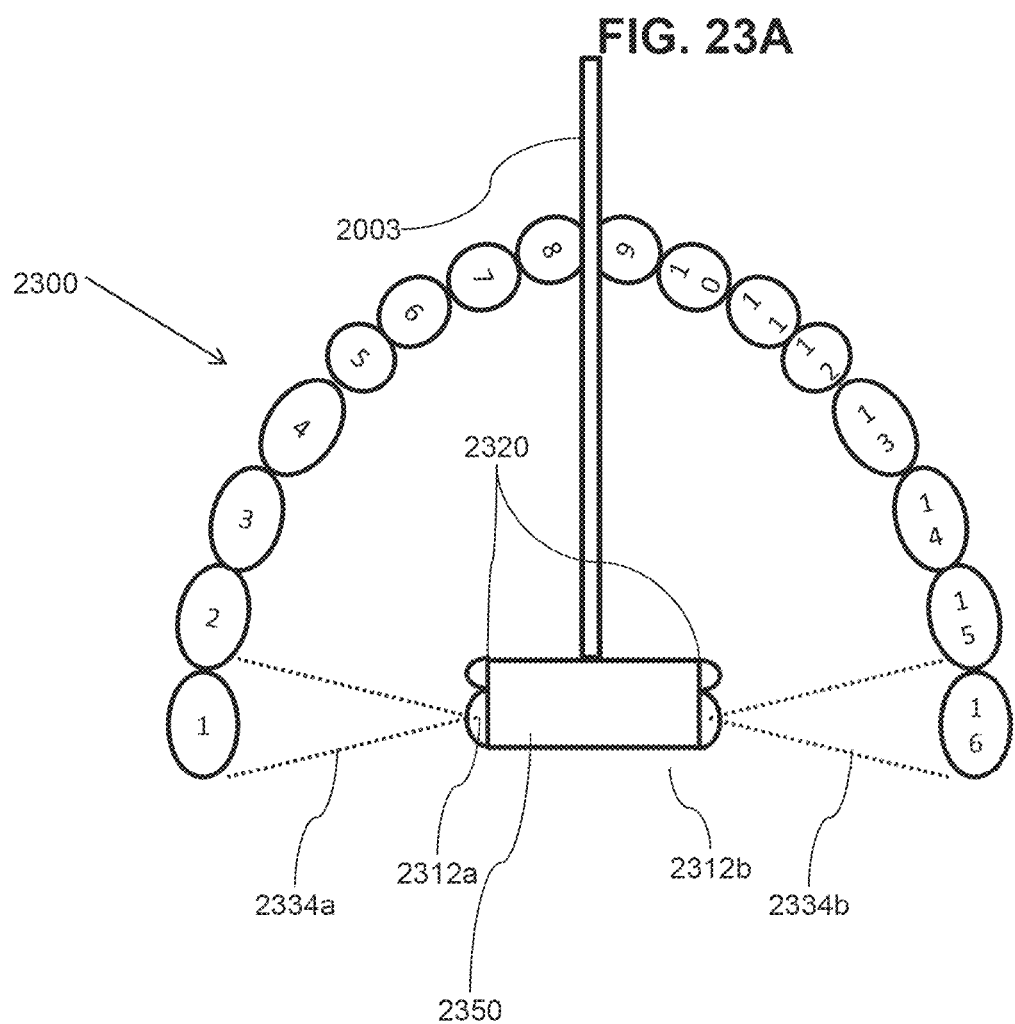

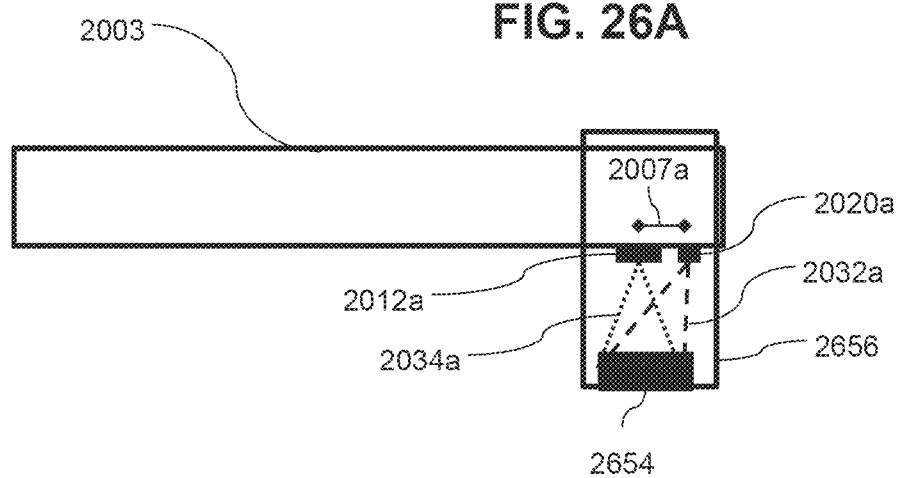
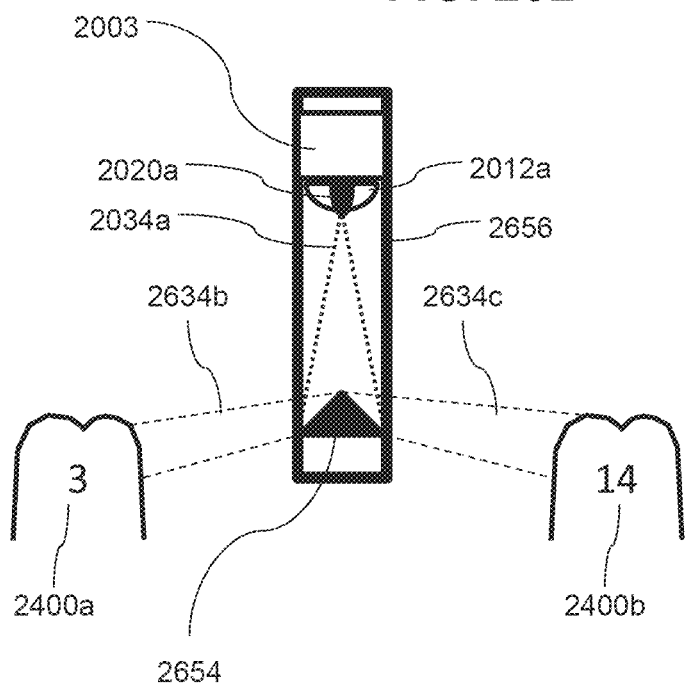

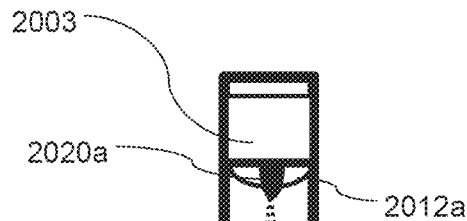
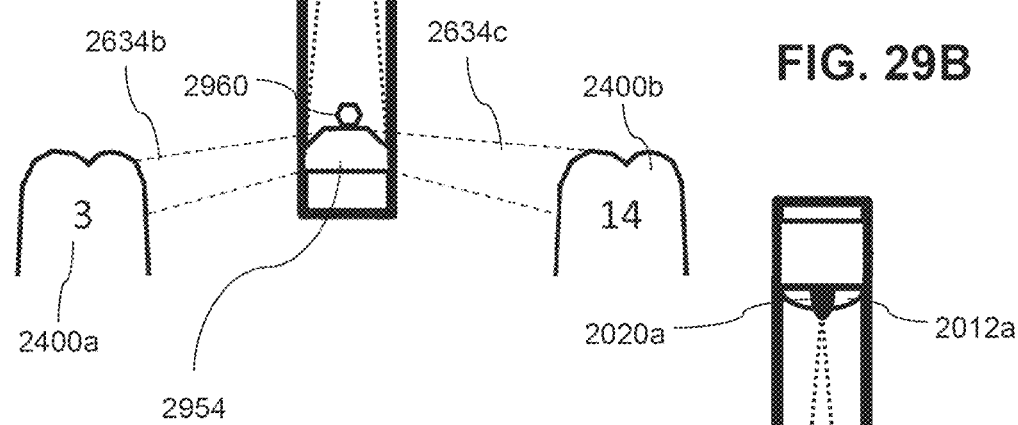
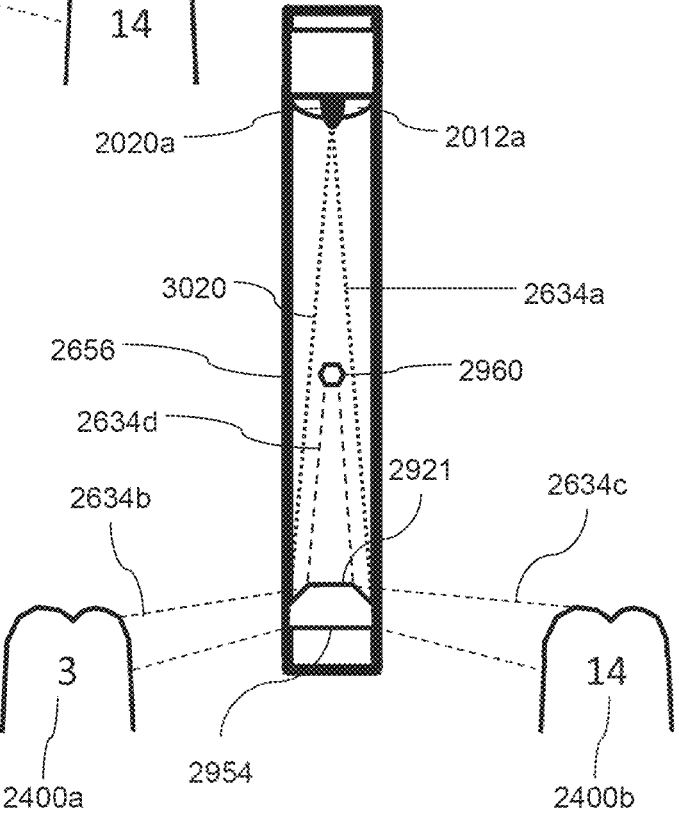
FIG. 29A
FIG. 29B

INTRAORAL SCANNER

This application claims the benefit of priority under 35 USC § 119(e) of U.S. Provisional Patent Application No. 62/537,340 filed 26 Jul. 2017, the contents of which is incorporated herein by reference in its entirety.

This application is also related to PCT Patent Application No. PCT/IL2016/050058, titled "SYSTEM, DEVICE, AND METHOD FOR DENTAL INTRAORAL SCANNING" filed on Jan. 18, 2016, which claims the benefit of priority under 35 USC § 119(e) of U.S. Provisional Patent Application No. 62/104,835, filed on Jan. 18, 2015.

This application is also related to: Provisional Patent Application No. 62/364,681, filed on Jul. 4, 2017; Provisional Patent Application No. 62/528,496, filed on Jul. 20, 2016; U.S. Pat. No. 9,204,804; U.S. Patent publication No. 2010-0189341; U.S. Pat. No. 8,971,999; and "Application of Intra-Oral Dental Scanners in the Digital Workflow of Implantology", by Wicher J. van der Meer1*, Frank S. Andriessen2, Daniel Wismeijer3, Yijin Ren4.

FIELD AND BACKGROUND OF THE DISCLOSURE

The present disclosure, in some embodiments thereof, relates to a dental scanner for example, an intra oral scanner (IOS) and more particularly but not exclusively to use of an IOS to produce accurate large scale maps.

The contents of the above applications and article are all incorporated by reference as if fully set forth herein in their entirety.

The use of intraoral scanners (IOS) to size and acquire a 3D image of a tooth or teeth requiring restoration (e.g., for prostheses or model preparation) has become prevalent in dentist practices. However, commonly used IOSs combine the use of image sensors, light emitters, several lenses, mirrors, reflectors, beam splitters and other components the size and quantity of which contribute to a relatively large form factor and bulkiness of the IOS.

SUMMARY OF SOME EMBODIMENTS OF THE DISCLOSURE

According to an aspect of some embodiments of the disclosure, there is provided a method of scanning an oral cavity comprising: acquiring, using an intraoral scanner (IOS) head, without changing a position of said IOS head, a first image of a first region of interest (ROI) and a second image of a second ROI where said first and said second ROIs are of different portions of a dental arch of the oral cavity and do not overlap; reconstructing depth information for said first and said second ROI; and generating a single model of said dental arch by combining said depth information.

According to some embodiments of the disclosure, the acquiring of said first image and said second image is simultaneous.

According to some embodiments of the disclosure, the first ROI is captured by a first IOS field of view (FOV) and said second ROI is captured by a second IOS FOV.

According to some embodiments of the disclosure, the IOS includes at least two imagers where said first FOV is of a first imager and where said second FOV is of a second imager.

According to some embodiments of the disclosure, the IOS includes at least one imager and a splitter which splits an FOV of said at least one imager into said first and second FOVs. According to some embodiments of the disclosure, the splitter is part of an attachment connected to said IOS.

According to some embodiments of the disclosure, the dental arch lacks one or more tooth. According to some embodiments of the disclosure, the splitter comprises one or more mirror. According to some embodiments of the disclosure, the dental arch includes one or more tooth abutment.

According to some embodiments of the disclosure, the first ROI is of a first side of said dental arch and said second ROI is of a second side of said dental arch.

According to some embodiments of the disclosure, the method comprises changing said position of said IOS and repeating said acquiring, said reconstructing and said generating.

According to an aspect of some embodiments of the disclosure, there is provided a method of scanning an oral cavity including: introducing an intraoral scanner (IOS) head into an oral cavity; acquiring an image of a region of interest (ROI); determining a representative distance to the acquired ROI; selecting a baseline length according to the representative distance and imaging the region using two optical modules separated by the selected baseline length.

According to some embodiments of the disclosure, the selecting comprises selecting said two optical modules from a plurality of IOS optical modules. According to some embodiments of the disclosure, the selecting comprises moving one of both of said two optical modules.

According to some embodiments of the disclosure, the selecting a baseline length includes selecting a longer baseline length as the distance to the ROI increase.

According to some embodiments of the disclosure, the IOS includes multiple projectors and at least one imager. The baseline is a distance between an imager and a projector and the selecting includes selecting a projector distanced from the imager by the baseline length. The imaging is with the selected projector and the imager.

According to an aspect of some embodiments of the disclosure, there is provided a method of scanning an oral cavity including: imaging a first ROI using a scanner in a first location; imaging a second ROI at least 1 cm from the first ROI while the scanner is positioned within 0.1 mm of the first location; and determining a spatial relation between a feature in the first ROI and a feature in the second ROI. Determining is independent of the position of features between the first ROI and the second ROI.

According to some embodiments of the disclosure, the imaging the first ROI and the imaging the second ROI are performed simultaneously. Simultaneously being defined as at the same time or nearly at the same time e.g. within 1 second or within 1 millisecond, or within 1 microsecond or within a time such that camera shake of a person holding the camera does not cause image smear.

According to some embodiments of the disclosure, the imaging the first ROI and the imaging the second ROI are performed within a time period of less than a frame rate of an imager.

According to some embodiments of the disclosure, the imaging the first ROI and the imaging the second ROI are performed within a time period of less than 1 second.

According to some embodiments of the disclosure, the determining is to a specific accuracy.

According to some embodiments of the disclosure, the determining is to an accuracy of within 150% of a representative accuracy of relative location of two points within the first ROI.

According to some embodiments of the disclosure, the determining is without forming an image of an area connect the first ROI and the second ROI.

According to an aspect of some embodiments of the disclosure, there is provided a method of scanning an oral cavity composing: acquiring an image of a ROI in the oral cavity using a first imager on an IOS the first imager having a frame period; acquiring a second image of a feature in the oral cavity using a second imager on the IOS, the acquiring a second image within a time lag of more than $1/100$ of the frame period and less than the $3/4$ of the frame period.

According to some embodiments of the disclosure, the time lag is less than an integration period of the first imager.

According to some embodiments of the disclosure, the time lag is greater than an integration period of the first imager.

According to some embodiments of the disclosure, the feature is in the ROI.

According to some embodiments of the disclosure, the second imager has an integration period less than the first imager and further including determining a position of the IOS in the oral cavity based on the second image.

According to an aspect of some embodiments of the disclosure, there is provided an IOS including: an imager; a plurality of pattern projectors including a first pattern projector distanced from the imager by a first baseline length and a second pattern projector distanced from the imager by a second baseline length greater than the first baseline length; a processor configured to determine a working distance of a ROI from the imager, and select a pattern projector from the plurality of pattern projectors based on the working distance.

According to some embodiments of the disclosure, a FOV of the imager overlaps the a FOV of the first projector at a first working distance from the imager and a FOV of the imager overlaps a FOV of the second projector at a second working distance greater than the first working distance.

According to an aspect of some embodiments of the disclosure, there is provided a method of imaging an oral cavity including: acquiring a plurality of small scale images with an IOS scanner; stitching together the plurality of small scale images to form a large scale 3D model; acquiring with the IOS a correction image including two features distanced by a scale greater than a maximum breadth of any of the plurality of small images; determining a relative position of the two features from the correction image; adjusting a position of a feature in the large scale 3D model based on the relative position.

According to some embodiments of the disclosure, acquiring the correction image includes imaging two disconnected subfields.

According to some embodiments of the disclosure, the method further includes attaching an FOV splitter to the IOS.

According to some embodiments of the disclosure, the method further includes calibrating the FOV splitter.

According to some embodiments of the disclosure, the calibrating includes making an image of an external precalibrated object.

According to some embodiments of the disclosure, the correction image includes a calibration subfield, and calibrating is dependent on the calibration subfield.

According to an aspect of some embodiments of the disclosure, there is provided a method for intraoral scanning, including: introducing an intraoral scanner (IOS) head into an oral cavity; acquiring an image of a region of interest (ROI); processing the acquired ROI image; and adjusting at least one image acquisition parameter other than exposure based on the processing.

According to some embodiments of the disclosure, the acquisition parameter includes a spatial orientation of the IOS head in respect to a region of interest (ROI).

According to some embodiments of the disclosure, the IOS includes at least a first light projector producing a first light beam, and the processing includes also estimation of an angle of incidence the first light beam on a surface of the ROI and where the adjusting is based on the estimated angle of incidence.

According to some embodiments of the disclosure, the acquisition parameter includes a direction and/or a rate of IOS head movement.

According to some embodiments of the disclosure, the processing includes analyzing at least one image property of the acquired image and determining adjustment of the at least one image acquisition parameter based on the at least one image and, the adjustment includes at least one of: selecting and/or activating at least one imager, selecting and/or activating at least one light projector, deselecting and/or deactivating at least one imager, and deselecting and/or deactivating at least one light projector or combination thereof.

According to some embodiments of the disclosure, the adjustment includes signaling user to change spatial orientation of the IOS head.

According to some embodiments of the disclosure, the IOS head includes at least one imager and at least one light projector, and the acquisition parameter includes at least one of: at least one projected light parameter, a focal length of at least one IOS imager, a size of a field of view FOV of a sensor on the ROI, and a distance between at least one of one point of interest POI in the ROI and the imager, the POI and a light projector, and the imager and the light projector.

According to some embodiments of the disclosure, the IOS includes a first light projector and a second light projector and the adjustment.

According to some embodiments of the disclosure, the processing includes also estimation of an angle of incidence of a first beam of the first light projector over the ROI and estimation of an angle of incidence of a second beam of the second light projector over the ROI.

According to some embodiments of the disclosure, the estimated angle of incidence of the first beam is greater than the estimated angle of incidence of the second beam.

According to some embodiments of the disclosure, the processing includes tooth segmentation and locating the ROI on the segmented tooth and the adjustment is based on the segmentation.

According to some embodiments of the disclosure, the IOS includes an elongated element coupled to a first surface of the IOS, the first surface facing a region of interest (ROI), the method further including: contacting a location on the ROI with a portion of the elongated element, and the adjustment includes selecting at least one image acquisition parameter producing an image from which a position of the location can be determined more accurately that a previous parameter.

According to some embodiments of the disclosure, the adjustment includes activating a light emitter to illuminate a third surface of the elongated element, the third surface generally opposite the portion of the elongated element that contacts the ROI.

According to some embodiments of the disclosure, the location is under a gum line.

According to some embodiments of the disclosure, adjustment also includes selecting an imager oriented with the third surface generally facing the selected imager and located between the selected imager and the ROI.

According to some embodiments of the disclosure, the method further includes casting a structured light pattern on the ROI, and adjusting the pattern based on the processing.

According to some embodiments of the disclosure, the processing includes also estimation of a contrast of the structure light over the ROI and the adjusting is controlled by the processor to improve the contrast.

According to some embodiments of the disclosure, the processor estimates a movement of the IOS and the adjusting is based on at least one of the movement and a predicted future spatial relationship between the IOS head and a region of interest.

According to some embodiments of the disclosure, the adjusting is based on a current or estimated future spatial relationship between the IOS and the ROI.

According to some embodiments of the disclosure, the spatial relationship includes at least one of a location and an orientation.

According to some embodiments of the disclosure, the method further includes projecting a patterned light onto the ROI and correlating a pattern of the patterned light with the spatial relationship.

According to an aspect of some embodiments of the disclosure, there is provided an intraoral scanner (IOS) including: an IOS head including at least one imager imaging a field of view (FOV); at least one light projector configured for illuminating the FOV; and circuitry configured for at least one of processing an image acquired by the imager and adjusting at least one image acquisition parameter other than exposure based on the processing.

According to some embodiments of the disclosure, the IOS includes multiple optical components having multiple apertures and the multiple optical components include the at least one imager and the one light projector.

According to some embodiments of the disclosure, the adjusting is achieved without moving parts.

According to some embodiments of the disclosure, the IOS head has a width of less than 3 cm and is mounted on a distal portion of a handle of length between 10 to 40 cm.

According to some embodiments of the disclosure, the IOS head has a longitudinal axis at an angle of between 85 to 60 degrees of a proximal portion of the handle.

According to some embodiments of the disclosure, the IOS head includes a probe at having a distal portion thereof at an angle of between 85 to 60 degrees to a proximal portion of the handle.

According to some embodiments of the disclosure, the IOS head includes a probe and a plurality of imagers and a plurality of light projectors located around the probe.

According to some embodiments of the disclosure, the acquisition parameter includes at least one of: spatial orientation of the IOS head in respect to a region of interest (ROI), direction and rate of IOS head movement, focal length of IOS imager, a size of the FOV, a distance between at least one of the ROI and the imager, the ROI and a light projector, and the imager and the light projector.

According to some embodiments of the disclosure, the at least one light parameter includes at least one of: a number of light projectors, a light intensity, a projected structured light pattern, light coherence, wavelength, duration of light, pulsed light, continuous light, pulse frequency and structured light pattern, a power level of the projector, a flicker time of the projector.

According to some embodiments of the disclosure, the IOS head includes at least one optical transmitter/receiver wafer level optics (WLO) module which includes the imager and light projector.

According to an aspect of some embodiments of the disclosure, there is provided an intraoral scanner (IOS) including: one or more imagers and one or more light projectors, some imagers and projectors formed on one or more interconnected boards at least one of the imagers having a first optical aperture and having different external dimensions from at least one of the light projectors, the at least one light projector having a second optical aperture; and the first optical aperture and the second optical aperture are located on a plane perpendicular to a mean line of sight of the at least one imager and the at least one light projector.

According to some embodiments of the disclosure, the one or more interconnected boards includes at least one of a staggered rigid PCB, a planar PCB, and a flexible PCB.

According to some embodiments of the disclosure, the IOS further includes a plurality of imaging apertures for imaging by one or more imagers. At least two of the plurality of apertures is configured for imaging at different focal distances.

According to some embodiments of the disclosure, the plurality of imaging apertures are all located on the plane perpendicular to the mean line of sight.

According to an aspect of some embodiments of the disclosure, there is provided an intraoral scanner (IOS) including: a multi-layered WLO module including a top layer including at least one imager and at least one light projector; and a second layer including at least one structured light transparency device.

According to some embodiments of the disclosure, the IOS further includes a bottom layer including at least one microlens positioned along an optical path of at least of the light projector and the imager.

According to some embodiments of the disclosure, at least two of the layers are separated by a spacer frame.

According to some embodiments of the disclosure, the spacer frame includes an optical module including at least one of a condensing element and a diffusing element.

According to some embodiments of the disclosure, the bottom layer is configured as a glass molded array or polymer lenses on a glass wafer.

According to some embodiments of the disclosure, the bottom layer further includes at least one projection microlens including a pair of lenses disposed on both sides of the wafer.

According to some embodiments of the disclosure, the imager and the light projector face the bottom layer.

According to some embodiments of the disclosure, the top layer further includes a light projector spacer frame including PCB or Si wafer with at least one mounted light projector.

According to some embodiments of the disclosure, the layers also include a mid-layer glass wafer having a clear portion corresponding to an image receiving area of the imager.

According to some embodiments of the disclosure, the clear portion is coated with a filtering coat.

According to some embodiments of the disclosure, the IOS head includes: a first surface facing a first region of interest, a second surface and a third surface, each attached to the first surface on opposite sides thereof and facing a second region of interest and a third region of interest, respectively, and at least one optic transmitters/receivers wafer level optics (WLO) module disposed on each of the surfaces.

According to some embodiments of the disclosure, the IOS head includes a first surface facing a first region of interest, a second surface and a third surface, each attached to the first surface on opposite sides thereof and facing a second region of interest and a third regions of interest, respectively, and at least one imaging lens disposed on each of the surfaces.

According to some embodiments of the disclosure, an image received by at least one lens disposed on the second and/or third surfaces is imaged on at least a portion of the imager via a mirror or a prism.

According to some embodiments of the disclosure, the light projector is a coherent light generator that generates a diffractive light pattern on an ROI, the light pattern including at least two different wavelengths.

According to an aspect of some embodiments of the disclosure, there is provided a method for intraoral scanning, including: positioning an intraoral scanner (IOS) head inside an oral cavity; acquiring consecutive images of a region of interest (ROI); processing the acquired images; and predicting at least one future location and/or spatial orientation of the IOS head based on the processing.

According to some embodiments of the disclosure, the method further includes analyzing at least one image property of at least one of the acquired images and determining at least one future adjustment of at least one image acquisition parameter based on at least one of the image property and the prediction.

Unless otherwise defined, all technical and/or scientific terms used herein have the same meaning as commonly understood by one of ordinary skill in the art to which the disclosure pertains. Although methods and materials similar or equivalent to those described herein can be used in the practice or testing of embodiments of the disclosure, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present disclosure may be embodied as a system, method or computer program product.

Accordingly, some embodiments of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present disclosure may take the form of a computer program product embodied in one or more computer readable medium(s) having computer readable program code embodied thereon. Implementation of the method and/or system of some embodiments of the disclosure can involve performing and/or completing selected tasks manually, automatically, or a combination thereof. Moreover, according to actual instrumentation and equipment of some embodiments of the method and/or system of the disclosure, several selected tasks could be implemented by hardware, by software or by firmware and/or by a combination thereof, e.g., using an operating system.

For example, hardware for performing selected tasks according to some embodiments of the disclosure could be implemented as a chip or a circuit. As software, selected tasks according to some embodiments of the disclosure could be implemented as a plurality of software instructions being executed by a computer (which may simply be a processor) using any suitable operating system. In an exemplary embodiment of the disclosure, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the disclosure. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present disclosure may be described below with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which executed via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such acquiring an image employing an intraoral scanner, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

Some embodiments of the disclosure are herein described, by way of example only, with reference to the accompanying drawings. With specific reference now to the drawings in detail, it is stressed that the particulars shown are by way of example and for purposes of illustrative discussion of embodiments of the disclosure. In this regard, the description taken with the drawings makes apparent to those skilled in the art how embodiments of the disclosure may be practiced.

In the drawings:

FIG. 1 is a plan view and cross-section view thereof at level A-A simplified illustration of a surface of an intraoral scanner (IOS) facing a region of interest (ROI) in accordance with embodiments of the current disclosure;

FIG. 3 is a cross-section view simplified illustration of an example of implementation of scanner optics in accordance with embodiments of the current disclosure;

FIG. 4 is a cross-section view simplified illustration of an example of implementation of scanner optics;

FIG. 6 is a cross-section view simplified illustration of an example of implementation of scanner optics in accordance with embodiments of the current disclosure;

FIGS. 7A, 7B and 7C are plan view simplified illustration of an example of implementation of scanner optics in accordance with embodiments of the current disclosure;

FIGS. 9A and 9B are cross section view simplified illustrations of embodiments of an IOS head in accordance with embodiments of the current disclosure;

FIG. 10 is a cross section view simplified illustration of an embodiment of an IOS head in accordance with embodiments of the current disclosure;

FIG. 11 is a plan view and cross section view thereof at level C-C simplified illustration of an embodiment of an IOS head in accordance with embodiments of the current disclosure;

FIG. 12 is a cross-section view simplified illustration of an embodiment of an IOS head in accordance with embodiments of the current disclosure;

FIGS. 19A and 19B are block diagram illustrations of scanners with variable baseline optics in accordance with an embodiment of the current disclosure;

FIGS. 20A and 20B are schematic illustrations of use of a multiple FOV IOS in accordance with an embodiment of the current disclosure;

FIGS. 23A, 23B, 24 and 25 are schematic illustrations of an IOS configured to produce a compound FOV image in accordance with an embodiment of the current disclosure;

FIGS. 26A-B, 27A-C, 28, 29A-B, 30 and 31 are schematic illustrations of IOS's including an attachments for scanning a compound FOV in accordance with embodiments of the current disclosure;

DESCRIPTION OF SOME OF THE EMBODIMENTS OF THE DISCLOSURE

Overview

Figure 2A:
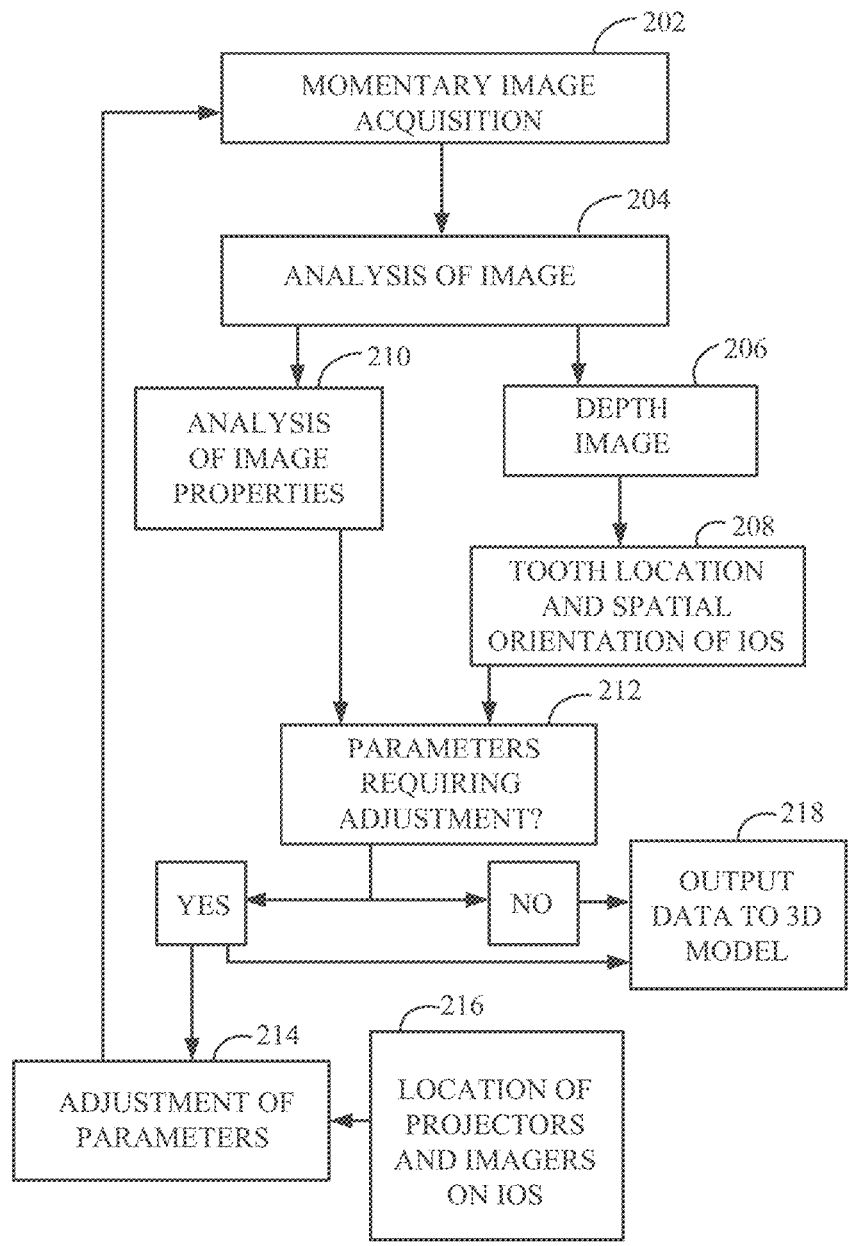
FIGS. 2A and 2B are flow charts of a processing operation of an image acquired by an IOS head in accordance with embodiments of the current disclosure.

The present disclosure, in some embodiments thereof, relates to a dental scanner for example an intra oral scanner (IOS) and more particularly but not exclusively to use of an IOS to produce accurate large scale 3D models.

In some embodiments, an IOS is designed for producing 3D depth mapped images at a small scale. For example, the small scale may include a surface that is smaller than a whole tooth and/or a surface of length less than 15 mm. A large scale 3D model, optionally includes 3D models which are significantly larger than the IOS small scale FOV (Field of View). For example, a large scale image may include multiple teeth and/or include a features between 15 to 30 mm and/or between 30 to 60 mm from each other. In some embodiments, the large FOV may include a compound FOV, for example including disconnected regions. For example, multiple imagers may image disconnected subfields that may be integrated into a single image where the spatial relationship between the subfields is known.

The present disclosure, in some embodiments thereof, relates to use of an IOS to make images including multiple scales and/or fields of view FOV. For example, the shape of the FOV and/or the baseline of the device may be selected to produce multiscale images. The multiscale images may be used to produce a 3D oral map accurately depicting special relationships at multiple scales.

In some exemplary applications, a dental scan may cover a large zone. For example, a scan may be used as a preparation for a procedure that concern a large zone, for example of 3 or more teeth or a space that remains from 3 or more teeth. For example, a prosthetic may be fit to multiple teeth and/or implants and/or space remaining from multiple teeth. For example, an orthodontic device may fit multiple teeth.

In some embodiments a 3D model will be made that includes a high spatial precision over a large scale. For example, the relative spatial precision error between locations in the model may be less than 30 μm and/or between 30 to 60 μm and/or between 60 to 100 μm. Small FOV detailed scans may achieve the desired precision over a collection of small FOVs covering the zone. A large FOV scan may be used to define spatial relationships between a pair of objects that are far apart (e.g. not both found in a single small FOV image). The precise spatial relationship between the far objects may be used to further refine other areas of the 3D model.

An aspect of some embodiments of the invention relates to generating a single model of at least a portion of a patient's mouth. For example, of a dental arch and/or of a portion of a dental arch. In some embodiments, a measurement is collected using an IOS, without moving and/or changing a position of the head. Where, in some embodiments, a first image of a first region of interest (ROI) and a second image of a second ROI are acquired, for example, using first and second imagers and/or imager-projector pairs. For example, using a single imager where the FOV of the imager is split. In some embodiments, the first and said second ROIs are of different portions of a dental arch of the oral cavity and, in some embodiments, the ROIs do not overlap. In some embodiments, depth information is reconstructed for the ROIs from which a single model of the mouth portion (e.g. dental arch) is generated. In some embodiments, the single model is a model including both depth information for both ROIs and a spatial relationship between the ROIs. Where, for example, the ROI depth information for both ROIs is in a shared coordinate system. In some embodiments, known data regarding the IOS FOVs (e.g. determined in calibration) is used to combine the depth information for the ROIs into a single model. In some embodiments, the IOS is moved one or more time, where measurements are performed at a plurality of positions e.g. to measure the full dental arch. In some embodiments, the model generated from the ROIs includes one or more gap, where the gap, in some embodiments, is filled using, for example, data from another source e.g. previously collected IOS data and/or CT scan data. In some embodiments, a user is alerted when the model includes a gap e.g. a user interface directing the user to portion/s of the dental arch which need to be scanned and/or re-scanned.

An aspect of some embodiments of the disclosure relates to an IOS including multiple optical modules of different working distance and/or overlapping and/or non-overlapping fields of view. Optionally processor activates and/or deactivates a module automatically based on the objects in the view. For example, when the device is imaging an object at a given distance, a module is selected for imaging at the desired precision at the imaging distance. For example, in some embodiments, a baseline between optical modules is selected to achieve a desired accuracy at a given scanning distance.

In some embodiments, baseline between optical elements may be selected to achieve a desired accuracy for a give FOV. For example, for a higher accuracy and/or at a longer distance from the imaged object, a larger baseline may be selected. An estimation of measurement accuracy is given by $\Delta d = z2 \times \Delta p/(EFL \times baseline)$. Wherein: Z is the distance; $\Delta p$ is the resolution in which the pattern location can be found in the image; EFL is the effective focal length of the imager lens; baseline is the distance between the 2 optical apertures (i.e. projector and imager or two imagers used for the depth calculation e.g. In accordance with the equation, in some cases a larger base line may be selected to improve depth accuracy when working at a larger distance. For example, when working at a distance of z=20 mm the baseline length may be increased by a factor of 4 over the baseline length for the same accuracy when working at a distance of 10 mm. For example, a device may include multiple imagers and/or pattern projectors. The baseline distance may be defined as the distance between the exit pupil of projector used for illumination and the exit pupil of an imager used for imaging. Optionally, the baseline can be defined also as the distance between the exit pupils of two imagers used as a passive or active stereo pair. A projector—imager pair or two imagers pairs are selected to achieve a desired depth accuracy. For example, a processor may track the distance to a scanned object. As the distance increases, the processor may select an imager-projector pair with a larger baseline. Alternatively or additionally, the processor may also select projector—imager pair whose overlapping FOV is optimal at the working distance. Alternatively or additionally, the processor may choose illumination power to illuminate at the working distance and/or an imager that focuses at the working distance and/or a projector that projects a properly focused image.

In some embodiments, the baseline of an IOS is changed, for example, by reflection of one or more IOS FOV (e.g. FOV of one or more imager and/or one or more projector). In some embodiments, baseline is increased by reflection at two reflective surfaces with different angles, where, for example, in some embodiments, an FOV of an imager and an FOV of a projector are reflected by surfaces with different angles. In some embodiments, the two reflective surfaces are part of an IOS attachment. A potential advantage of an enlarged baseline is increased accuracy of IOS measurements of distant objects, for example, when scanning teeth from different regions (e.g. opposite sides, different ends) of a dental arch.

An aspect of some embodiments of the current disclosure relates to an IOS having multiple FOVs. Optionally, a depth mapped image may be made of an object in each FOV. Additionally or alternatively, a spatial relationship may be determined between objects in different FOVs.

For example, a few teeth may be scanned together. Alternatively or additionally, a pair of teeth that are far apart may be scanned together in a larger FOV. For example, the large FOV scan may be used to measure far away objects with a level of error that is less than the cumulative error of a set small FOV images that are stitched together.

In some embodiments, the larger FOV may be not be non-continuous. For example, the FOV may include non-connected regions with a known relative position. For example, a FOV may include at least two subfields which include for example two sides of a dental arch. A compound image is optionally made of both subfields simultaneously.

For example, the relative positions of features in different subfields may be computed from the compound image. Optionally, the compound image may reduce the cumulative error of a composite image covering an area between the subfields. For example, a compound image of two ends of a dental arch may be used to reduce error in a model of the full dental arch (for example a mandibular arch and/or a maxillary arch) made by stitching small FOV images into a composite image, for example, stitching images may induce an accumulative the error in relative locations at far parts, for example opposites ends of a dental arch. Optionally, a more precise relative position of the ends of the arch may be computed from the compound image. The computed precise relative position of the ends of the arch may optionally be used to condition the measurements in the composite image made by stitching small FOV images. In some embodiments, the accurate large model results from the conditioning of the composite model. The accurate large model may be useful for example for bridges of few teeth and/or for modeling a full arch and/or for dentures for example for an edentulous mouth.

In some embodiments, a compound image may be made from at least two subfields. For example, the subfields may include images obtained using one imager module, projector module pair on one side of an IOS and a second imager module, projector module pair an opposite side of an IOS. Alternatively or additionally, the pairs of imager and projector modules may both be attached on a single side of an IOS. Alternatively or additionally, the subfields may be obtained by splitting the FOV of single imager and/or projector such that at least two FOVs find the depth of the two sides of an arch and reduce said accumulated error. For example, different regions of a single imager may be focused onto different subfields.

An aspect of some embodiments of the current disclosure relates to an attachment to an IOS that splits a FOV of an imager and/or into multiple FOVs. For example, the attachment may include a splitter that splits a single FOV into multiple subfields. For example, the attachment may facilitate making a compound image and/or large scale image using a conventional scanner that is configured to produce a small scale simple image. For example, the conventional scanner may be used in one scan to make a conventional high resolution stitched image of an area. A second scan may be made producing a large scale and/or a compound image from which large scale spatial relationships may be computed. The large and small scale images are optionally combined (for example by conditioning the stitched composite model on the large scale measurements).

In some embodiments, the attachment may include a calibration element. For example, a compound image may include two or more subfields and the calibration element. The image of the calibration element may be used to determine the position and/or orientation of the attachment with respect to the IOS. Alternatively or additionally, calibration may be performed an external aid, for example by using the IOS and attachment to measure a pre-calibrated space and/or a space including a fiducial object. Additionally or alternatively, a spatial relationship may be determined between objects in subfields of a compound FOV.

In some embodiments, a calibration element will include a diffuse reflector attached to a splitter. For example, the IOS imager may image the reflection of the IOS projector will on the diffuse reflector. This image is optionally used to determine the location and/or orientation of the splitter. Alternatively or additionally, the calibration element may include a fiducial object. In some embodiments, a folded path may be formed. For example, the folded path may be between an imager and the calibration element and/or between a projector and the calibration element. The folded path may make the focal distance to the calibration element similar to the focal distance to a FOV that is being measured.

An aspect of some embodiments of the current disclosure relates to a method of producing a 3D map of a composite region of an oral cavity. For example, a composite model may be made of a plurality of small FOV images. Large scale spatial relationships may be corrected based on a large scale image. Optionally the large scale image may include a compound image that includes small scale images of subfields from far away locations (optionally the subfields may not be spatially continuous) and/or a spatial relationship between the subfields. For example, the composite model may be conditioned on the large scale measurements.

Intraoral scanners (IOS) typically combine the use of several optical components, e.g., image sensors, light emitters, lenses, mirrors, reflectors, splitters and other components the size of which oftentimes contributes to a relatively large form factor and bulkiness of the IOS.

An aspect of some embodiments of the disclosure relates to a downscaled multi aperture optics intraoral scanner (IOS) head having a small form factor. In some embodiments of the disclosure, the IOS is in the form and size of a common dental turbine. In some embodiments, the IOS includes a head having an image sensor that defines an optical field of view and communicates a received image to a processing unit that processes received images into a 3D image. In some embodiments, the IOS includes an elongate element fixedly or movably coupled to a surface of the IOS facing a region of interest (ROI). In some embodiments, the elongated element may be angled in reference to the surface of the IOS facing a region of interest (ROI). In some embodiments, the elongated element may be generally normal to the surface of the IOS facing a region of interest (ROI). In some embodiments, the IOS head width may be between 5-25 mm. In some embodiments, the IOS head width may be between 3-20 mm. In some embodiments, the IOS head width may be between 1-15 mm. In some embodiments, the IOS head length may be between 3-20 cm. In some embodiments, the IOS head width may be between 5-25 mm. In some embodiments, the IOS head thickness may be between 10-20 mm. In some embodiments, the IOS head thickness may be between 5-15 mm. In some embodiments, the IOS head thickness may be between 3-10 mm.

In some embodiments, an IOS may have few or no moving parts. For example, the viewing adjustments may be without moving parts. For example, the optical portion of the IOS may contain no moving parts. For example, the IOS may have multiple optical apertures and/or changing a direction of illumination and/or a direction of viewing and/or a focal length and/or a field of view may be achieved by activating various devices associated with various optical apertures but without moving those devices with respect to the IOS and/or each other. Using multiple apertures optionally facilitates adjusting of optical parameters such as focal length and/or field of view with fewer and/or without moving parts. In some embodiments, a device having fewer and/or without moving parts may be smaller and/or more reliable than a device having more moving parts. In some embodiments, a device having fewer and/or no moving parts may be more easily controlled by a process, for example for automated control of optical parameters than a device with more moving parts. For example, control may be via simple transistors and/or switches without requiring, for example, position sensors.

In some embodiments, the elongated element is disposed in the face of the IOS. In some embodiments, the elongated element is disposed off-center of the face of the IOS. For example, the elongated element may be perpendicular to a surface facing a ROI. In some embodiments, the elongated element is shaped like a stylus. In some embodiments, the elongated element is telescopic and may vary in length. In some embodiments, the elongate element includes one or more of an image sensor, an imaging lens, a micro light emitter and a structured light transparency. In some embodiments, an elongated object may include a probe, for example a dental probe. Optionally the elongated object is straight. Alternatively or additionally, the elongated object may be bent, angled or curved. For example, the elongated object may be configured for probing locations under a gum line. Optionally a sensor is provided to sense when an elongated object is in contact with a ROI. Optionally, a processor is configured to compute and/or adjust viewing parameters to facilitate and/or increase accuracy of determination of a point of contact between the elongated object and the ROI based on an image and/or a set of images.

In some embodiments of the disclosure, the image sensor is disposed on a surface of the IOS facing a first region of interest (ROI). In some embodiments, the IOS includes more than one image sensor. In some embodiments, the image sensor includes an array of micro image sensors. In some embodiments, the image sensor is manufactured by wafer level optics technology (WLO). In some embodiments, the image sensor is between 0.1 mm and 150 mm. In some embodiments, the image sensor(s) cover(s) between 10 and 90 percent of the IOS head surface facing a first region of interest (ROI). In some embodiments, the image sensor/s cover(s) between 20 and 80 percent of the IOS head facing a first region of interest (ROI). In some embodiments, the image sensor(s) cover(s) between 30 and 70 percent of the IOS head facing a first region of interest (ROI).

In some embodiments of the disclosure, the scanner includes one or more imaging microlenses disposed between the image sensor and the ROI that project a received image onto the image sensor. In some embodiments, a single final microlens is disposed between the image sensor and the ROI. In some embodiments, several imaging microlenses project overlapping images on the image sensor. In some embodiments, several imaging microlenses project images on separate corresponding segments of the image sensor. In some embodiments, a single imaging microlens comprises several imaging microlens elements. In some embodiments, a single imaging microlens comprises an array of microlens elements. In some embodiments, the imaging microlens is manufactured by wafer level optics (WLO) technology. In some embodiments, each imaging microlens element projects an image on a portion of the image sensor. In some embodiments, the imaging microlenses are disposed inside apertures in the surface of the IOS. In some embodiments, the image sensor is disposed inside the IOS head, deeper than the apertures of the imaging microlenses.

In some embodiments, imaging microlens array is bonded to a single image sensor. In some embodiments, the microlens array is bonded to an array of image sensors. In some embodiments, the imaging microlens array is a glass molded array. In some embodiments, the imaging microlens array is made of polymer microlenses on a glass array. In some embodiments, the image sensor is produced on a silicon wafer. In some embodiments, an array of image sensors on a wafer is bonded to an L array of microlenses and diced together with the attached image lens array to produce individual bonded image sensor-micro lens modules. In some embodiments, the imaging lens is made of metamaterials.

In some embodiments, the IOS is mirrorless. In some embodiments all IOS components (i.e., image sensor, imaging lens, light emitter, projecting lens and structured light micro transparency) necessary to acquire a 3D image, for example, a computer 3D model is located in the head of the IOS. In some embodiments, every light ray incident on a single final imaging lens continues travel directly to the image sensor.

In some embodiments a processing unit digitally stitches (i.e., integrates or attaches) image segments received from the image sensor. In some embodiments, a processing unit optically stitches image segments received from the image sensor. In some embodiments, the processing unit processes image segments received from the image sensor without stitching. In some embodiments, the IOS includes circuitry that controls IOS components (e.g., micro light emitters, micro structured light emitters) based on received image information. In some embodiments, the IOS includes circuitry that controls IOS components (e.g., micro light emitters, micro structured light emitters) based on input from the processing unit. In some embodiments, acquired image segments of a single field of view (FOV) are projected on the image sensor. In some embodiments, each acquired segment includes a complete FOV. In some embodiments, the processing unit processes received image information in real time.

In some embodiments of the disclosure, the IOS includes one or more light emitters that project light in the general direction of the ROI. In some embodiments, the IOS includes a plurality of light emitters that project light in the general direction of the ROI. In some embodiments, a plurality of light emitters is generally distributed about the elongated element. In some embodiments, the IOS includes two light emitters each on either side of the elongated element. In some embodiments, a micro light emitter casts structured light on a tooth. In some embodiments, structured light is projected via projection microlenses. In some embodiments, the micro light emitter is independent of the IOS.

In some embodiments of the disclosure, the projection lenses are micro optic projection lens. In some embodiments, the projection microlenses are low modulation transfer function (MTF) microlenses. In some embodiments, the projection microlenses are disposed in an aperture. In some embodiments, the aperture is less than 2 mm in diameter. In some embodiments, the aperture is less than 1 mm in diameter. In some embodiments, the aperture is less than 0.5 mm in diameter. In some embodiments, the projection microlenses are refractive projection microlenses. In some embodiments, the projection microlenses are diffractive optic elements (DOE). In some embodiments, the projection microlenses are a combination of a refractive and diffractive microlenses.

In some embodiments of the disclosure, a projection microlens comprises a microlens wafer level optics array. In some embodiments, projection microlenses and imaging lenses are produced on the same lens array to provide mechanical stability and tight tolerances at low cost. In some embodiments, the projection microlens array is a glass molded array. In some embodiments, the projection microlens array is made of polymer microlenses on a glass array. In some embodiments, the projection lens is made of metamaterials.

An aspect of some embodiments of the disclosure relates to image pattern optimization. In some embodiments, the IOS communicates a received image of a tooth from the image sensor to a processing unit that, in turn, processes the acquired image for example for generating a 3D image (e.g., 3D computer model) of the tooth. In some embodiments processing the acquired image includes analysis of properties of an acquired image and automatically adjusting acquisition parameters based on the processing. In some embodiments, the processing unit processes a received image and automatically based on the processing, selects or signals IOS circuitry to select one or more of the plurality of micro light emitters a ray of which is incident on an axial surface of an imaged tooth at an angle from the surface thereof. Optionally the processor may segment a tooth and/or estimate 3D orientation of segments of a surface of the tooth.

Optionally the processor may estimate an angle of incidence of a beam on a ROI. For example, the estimated angle may account for a location of a light emitter and/or the angle of a surface segment in the ROI. In some embodiments the processing unit analyzes a received image and, based on the processing, automatically selects and activates one or more of the plurality of micro light emitters. For example, the processing unit may select and/or activate an emitter producing a beam having largest portion incident on a ROI and/or an emitter producing a beam having a direction closer to perpendicular to the ROI. For example, the ROI may be an axial surface of an imaged tooth. Alternatively or additionally, the processing unit may turn off or dim one or more non-selected emitters.

An aspect of some embodiments of the disclosure relates to movement of the IOS head. When the IOS is moved, the processing unit continuously or in quick succession processes received images at each point in time and/or automatically adjusts acquisition parameters based on the processing. In some embodiments, based on the processing the processing unit or IOS circuitry selects and activates one or more of the plurality of micro light emitters a ray of which is incident on an axial surface of the tooth at an angle between 30 and 90 degrees from normal the axial surface of the tooth. In some embodiments when the IOS is moved the processing unit continuously or in quick succession analyzes received images at each point in time and/or based on the processing automatically selects and activates one or more of the plurality of micro light emitters a largest portion of a beam angle of which is incident on an axial surface of an imaged tooth along to the axial dimension thereof and/or turns off or dims non-selected micro light emitters.

In some embodiments of the disclosure when the processing indicates contact of the elongated element with an axial surface or any other surface of an imaged tooth, the processing unit automatically adjusts acquisition parameters based on the detected contact. In some embodiments of the disclosure when the processing indicates contact of the elongated element with an axial surface or any other surface of an imaged tooth, the processing unit or IOS circuitry activates a light emitter that illuminates a side of the element not in contact with or opposite to the side of the element in contact with the axial surface of the tooth In some embodiments of the disclosure the IOS includes several imaging sensors and micro light emitters distributed about the elongated element and when the elongated element is placed in contact with the axial wall or any other surface of a tooth at locations around the circumference of the tooth, the processing unit or IOS circuitry activates one or more light emitters that illuminate a side of the element not in contact with or opposite to the side of the element in contact with the axial wall of the tooth.

An aspect of some embodiments of the disclosure relates to a downscaled IOS including one or more structured light casting micro-transparencies disposed between a micro light emitter and a projection microlens and cast structured light on a ROI. In some embodiments, the projection microlens casts structured light on the ROI. In some embodiments, the pattern is manually fitted to the direction of movement of the scanner and spatial orientation of the scanner in respect to the tooth being scanned. In some embodiments, the pattern is automatically fitted to the direction of movement spatial orientation of the scanner in respect to the tooth being scanned. In some embodiments, the structured light patterns and stereo or multiviews of oral features can be combined at the processing unit. In some embodiments, several micro light emitters project several overlapping structured light pattern orientations illuminate a common portion of the ROI in the field of view.

In some embodiments of the disclosure the processing unit processes a received projected structured light image and based on the processing automatically activates a micro light emitter that casts structured light providing the most precise image information. In some embodiments, the processing unit processes the received images including projected structured light and automatically selects and activates a micro light emitter that casts structured light having the highest contrast and/or resolution.

In some embodiments of the disclosure, the IOS includes a micro light emitter that projects light at two or more wavelengths. In some embodiments, the projecting microlens is a diffractive optical element (DOE) that creates a given pattern at two or more wavelengths such that the patterns differ by the wavelengths ratio. In some embodiments, the IOS includes an RGB light source. For example, the RGB light source may be behind the DOE and/or remote from the IOS head. For example, light may be transferred from a remote RGB light source with fiber optic delivery. In some embodiments, the IOS includes a multi wavelength light source including at least two wavelengths near the blue. In some embodiments, the RGB micro light emitter emits RGB light through a DOE. In some embodiments, the image sensor receives three separate pattern images at three different wavelengths cast on the field of view by the RGB micro light emitter. Optionally a processor may estimate a contrast of a projected pattern on a ROI. For example, the contrast estimate may account for incidence angle of the pattern on the ROI, distance from the ROI, power of a light emitter, and/or direction of features in the pattern.

An aspect of some embodiments of the current disclosure relates to an IOS having a form that is a familiar and/or convenient for a dentist. In some embodiments, the IOS may be shaped similar to and/or be configured as an add-on to a dental instrument. For example, the dental instrument may include a drill and/or a probe. Optionally, one or more projectors may cast light onto a ROI. For example, a processor may select and/or activate and/or deselect and/or deactivate a projector based on an incidence of the light and/or a projected pattern on the ROI and/or according to a movement of the IOS.

Optionally, one or more sensors may image the ROI. For example, a processor may select and/or activate and/or deselect and/or deactivate a sensor based on a FOV on the ROI and/or according to a movement of the IOS. Optionally, the IOS may be configured to collect 3D data above and/or below a gingival border. For example, the IOS may include a probe and/or may be used in conjunction with a probe to gather 3D data under the gingival border.

In some embodiments, an IOS probe may include an angled handle. Optionally, a handle may have a proximal portion adapted to be held by a dentist and/or a distal portion adapted to be inserted into the mouth of a patient. For example, the angle between an axis of the distal portion and the axis of the proximal portion of the angled handle may range between 0 to 10 degrees and/or between 10 to 30 degrees and/or between 30 to 60 degrees. For example, the angle between an axis of the distal portion and the axis of the IOS head may range between 90 to 80 degrees and/or between 80 to 60 degrees and/or between 60 to 30 degrees.

In some embodiments, an IOS tool may include a probe. Optionally the length of the probe may range between 0 to 5 mm and/or between 5 to 15 mm and/or between 15 mm to 25 mm and/or between 20 to 40 mm. Optionally the probe may have an average width ranging between 0 to 0.1 mm and/or between 0.1 mm to 0.3 mm and/or between 0.3 to 1 mm and/or between 1 mm to 3 mm. Optionally the probe may include fiducial markers and/or graduations for example indicating a distance of a point on the probe from the tip of the probe.

In some embodiments, an IOS may be used to explore regions under a gum line. For example, an IOS may include a probe. The probe may be used to explore regions below a gum line. Images produced by the IOS may be used to define the location of the probe and/or a feature touched by the probe under the gum line and/or to relate features imaged above the gum line to features explored below the gum line. The depth, angle and/or directional relationship between the probe tip under the gum line and/or revealed structures above the gum line are optionally estimated via image processing.

Optionally, a light source and/or an imager may be selected and/or deselected in order to improve an estimation of a location of a probe tip under a gum.

An aspect of some embodiments of the current disclosure relates to an IOS having optical components mounted to have synchronized and/or complimentary focal lengths and/or fields of view. For example, an imaging sensor and/or a light emitter of different dimensions may be mounted to have optical apertures along a plane facing a ROI and/or at a fixed distance from a ROI. For example, the optical components may be mounted with their optical apertures distributed along a plane perpendicular to the average direction of the beams of the emitters and/or average viewing direction (e.g. the directions to which the sensors face e.g. the line of sight of the viewer) and/or the combined average direction. For example, the average direction may be the unweighted average of vectors, each vector being an average direction of a beam of an emitter and/or an average viewing direction of a sensor. For example, a long element may be set back in relation to a short element. For example, setting back the long element may cause the optical apertures of the two elements to fall on a plane perpendicular to the mean viewing/beam direction. Alternatively or additionally, components with different focal lengths may be mounted at different heights to form a common FOV.

Alternatively or additionally, components of similar focal length may be mounted at different heights to create an array of components having a longer depth of field. For example, the components may be mounted on staggered PCB's and/or on a flexible PCB and/or with spacers.

Some of the CMOS sensors (or single CMOS with few apertures) are monochrome with higher sensitivity.

Some of the CMOS sensors are color for detection of the coding.

Some of the projectors monochrome (i.e. blue) for higher contrast over the tooth.

Some of the CMOS sensors are color for detection of the coding.

To improve the sampling of the probe location, higher frame rate, FPS (frames per second) of the imager is needed. The frame rate may be limited by the communication rate of the sensor. One way to improve that is to use higher FPS CMOS sensors. Another option for getting higher frame rate of the probe location is to interleave the different imagers reading over time (i.e. each sensor is read at a different time period using the same FPS rate). For example, the FPS of a group n of interleaved imagers may be n*FPS of each sensor.

An aspect of some embodiments of the invention relates to measurement of an edentulous dental arch. In some embodiments, the dental arch lacks one or more tooth. In some embodiments, the dental arch lacks 2-16 teeth. In some embodiments, the dental arch is entirely lacking teeth. In some embodiments, the dental arch includes one or more implant and, optionally one or more abutment attached to an implant.

In some embodiments, position and/or orientation of abutment/s are estimated from measurements. In some embodiments, a mouth model is generated and/or adjusted using the estimated position and/or orientation of abutment/s. In some embodiments, the position and/or orientation are integrated into and/or used to adjust an existing model (e.g. provided to a dental software program).

In some embodiments, a type (e.g. from a list of types) of abutment is selected. For example, by a processing unit based on measurement of the abutment. For example, by a user e.g. at a user interface. For example, based on other data e.g. previously collected IOS images and/or imaging using another modality e.g. X-ray, CT, MRI, ultrasound, nuclear imaging. In some embodiments, a model of the abutment type is incorporated into the model, potentially increasing model accuracy.

In some embodiments, IOS FOVs are selected so that one or more FOV captures at least one abutment (and/or other dental feature, e.g. tooth). In some embodiments, selection is manual (e.g. by a user). Alternatively or additionally, in some embodiments, the selection is automatic, e.g. using software tracking of position of the abutments as the IOS is moved during collection of measurements e.g. where FOVs are changed by moving portion/s of the IOS and/or IOS attachment while a body and/or head of the IOS remains stationary.

An aspect of some embodiments of the invention relates to a method of scanning a plurality of teeth, for example, 2-10 teeth, for example for preparation of a bridge dental prosthetic. In some embodiments, a first set of measurements is collected by positioning an IOS including at least two optical modules (e.g. imager-projector pairs) so that a first optical module collects image/s of a first part (e.g. end) of the region to be measured and a second optical module collects image/s of a second part (e.g. end) of the region to be measured. In some embodiments, a second set measurements are then taken by moving an IOS (the same IOS or a different IOS) along the region to be measured. Then, in some embodiments, accumulated error/s in the second set of measurements are corrected using the first set of measurements. For example, by adjusting the second set of measurements with known position of dental features and/or objects identified from the first set of measurements. In some embodiments, a large measurement region (e.g. a full arch) is scanned by performing the measurements for several regions making up the large measurement region, and then combining them.

Before explaining at least one embodiment of the disclosure in detail, it is to be understood that the disclosure is not necessarily limited in its application to the details of construction and the arrangement of the components and/or methods set forth in the following description and/or illustrated in the drawings and/or the Examples. The disclosure is capable of other embodiments or of being practiced or carried out in various ways.

Exemplary General Configuration of Exemplary IOS Head

The various optical components of the IOS (e.g., image sensor, imaging lens, projection lens, etc.) appear in the drawings in small scale numbers or as small groups of individual components, however the components depicted in the drawings are only representative of optical transmitters and receivers that consist of many independently located apertures, each component within an array controlled and activated individually or, alternatively, all operated as a unified coherent (or at least partially coherent) array. Each of the optical transmitters and receivers may include dozens and even hundreds of corresponding micro wafer level component arrays and/or individual modules. The optical IOS elements (e.g., imaging microlens, image sensor, projection lens, structured light micro transparency, etc.) in this disclosure relate, in some embodiments, but not exclusively, to micro lens arrays such as, for example, wafer level optics (WLO) components or individual lenses camera/projector modules.

Reference is now made to FIG. 1, which is a plan view and cross-section view thereof at level A-A (Section A-A) simplified illustration of a surface of a multiaperture optics intraoral scanner (IOS) head facing a region of interest (ROI), e.g., a tooth. As shown in FIG. 1, an IOS 100 includes a housing 102 shaped and sized to fit into an oral cavity with a head portion 150 and a handle portion 104. Handle 104 may be at various lengths indicated by two S-shaped break lines traversing the handle and sized to be optionally handled from outside the oral cavity. For example, a user may use a handle outside the oral cavity to manipulate the scanner inside the oral cavity. Optionally, handle 104 may house one or more components of IOS 100.

Optionally, IOS 100 may be in the form and size of a common dental turbine.

Optionally, in some embodiments IOS head 150 width may be between 5-25 mm. In some embodiments IOS head 150 width may be between 3-20 mm. In some embodiments, IOS head 150 width may be between 1-15 mm, less than 1 mm or more than 15 mm. In some embodiments, IOS head 150 length may be between 3-20 cm. In some embodiments IOS head 150 width may be between 5-25 mm. In some embodiments, IOS head 150 thickness may be between 10-20 mm, less than 10 mm or more than 20 mm. In some embodiments IOS head 150 thickness may be between 5-15 mm. In some embodiments, IOS head thickness may be between 3-10 mm, less than 3 mm or more than 10 mm.

As shown in FIG. 1, in some embodiments first surface 106 of intraoral scanner (IOS) 100 facing a region of interest (ROI) may include a plurality of imaging microlenses 110 or microlens arrays, disposed between one or more imagers or image sensors 112 and the ROI being scanned. As used herein the terms "Imager" and Image Sensor" are used interchangeably and apply generally to any image acquisition sensor.

Optionally, imaging microlenses 110 may be disposed within apertures 114 in first surface 106 and as will be explained in greater detail below project acquired images on one or more image sensor 110 or segments thereof. One or more image sensor 112 may be disposed within head 150, deeper than imaging microlenses 110.

In the embodiment of FIG. 1 and as will be explained in greater detail below, imaging microlens 110 may be an array 124 of microlenses, an array 124 of four microlenses is depicted in the example of FIG. 1. Each of array 124 microlenses optionally separately projects an image on a segment of image sensor 112. In some embodiments, acquired fields of view (FOVs) projected onto image sensor 112 by individual segments of imaging microlens array 124 at least partially overlap each other. The received image or images may be communicated by wire or wirelessly to a processing unit 116 for processing. In some embodiments a single final microlens 110 is disposed between image sensor 112 and the ROI so that a light ray incident on final microlens 110 continues travel directly to image sensor 112, i.e., a light ray traveling between final microlens 110 and image sensor 112 does not encounter any intermediate optical component on its way that changes the direction of travel (e.g., diverges, splits, bends, reflects or any other similar effect) of the light ray or at least a portion thereof.

IOS 100 head 150 may also include one or more micro light emitters 118 that emit light directly or through one or more projecting microlenses 120 in the general direction of an ROI. In some embodiments light emitter 118 may be at least one of a Surface-Mounted-Device Light-Emitting Diode (SMD LED) Module, a Chip on Board (COB) LED, a multi-COB (MCOB), an edge emitting Laser, a vertical-cavity surface-emitting laser (VCSEL), and/or a coherent or incoherent light delivery via optical fiber. In some embodiments, light emitters 118 may be controllably and mechanically moveable, e.g., mounted on a MEMS device.

In FIG. 1, a plurality of projecting microlenses 120, eight are depicted in FIG. 1, are disposed about or to one side of elongated element 108 located optionally centrally on surface 106. Optionally, projecting microlenses 120 may be disposed within apertures 122 in first surface 106 between one or more micro light emitters 118 and the ROI being illuminated. In some embodiments a single final projecting microlens is disposed between the light emitter and the ROI so that a light ray projected from one or more light emitters 118 travels directly to and is incident on projecting microlens 120, a light ray traveling between final microlens 110 and image sensor 112 does not encounter any intermediate optical component on its way. In some embodiments and as will be explained below, a structured light transparency may be disposed between light emitters 118 and projecting microlens 120. However, in some embodiments, a structured light pattern may be printed on light emitters 118 and/or projecting microlens 120 negating the use of a structured light transparency.

One or more micro light emitters 118 may be disposed within head 150 and deeper than projecting microlenses 120 disposed within apertures 122. As will be explained in greater detail below, a projection microlens 120 may be an array of projection microlenses, one example of which is microlens 120 array of projection microlenses depicted in the example of FIG. 8.

Optionally, IOS 100 may include an elongated element 108 optionally fixedly, optionally removably or optionally movably coupled to a first surface 106 of intraoral scanner (IOS) 100 facing a region of interest (ROI).

In FIG. 1, elongate element 108 is disposed in the center of surface 106. Elongated element 108 may be shaped as a stylus and have a diameter between 0.05-2.0 mm, optionally between 0.1 and 1.5 mm less than 0.05 mm or more than 2.0 mm.

Elongated element 108 may have a length measured from surface 106 between 1 and 25 mm, optionally between 2 and 20 mm, less than 1 mm or more than 25 mm. Optionally, elongated element 108 may be telescopic and may vary in length as required. Additionally and optionally elongated element 108 has a rounded or balled tip to be disposed against a tooth or oral tissue for stability.

Exemplary Implementation of Scanner Optics in an Exemplary IOS

The implementation of scanner optics described hereinbelow described using microimages and microlenses, which are components manufactured mainly by wafer level technology (see reference to FIG. 8 below) may not necessarily require use of miniaturized optical IOS components (e.g., wafer level imagers and light emitters, flat lenses and similar) and can be carried out employing commonly used suitably sized IOS components. The combination of the below described optical solutions and wafer level IOS components may contribute in concert to downsizing an IOS head.

Adaptation and modification of scanner optics may contribute to downscaling the IOS form factor. Processor 116 processing operation includes analysis of the properties of an acquired image at any specific point in time and under a given set of conditions at that specific point in time. Optical acquisition parameters and other parameters affecting the acquired image properties are also optionally integrated into the image processing operation and are adjusted in accordance with output from processing unit 116. Acquisition parameters may include spatial orientation of IOS head 150 in respect to an ROI, projected light parameters (number of light emitters, light intensity, coherence or non-coherence, wavelength, pulsed or continuous, pulse frequency, projected structured light pattern and others), direction and rate of IOS movement, focal length, FOV size, distance between ROI and imager and/or light emitter and more.

Figure 2B:
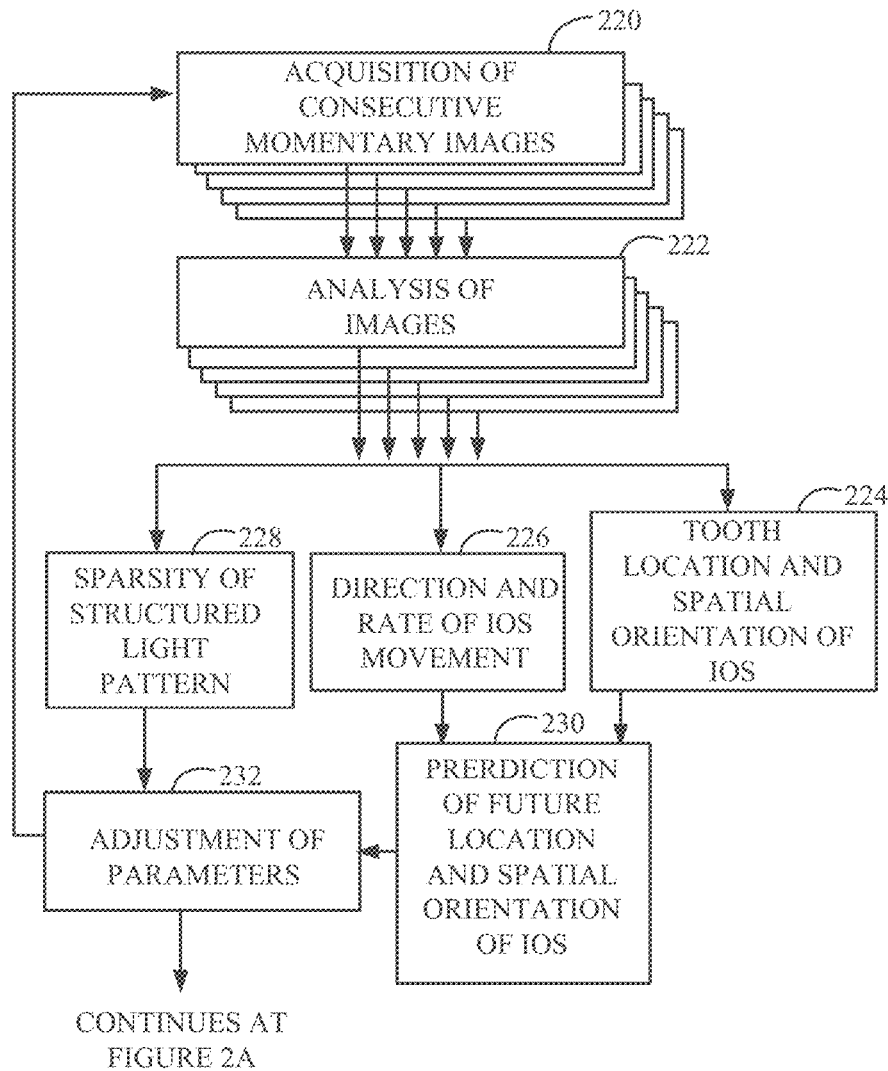

FIGS. 2A and 2B are exemplary flow charts of a processing unit 116 processing operation of an image acquired by IOS head 150. In FIG. 2A at 202 IOS 150 acquires a momentary image of a FOV of a ROI and communicates the acquired image by wire or wirelessly to processing unit 116. Analysis of the acquired image at 204 results in a depth image 206 of the FOV that provides ROI (e.g., tooth) location and spatial information of the imaged ROI such as depth, angles, hills and valleys, etc. as well as the spatial orientation of the IOS at 208 in respect to the imaged ROI.

At 210, FOV image properties such as, for example, image resolution, contrast, brightness, and/or color profile, etc. are extracted from the image analysis at 204. At 212, processor 116 receives analysis of image properties at 210, ROI (e.g., tooth) location and IOS spatial orientation in respect to the ROI at 208 and determines if any parameters require adjusting e.g., selection of a specific light emitter 118, brightness of projected light, etc. need to adjusted. If yes—processing unit 116 or IOS 150 circuitry signaled by processing unit 116 make the necessary adjustment at 214 based on the processing operation and inputted information at 216 of location of light emitters 118 and imagers 112 on IOS head 150. Adjustment at 214 may also include adjustment of IOS head 150 spatial orientation such as angularity in respect to ROI. This can be done manually by alerting the operator or automatically. Another momentary image is acquired and the process repeated. If at 212 no optic adjustments are required, at 218 the data resulting from the processing is outputted to the 3D model. All data analyzed at 212, including partial or incomplete information, may be outputted for construction of a 3D model. Optionally, at 204 analysis can include only image properties analysis 210 or depth analysis 206.

FIG. 2B illustrates processing of acquired images during movement of IOS head 150. At 220 and 222 a plurality of momentary consecutive images are acquired and analyzed similarly to steps 202 and 204 of FIG. 2A. The analysis at 222 provides at 224 the ROI (e.g., tooth) location and IOS spatial orientation in respect to the ROI at the corresponding acquisition time of the analyzed image, at 226 the direction and rate of IOS head 150 movement and at 228 the sparsity and required filling of the structured light pattern if such a pattern is cast on the ROI. The resulting data extracted from 224 and 226 provides at 230 means for prediction of future location and spatial orientation of IOS head 150 in respect to the current ROI. Processor 116 may also determine future necessary adjustments of IOS head 150 image acquiring parameters.

At 232, data from 230 regarding prediction of future location and spatial orientation of IOS head 150 may be combined with information from 228 regarding sparsity of a structured light pattern (if cast) and at 232 processing unit 116 adjusts or signals IOS head 150 circuitry to adjust parameters (e.g., light projection parameters). Adjustment at 232 may also include adjustment or change of structured light pattern as well as IOS head 150 spatial orientation such as angularity in respect to ROI. This can be done manually by alerting the operator or automatically. From step 232, processing continues back to step 202 of FIG. 2A and/or step 220 and repeated.

Adjustment of illumination of a light pattern projected on a region of interest (ROI) (steps 214, 232) may include in some instances, adjustment of the angle of incidence of projected light onto the scanned surface. The angle of incidence of the projected light may be detrimental to the accuracy of 3D information derived from the acquired image. For example, light incident on an axial surface of a tooth at too high an angle may result in a blurred or "smudged" image. This, commonly results from the returned light being far from the source of light or the perspective view of a striped light pattern viewed by the imager that may exhibit itself, for example, as having decreased distances between stripes. Light incident onto an axial surface of a tooth at generally a large angle in respect to normal an axial surface may, in some instances, contribute to the quality of the acquired image. In some instances, the tooth location in the image can be identified by the color of the tooth (e.g., to differentiate the tooth from gingival tissue) to determine the angle of incidence of projected light onto the scanned tooth.

Acquired image properties may be affected by the physiological or anatomical characteristics of the oral cavity. One example may be specular reflection from a tooth. As described above, in some systems powder is applied to the teeth in an attempt to achieve sharp and uniform reflectance of light and to provide texture to the surface of the tooth. However, the amount of an applied powder layer may be difficult to control resulting at times in excessive and/or non-uniform powder layer thickness resulting in reduction in accuracy of the constructed model as well as excessive stages and time for the IOS user.

In some embodiments processing unit 116 may identify, for example, a first region in the acquired image that is saturated due to specular reflection and select or signal IOS head 150 circuitry to turn off or dim the current active first light emitter and activate a second light emitter that illuminates a second region of the ROI (or same region) with a different incidence angle eliminating the specular reflection affecting the acquired image transferring the light saturation to a second region of the ROI. In some embodiments, a plurality of light emitters 118 can be alternately selected and activated so that to alternate between zones with specular reflection and zones free of specular reflection and acquire specular reflection free images. Similarly, a plurality of image sensors 112 may be used alternatively to acquire specular reflection free images. A combination of alternating image sensors 112 and light emitters 118 may also be used to produce specular reflection free zones in the ROI.

FIG. 3, which is a cross-section view simplified illustration of an example of implementation and adjustment of scanner optics, depicts intraoral scanner (IOS) head 150 scanning an axial surface or wall 202 of a tooth 300. Micro light emitters 118, 318 emit light through projecting microlenses 120 and 320 respectively that illuminates axial surface 202 of tooth 300. For purposes of simplification of explanation reference numeral 330 indicates a point of interest (POI) within a field of view (FOV) 332 of image sensor 112. A plane (Q) is tangent to axial surface 202 at POI 330 and normal to, extending in and out of, the surface of the paper. In the example of FIG. 3, light incident on surface 202 at POI 330 at an angle normal to plane Q tangent to POI 330 would be considered to produce optimal illumination conditions. In this example, the closer to normal the incident light may be the acquired image will have better properties such as, for example, clarity, contrast, speckle, visible light structure stripes or lines, etc.

As shown in FIG. 3, light incident on axial surface 202 POI 330 originating from light emitter 118 via projecting microlens 120, a general direction thereof indicated by arrow 350, is incident on axial surface 202 at an angle ($\alpha$) from plane (Q). Light incident on axial surface 202 POI 330 originating from light emitter 318 via projecting microlens 320, a general direction thereof indicated by arrow 370, is incident on axial surface 202 at an angle ($\beta$) from plane (Q). As shown in FIG. 3, angle ($\alpha$) is greater than angle ($\beta$) and closer to normal in respect to plane (Q) than angle ($\beta$).

Processor 116 may acquire and process images of FOV 332 communicated thereto by wire or wirelessly and illuminated by light emitter 118 as well as images of FOV 332 illuminated by light emitter 318 or a combination of illumination by both projectors 118, 318 or by any other combination of illumination. Based on the processing, processor 116 may, for example, activate light emitter 118 only; activate light emitter 118 and dim light emitter 318 or any other combination to provide the best possible 3D image of POI 330. In the example of FIG. 3, processing may indicate that projector 118 is optimal at the specific point in time and location of POI 330, angle of incidence ($\alpha$) being closest to normal, i.e., between 30 and 90 degrees from a plane (Q) and thus activate or signal IOS head 150 circuitry to activate light emitter 118 only. Optionally, the angle of incidence may be between 40 and 80 degrees, optionally between 50 and 70, less than 50 degrees or more than 70 degrees.

The angles of incidence of emitted beams can be determined using 3D location and angles of tooth and other measured oral feature in respect to known IOS micro projector and/or imager locations.

In an example depicted in FIG. 4, which is a cross-section view simplified illustration of an example of implementation and adjustment of scanner optics, IOS head 150 may include one, two or more image sensors 112, 412 and imaging lenses 110, 410 respectively imaging respective FOVs 434, 436. For purposes of simplification of explanation reference numeral 438 indicates a region of interest (ROI) on a tooth 400 within fields of view (FOV) 434, 436 of image sensors 112, 412 respectively. ROI 438 is generally planar defining a plane (Q) normal to, extending in and out of the surface of the paper. In the example of FIG. 3, a light beam incident on and illuminating a largest portion of surface 202 ROI 438, mainly along the axial dimension thereof would be considered to produce optimal illumination conditions.

As shown in FIG. 4, a light beam projected by light emitter 118 via projecting microlens 120 has a beam angle (γ). A light beam projected by light emitter 418 via projecting microlens 420 has a beam angle (θ). As shown in FIG. 4, beam angle (γ) is greater than angle (θ) and is incident on a larger portion of surface 202 ROI 438, mainly along the axial dimension thereof. Processor 116 may acquire and process images of FOVs 434 and 436 communicated thereto by wire or wirelessly and illuminated by light emitter 118 as well as images of FOV 436 illuminated by light emitter 418 or a combination of illumination by both projectors 118, 418 or by any other combination of illumination. Based on the processing, processor 116 may, for example, activate light emitter 118 only; activate light emitter 118 and dim light emitter 418 or any other combination to provide the best possible 3D image of ROI 438.

Alternatively and optionally, based on the processing, processor 116 may, for example, activate image sensor 112 only and turn off image sensor 412, activate both image sensors 112 and image sensor 412 and process a combination of images acquired from both or employ any other combination of light emitters 118, 418 and image sensors 112, 412 to provide the best possible 3D image of ROI 438. In the example of FIG. 4, processing may indicate that projector 118 is optimal at the specific point in time, size and location of ROI 438, having a largest beam angle and illuminating a largest portion of ROI 438, mainly in the axial dimension thereof and thus activate or signal IOS head 150 circuitry to activate light emitter 118 and/or image sensor 112 only. The illuminated portion along the axial dimension of the ROI may be between 30-100 percent, optionally between 50-80 percent and optionally between 60-70 percent of the axial dimension of the ROI.

Figure 5A:
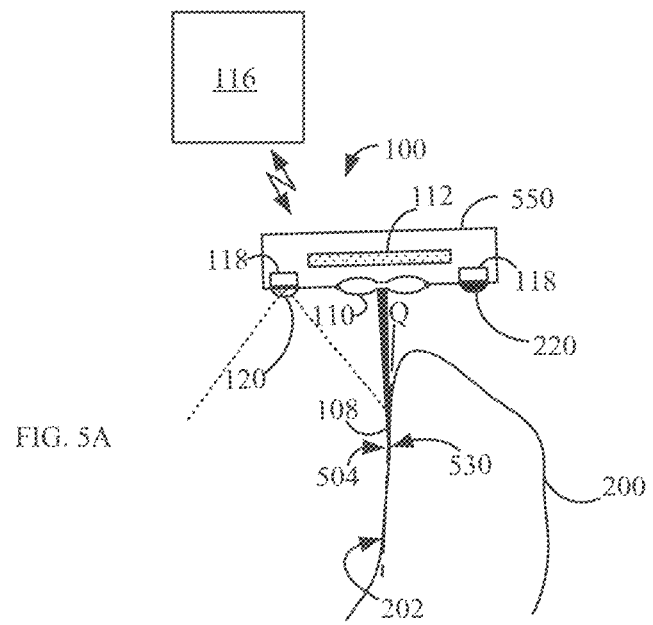
FIGS. 5A and 5B are cross-section and plan view simplified illustration of an example of implementation of scanner optics in accordance with embodiments of the current disclosure.
Figure 5B:
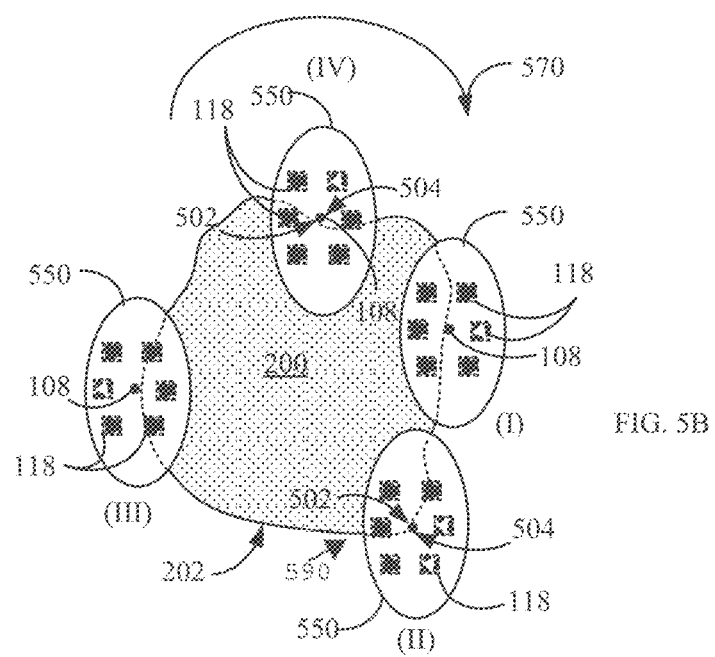

Reference is now made to FIGS. 5A and 5B, collectively referred to as FIG. 5, which are a cross-section view and top view simplified illustrations of an example of implementation and adjustment of IOS head 150 scanner optics. Circumferential scans are prevalent 3D mapping techniques of a tooth. As depicted in the example of FIG. 5, intraoral scanner (IOS) 100 includes an elongated element 108 in a form of a stylus. A plane (Q) is tangent to axial surface 202 at point of contact (POC) 530 and normal to, extending in and out of the surface of the paper.

In the example depicted in FIG. 5A, IOS 100 head 550 is positioned over tooth 200 with at least a portion 502 of element 108 in contact with axial surface 202. One or more images acquired through imaging microlens 110 and projected onto image sensor 112 may be communicated by wire or wirelessly to processing unit 116 for processing as explained hereinabove. Based on the processing of the received image or images of the ROI, processing unit 116 may automatically select and activate or signal IOS head 150 circuitry to adjust IOS optics such as, for example, to activate one or more of the plurality of micro light emitters 118 projecting light via projecting microlenses 120, 220 the light beam of which is incident on a non-contacting portion of a surface 504 of element 108. Optimally, non-contacting portion 504 is close to opposite to portion 502 in contact with axial surface 202.

Processing unit 116 may adjust IOS head 150 optics by, for example, turning off or signaling IOS head circuitry to turn off non-selected micro light emitters as indicated in FIG. 5A by a blackened microlens 220. Light incident on non-contacting portion of a surface 504 of element 108 optimally close to opposite to portion 502 in contact with axial surface 202 also incidents onto an axial surface 202 of a tooth in contact with element 108. Optionally, processor 116 may also select an imager 112 on the same side of the non-contacting portion 504 of element 108 not in contact with axial surface 202 of tooth 200. Element 108 may not necessarily be in contact with an axial surface of a tooth and may be in contact with any surface of the tooth.

FIG. 5B illustrates the process of micro light emitter selection by processing unit 116 described in reference to FIG. 2B as IOS 100 head 550 is moved along a circumference of a tooth 200 in a direction indicated by an arrow designated reference numeral 570. As described in FIGS. 2B and 5A above, processing unit 116 may automatically select and activate or signal IOS head 150 circuitry to activate one or more of a plurality of micro light emitters 118 the light beam of which is incident on a portion 504 of element 108, optimally, close to opposite to portion 502 of a surface of element 108 in contact with axial surface 202. For example, processor 116 may determine which of emitters 118 is between element 108 and the ROI. Optionally one or more of those emitters 118 is deselected and/or deactivated. For example, processor 116 may determine which of emitters 118 are positioned such that element 108 is between emitter 118 and the ROI. Optionally one or more of those emitters 118 are selected and/or activated. For example, processor 116 may determine which of sensors 112 is between element 108 and the ROI. Optionally one or more of those sensors 112 is deselected and/or deactivated. For example, processor 116 may determine which of sensors 112 are positioned such that element 108 is between sensors 112 and the ROI.

Optionally one or more of those sensors 112 are selected and/or activated.

In some embodiments, elongated element may contact a ROI in a hidden location, for example under a gum line. Optionally, processor 116 determines an orientation of element 108 with respect to the ROI and/or an orientation of IOS head 550 with respect to the ROI and/or element 108. In some embodiments, based on the relative orientation of head 550, element 108 and/or the ROI, processor 116 selects and/or actives a sensor 112 and/or a light emitter 118 that will produce an image from which the 3D location of the point of contact between element 112 and the ROI can be determined that will produce an image from which the 3D location can be determined more accurately.

Alternatively or additionally, processor 116 deselects and/or deactivates a sensor 112 and/or a light emitter 118 that will not produce an image from which the 3D location of the point of contact between element 112 and the ROI can be determined and/or that will produce an image from which the 3D location can be determined less accurately. Optionally, processor 116 predicts a future relative orientation of head 550, element 108 and/or the ROI. Optionally the selected deselecting and/or adjusting is based on the predicted future orientation.

As shown in FIG. 5B elongated element 108 of IOS head 550 in position (I) is in contact with an axial surface or wall 202 of tooth 200. Processing unit 116 may then select one or more micro light emitters 118 (indicated in FIG. 5B by a whitened micro light emitter (118) the light beam of which incident non-contacting portion 504 of element 108. Processing unit 116 may also turn off or dim non-selected micro light emitters as indicated in FIG. 5B by blackened micro light emitters 118.

As IOS head 550 is moved into position (II), the light beam of microlight emitter activated previously at position (I) is still incident on non-contacting portion 504 of element 108 as does a light beam emitted from an adjacent micro light emitter 118. Hence, both light emitters are selected and activated by processing unit 116 or IOS head 150 circuitry. In IOS head 550 at position (III), light from micro light emitters 118 previously activated in position (II) is no longer incident on non-contacting portion 504 of element 108 and they are turned off. A single micro light emitter 118 located on the opposite side of IOS head 150 is then selected and activated. In IOS head 550 at position (IV) once again the micro light emitter 118 previously activated in position (III) is now turned off or dimmed. An adjacent micro light emitter 118 the light beam of which is now incident on a portion 504 of element 108 optimally opposite to portion 502 of a surface of element 108 in contact with axial surface 202, which was previously [positions (I) through (III)] off is now selected and activated. Selection and deselection of light emitters to be activated can be done in quick succession while IOS head 550 is moved along the circumference of tooth 200 as described in reference to FIG. 2B.

Optionally, at position II, upon acquiring a momentary image of tooth 200 and based on previous consecutive acquired images, processing unit 116 may predict the direction and rate at which IOS head 150 is being moved as well as an expected turn around bend 590 in tooth 200 axial wall as explained in reference to FIG. 2B above.

Exemplary Structured Light Projection

In some embodiments, depth information can be obtained from a projected structured light pattern cast on a ROI and using at least one optical aperture. For example, U.S. Provisional Patent Application No. 61/745,744 filed 24 Dec. 2012 the contents of which are incorporated herein by reference in their entirety teaches how to take sub-gingival measurements and/or intraoral measurements. A user can use any type of pattern projection and any type of 3D reconstruction, for example, as known in art of IOS.

If a portion of a pattern is imaged through at least two apertures the differences between the two pattern images can be used to obtain depth information using stereo view or multi-view. In some embodiments of the disclosure optimization of an imaged tooth acquisition includes casting structured light onto the surface of the imaged tooth or ROI. The topography of the ROI deforms the cast pattern and the deformed image may be then acquired and communicated to processing unit 116 that processes the acquired image and extracts depth information therefrom.

The confined space in the oral cavity one example of which is the posterior area of the dental arcade, may at times set constraints that limit the ability to project a high quality structured light pattern, for example, casting structured light onto the imaged tooth from too high an angle resulting in, for example, crowding of projected stripes and/or low contrast of the structured light pattern reducing depth measurement accuracy.

Similarly to the described in reference to FIGS. 2A, 2B, 3 and 4, in some embodiments processing unit 116 may process an acquired structured light image and based on the processing automatically select and activate or signal IOS head 150 to activate one or more of the plurality of structured micro light emitters the structured light pattern of which produces the highest image quality (e.g., sparsity, contrast and resolution).

Referring back to FIGS. 1 and 3-5A-B, in some embodiments IOS 100 head 150 may include a plurality of image sensors 112. In some embodiments, a plurality of image sensors 112 may be dispersed about elongated element 108 coupled to IOS head 150 surface 106. In some embodiments, each image sensor of a plurality of image sensors 112 may be coupled to a micro light emitter 118. In some embodiments, a plurality of image sensors 112 may be dispersed about a single micro light emitter 118.

In some embodiments based on acquired image(s) processing unit 116 may automatically select and activate or signal IOS head 150 circuitry to activate one or more of image sensors 112 that receive an image from an imaging microlens 110 on which a light beam reflected from axial surface 202 incidents at an angle close enough to normal to a ROI on axial wall 202.

In some embodiments and as shown in FIG. 6, which is a cross-section view simplified illustration of an example of implementation and adjustment of scanner optics, head 650 of IOS 100 may include a plurality of image sensors 112, 612 and a micro light emitter 118 that may project light through a structured light micro transparency 602 and cast structured light via projecting microlens 110 onto an axial surface or wall 202 of scanned tooth 200.

In some embodiments, a smaller micro lens array can replace micro transparency 602 and including a structured light pattern mask to improve efficiency of production and reduction in cost. In some embodiments, the microprojector can include a diffractive optical element (DOE). In some embodiments, projecting lens 120 includes a structured light mask imprint or markings and projects structured light onto the surface of the ROI. Only a single light beam is illustrated in FIG. 6 for purposes of simplifying the explanation. A plane (Q) is tangent to axial surface 202 at POI 630 and normal to, extending in and out of, the surface of the paper.

Processing unit 116 may process a received structured light image of imaged tooth 200 as previously described in reference FIGS. 2A and 2B and based on the processing may automatically select one or more of the image sensors 112, 612 that acquires the most accurate image information (e.g., a light beam of an image incident on imaging microlens 110 reflected off axial surface 202 at an angle optimally normal to plane (Q).

In the example of FIG. 6, reflection angle ($\omega$) of the beam incident on image sensor 112 microlens 110 is greater than reflection angle ($\delta$) of the beam incident on image sensor 612 microlens 110. Hence, processing unit 116 may select image information received from image sensor 112 over image information received from image sensor 612, angle ($\omega$) being closer to normal to plane (Q) than angle ($\delta$).

Alternatively and optionally, processing unit 116 may select a combination of image sensors 112, 612 or a combination of image sensors 112, 612 and light emitter or projectors 118.

Reference is now made to FIGS. 7A, 7B and 7C, collectively referred to as FIG. 7, which are bottom view (viewed from the direction of the ROI) simplified illustrations of examples of implementation and adjustment of IOS structured light optics. In FIG. 7, some IOS head components have been removed for purposes of simplifying the explanation. FIG. 7A depicts an embodiment of an IOS head 750 having two image sensors 112 and a structured light projecting microtransparency 702 that projects a structured light pattern (not shown) onto a ROI.

In the example of FIG. 7, structured light projecting microtransparency 702 is rotatable about an axis normal to first surface 106 of IOS head 750 as indicated by a doubled headed arrow 770. Structured light projecting microtransparency 702 may be rotatable manually or automatically by processing unit 116 in which case the rotation of projecting microtransparency 702 in respect to IOS head 750 may be synchronized in correlation with the direction of movement of IOS head 750.

In FIG. 7, projecting lens 120 has been removed to reveal the schematically shown structured light pattern represented several lines of magnified structured light transparency 702. In some embodiments instead of rotating microtransparency 702, a spatial light modulator can be used such as used for mobile microprojectors, for instance transmissive or reflective (LCOS) micro displays or DMD or MEMS scanned mirror based microprojectors.

In the example of FIG. 7A, the structured light pattern is constructed of schematically drawn parallel lines, parallel to a baseline 706 connecting the center of optical image sensors 112 and normal to the direction of movement of IOS head 750 as indicated by an arrow 750. In this case, depth information can be obtained from the variations of a projected pattern over several images obtained by image sensors 112. Since the pattern lines are, in general, parallel to baseline 706 of image sensors 112 the variations of the projected lines in the two respective acquired images caused by depth variations will be similar in both sensors 112. However, other oral or teeth features will vary between the two acquired images and their depth information can be obtained using stereo vision.

The depth information obtained using structured light and stereo or multiview of oral features can be combined at processing unit 116. Additionally, in this configuration movement of IOS head 750, while scanning the tooth in the direction indicated by arrow 730 will bring about filling of information gaps resulting from the structured light pattern sparseness and increase the density of obtained depth surface by combining many sparse depth images of the pattern lines into a single dense depth surface at processing unit 116 increasing depth data resolution and a more accurate 3D image(s) and measurement. In some embodiments the pattern orientation of FIG. 7A can be used, for example, for scanning with IOS head 750 up and down in directions indicated by double headed arrow 790, in coronal and apical directions along an axial wall of a prepared tooth.

The schematic structured light line pattern projected by structured light projecting microtransparency 702 shown in FIG. 7B is rotated by 90 degrees in respect to the pattern shown in FIG. 7A so that the lines projected by structured light projecting microtransparency 702 are now normal to baseline 706 connecting the center of image sensors 112. In this configuration, depth information can be obtained from the variations of the projected pattern between the images obtained through image sensors 112. Since the pattern lines are in general normal to baseline 706 between optical image sensors 112 the variations of the projected lines in the two respective acquired images caused by depth variations will be opposite for each image sensor 112.

Depth information obtained using structured light and stereo or multiview of oral features can be combined at processing unit 116. In this configuration, movement of IOS head 750 in the directions indicated by double headed arrow 730 will almost not improve the sparseness of the structured light pattern and thus not contribute to resolution of the acquired image(s).

However, scanning around the tooth circumference and turning IOS head 150 along the circumference of the tooth will bring about filling of information gaps resulting from the structured light pattern sparseness and increase the density of obtained depth surface by combining many sparse depth images of the pattern lines into a single dense depth surface at processing unit 116 increasing depth data resolution and a more accurate 3D image(s) and measurement. This combined with the above described in reference to FIGS. 5A-B and 6 may lead to an increase in the density of the obtained depth surface by combining many sparse depth images of patterned lines into a single dense depth surface at processing unit.

In some embodiments, the pattern orientation may be correlated with the IOS scanning direction. For example, the above described use of the pattern of FIG. 7A to scan an axial surface of a tooth in apical and coronal directions or, optionally, using the pattern of FIG. 7B orientation for scanning with IOS head 750 around a prepared tooth, such as described and depicted in reference to FIGS. 5A-B and 6, together with processing unit 116 selecting and activating the proper micro light emitter 118 and projecting lens 120 which provide the optimal pattern direction according to scanning direction of the user.

In some embodiments processing unit 116 selecting and activating the proper micro light emitter 118 and projecting lens 120 which provide the optimal pattern direction according to scanning direction of the user as well as optimal scanning angle in respect to the axial surface of a tooth while scanning around the circumference of the tooth.

In FIG. 7C, structured light projecting microtransparency 702 is rotated to project a schematic line pattern of diagonal lines that are close to normal to baseline 706 connecting the centers of image sensors 112. In this example, variations of projected pattern or lines during movements will be different between the two images acquired by image sensors 112. These differences in pattern line variations can be used for removing or reducing depth ambiguities, e.g., in cases in which periodical or repetitive patterns are used.

The configuration of FIG. 7C has similar advantages to those of the configuration of FIG. 7B, for example, for scanning with IOS head 750 around a prepared tooth. This, combined with the above described in reference to FIGS. 5A-B, may lead to an increase in the density of obtained depth surface by combining many sparse depth images of patterned lines into a single dense depth surface at processing unit. Depth information obtained using structured light and stereo or multiview of oral features can be combined at processing unit.

In some embodiments several structured light projecting slides 702 with several pattern orientations can be used to cast patterns on a common portion of the ROI, so that processing unit 116 can select the most appropriate structured light projecting microtransparency 702 to use based on IOS head 750 orientation and position in respect to the location of tooth 200 and/or ROI and that provides best angle of view as described hereinabove to support high density depth image acquisition. In some embodiments, plurality of projectors can be activated simultaneously, and each projector has a different color and the relevant imagers are color imagers.

Utilization and optimization of scanner optics contributes to contrast, resolution depth accuracy and robustness of the acquired image and allows for use of smaller IOS components such as wafer level micro light emitters, microlenses and image sensors and nullifies the need for components such as, for example, mirrors, reflectors, optic fibers, splitters and other image relaying components between an end optical element (e.g., imaging lens) and image sensor or between micro light emitter and end optical element (e.g., projection lens) thus contributing to low form factor of the IOS.

Exemplary Structure and Positioning of Scanner Components in an Exemplary IOS

Figure 8:
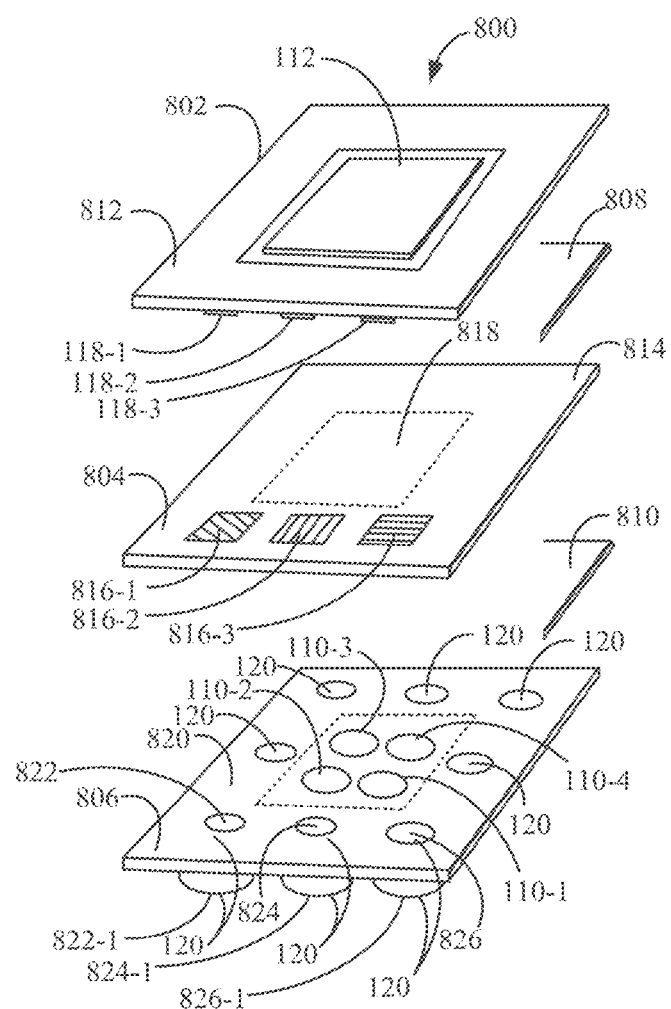
FIG. 8 is an exploded view simplified illustration of IOS 100 optical transmitters/receivers WLO module in accordance with embodiments of the current disclosure.

Reference is now made to FIG. 8, which is an exploded view simplified illustration of an example of an IOS 100 optical transmitters/receivers WLO module 800. WLO module 800 may be constructed as a multi-layered module the layers of which may be mechanically attached, manufactured together or bonded to each other in the final production step as wafers or at least some or all as diced elements or isolated elements. In the example depicted in FIG. 8, WLO module 800 includes three layers 802, 804 and 806 optionally separated by two spacer frames 808 and 810. Layer 802 may include an image sensor 112 or an array of image sensors 112 the imaging face thereof facing layer 806. Image sensor 112 may be a semiconductor charge-coupled device (CCD), a complementary metal-oxide-semiconductor (CMOS) or a similar type of optical sensor.

Optical sensor 112 may be framed by a light emitter 118 frame 812. Frame 812 may include a plurality of light emitters 118 facing in the same direction as image sensor 112 (e.g. the beam direction of emitters 118 is approximately parallel to the viewing direction of sensors 112), emitting light in the direction of layer 806. Three light emitters 118-1, 118-2 and 118-3 are visible in FIG. 8. Frame 812 can be made of PCB or Si wafer with mounted light emitters 118. Light emitters may be at least one of a Surface-Mounted-Device Light-Emitting Diode (SMD LED) Module, a Chip on Board (COB) LED, A multi-COB (MCOB), an edge emitting Laser, a vertical-cavity surface-emitting laser (VCSEL), and/or any similar suitable light emitter. Light emitters 118 can be packaged with or without a diffusing surface. Optionally, sensors 112 and/or emitters 118 are mounted with their optical apertures approximately along a plane. For example, the plane may be approximately perpendicular to the average beam direction of emitters 118 and/or the average viewing direction of sensors 112. For example, where the viewing direction and beam direction of each sensor 112 and/or emitter 118 are all approximately parallel, then the average direction is approximately parallel to all of the viewing directions and/or beams. For example, lines connecting the optical apertures of the components may all be within 0-2 degrees and/or 2-5 degrees and/or 5-10 degrees of perpendicular to the average beam direction of emitters 118 and/or the average viewing direction of sensors 112.

Layer 802 may be attached to spacer frame 808, which may or may not include optical elements such as condensing and/or diffusing elements under light emitters 118 (not shown). Spacer frame 808 may be attached to a glass wafer 814 that includes a plurality of structured light pattern transparencies 816, each corresponding to a light emitter 118. Three light pattern transparencies 816-1, 816-2 and 816-3 are shown in FIG. 8 corresponding to light emitters 118-1, 118-2 and 118-3. Structured light patterns 816 can be produced for example, with chrome lithography. Glass wafer 814 may also include a clear portion 818 corresponding the image receiving area of image sensor 112. Clear portion 818 may also be coated with a filtering coat, such as IR cut filter, spectral filters, AR coating, filter pixels, CMOS regions or any other suitable coat.

Glass wafer 814 may be attached to spacer frame 810, which in turn may be attached to layer 806. Layer 806 may be an integral microlens wafer 820 including micro optics image microlenses 110, projection lenses 120 and other suitable optical elements.

Additionally, fabrication of the above described WLO module 800 may provide better mechanical stability of the baseline between the projectors and image sensors which may result in acquisition of more accurate depth information and lower sensitivity to temperature and mechanical shocks (e.g., trauma to the IOS, IOS falling to the floor and similar). In some embodiments if the bond between image sensor and imaging lens in the image acquisition modules or bonded arrays is sufficiently accurate-baseline calibration may be unnecessary. Optionally, better mechanical stability can be achieved if WL microlenses technology is based on glass e.g., in glass molded array or polymer lenses on glass wafer.

Quality production of different types of microlens arrays on the same wafer contributes to efficiency of production and lowers production cost especially at mass production.

In the example of FIG. 8, microlens wafer 820 includes elements 822, 822-1; 824, 824-1 and 826, 826-1, each pair may be disposed on both sides of lens wafer 820 forming a projection microlens 120. Projection microlenses 120 can be made of a polymer or any other suitable clear material. The location of projection microlenses 120 may correspond to light pattern transparencies 816-1, 816-2 and 816-3 and light emitters 118-1, 118-2 and 118-3. Lens wafer 820 may also include a plurality of imaging microlenses 110 that correspond to segments of the pixel area of image sensor 112. Four imaging microlenses 110-1, 110-2, 110-3 and 110-4 in four apertures are shown in FIG. 8. Additional wafers with optical elements such as microlens wafer 820 with or without spacer frames can be added to improve optical quality. In addition, optical apertures for said lenses can be added on wafer 820, such as using chrome lithography or on additional wafer.

Microlenses 110 and 120 as well as well as image sensor 112 can be produced by parallel batch processing to cut costs. Parallel batch processing also enables the shrinkage of the imaging optics array track length contributing to miniaturization of the IOS head. In the example of FIG. 8, image microlenses 110 and projection 120 may be manufactured on the same array and bonded to an array of light emitters 118 and image sensor 112.

Manufacturing can include state-of-the-art micro-optical, WLO fabrication techniques. A total track length may be, for example, 1.4 mm, which is about half the length of comparable single-aperture optics on image sensors of the same pixel pitch.

Limiting the size of image acquisition modules, as explained in reference to FIG. 8, may provide the freedom to select a desired field of view(s) (FOV) that will provide the most precise information for processing unit 116 to reconstruct the most accurate 3D model from an acquired image. Do to their small size, such modules may be positioned about anywhere along surfaces of the IOS so that the user/processing unit 116 may select image acquisition modules that are most suitable at a certain point in time for generating a specific 3D image.

FIGS. 9A, and 9B, which are cross-section view simplified illustrations of embodiments of IOS head 150. In the embodiments of FIGS. 9A and 9B IOS head 950 includes one or more optic transmitters/receivers WLO modules 800-1 disposed on a first surface 906 facing a first region of interest (ROI). In FIGS. 9A and 9B, some IOS head components have been removed for purposes of simplifying the explanation.

Additionally and optionally, IOS head 950 may also include one or more second surfaces 914 facing a second and third region of interest (ROI). One or more second surfaces 914 may be angled in respect to first surface 106, mutually forming a convex third surface 920 each including one or more optic transmitters/receivers WLO modules 800-2.

In FIGS. 9A and 9B, convex third surface 920 is U-shaped. Each of first surface 906 and one or more second surfaces 914 respective optic transmitters/receivers WLO modules 800-1/800-2 may be disposed on convex third surface 920. Optionally, one or more optic transmitters/receivers WLO modules 800-3 may be disposed on a fourth surface 930, opposite to surface 906 and facing away from the first ROI. One or more optic transmitters/receivers WLO modules 800-3 on surface 930 may provide additional information for processing unit 116 regarding the location in the oral cavity and spatial orientation of IOS 100. Optionally, one or more optic transmitters/receivers WLO modules 800-3 on surface 930 may also allow an operator to select an upper jaw or lower jaw to be scanned without flipping IOS head 150 over or both jaws can be scanned simultaneously. Selection of FOV on either side of IOS head 150 can be done by manual or automatic selection.

In the example of FIG. 9A, the FOVs of One or more optic transmitters/receivers WLO modules 800-1, 800, 2800 do not overlap. Optic transmitters/receivers WLO modules 800-2 may provide image information of additional FOVs over the scanned tooth and/or other oral features supporting and contributing to image information acquired by optic transmitters/receivers WLO modules 800-1.

The information obtained from optic transmitters/receivers WLO modules 800-2 may assist in processing of the spatial orientation and position of IOS head 950 in the oral cavity. The FOVs of optic transmitters/receivers WLO modules 800-2 can be equal in size. Optionally and alternatively, the FOVs of optic transmitters/receivers WLO modules 800-2 can differ in size. In some embodiments, for example, the FOV of optic transmitters/receivers WLO modules 800-1 can be larger than the FOVs of optic transmitters/receivers WLO modules 800-2, e.g., the size ratio between the FOV of optic transmitters/receivers WLO modules 800-1 and the FOVs of optic transmitters/receivers WLO modules 800-2 may be 1.5:1; 2:1; 2.5:1; 3:1 or larger or smaller. In the example illustrated in FIG. 9B, FOVs of optic transmitters/receivers WLO modules 800-2 and 800-1 overlap and thus provide an extended single FOV from which spatial reference can be derived.

Reference is now made to FIG. 10, which is a cross-section view simplified illustration of an embodiment of IOS head. The IOS head may include a single image sensor 1012, a plurality of light emitters disposed on IOS head first and second surfaces 1006, 1014 respectively facing a first, second and third region of interest (ROI) respectively. First and second surface 1006, 1014 may each include at least one image acquisition lens 1002. Optionally, lens 1002 is manufactured by wafer level optics (WLO) technology and/or includes an optical transmitter/receiver wafer level optics (WLO) module 1010. Light incident on one or more image acquisition lenses 1002 disposed on first surface 1006 travels directly to and is incident on a first portion of image sensor 1012 pixel area. Light incident on one or more image acquisition lenses 1002 disposed on second surfaces 1014 travels to image sensor 1012 via one or more mirrors or prisms 1004 an is incident on a second and third portions of image sensor 1012 pixel area.

In the embodiment of FIG. 10, image sensor 1012 receives three images at one, each representative of a unique field of view (FOV) providing processing unit 116 information regarding IOS location in the oral cavity as well as IOS orientation in reference to a desired ROI (e.g., a tooth). Additionally, information received from each imaging lens 1002 complements and supports information received from the other imaging lenses 1002. The arrangement shown in FIG. 10 is compact thus supporting downscaling IOS head 150 by employing a single image sensor for acquiring several separate unique images.

Reference is now made to FIG. 11, which is a plan view and cross section view thereof at level C-C simplified illustration of an embodiment depicting implementation of optimization of positioning of scanner components. In FIG. 11, some IOS head components have been removed for purposes of simplifying the explanation. IOS head 1150 may include image acquisition modules 1102, 1104, 1106, 1108, 1112, 1114, 1116, and light emitting modules 1120 arranged about elongated element 108.

Optionally and alternatively, the FOVs of image acquisition modules 1104, 1106, 1114 can be equal in size. Optionally, image acquisition modules 1102, 1104, 1106, 1108, 1112, 1114, 1116, and 1118 may share the same image sensor employing spate lenses (not shown).

Optionally and alternatively, the FOVs of image acquisition modules 1104, 1106, 1114 can differ in size. In the embodiment of FIG. 11, image acquisition modules 1102, 1104, 1106, 1108 may have a standard FOV, e.g., between 30-90 degrees, optionally between 40-80 degrees, optionally between 50-70 degrees, less than 50 degrees or more than 70 degrees, whereas image acquisition modules 1112, 1114, 1116, 1118 may have an extra-wide FOV, e.g., between 80-160, optionally between 90-150 degrees, optionally between 100-140 degrees, less than 100 degrees or more than 140 degrees. In some embodiments, for example, the FOV of image acquisition module 1114 can be larger than the FOVs of image acquisition modules 1104, 1106, e.g., the size ratio between the FOV of image acquisition module 1114 and the FOVs of image acquisition modules 1104, 1106 may be 1.5:1; 2:1; 2.5:1; 3:1 or larger or smaller.

In the example illustrated in FIG. 11, FOVs of image acquisition module 1114 includes FOVs of image acquisition modules 1104, 1106 however, the focal length of image acquisition module 1114 may be different from the focal length of image acquisition modules 1104, 1106. For example, the ratio between the focal length of image acquisition module 1114 and focal lengths of image acquisition modules 1104, 1106 may be 1.5:1; 2:1; 2.5:1; 3:1 or larger or smaller.

This FOV combination supports acquisition of a high resolution image of an ROI (e.g., tooth) from the generally relatively narrower FOV image acquisition modules 1102, 1104, 1106, 1108 and better pose estimation using the wide angle FOV image acquisition modules 1112, 1114, 1116, 1118. The pose estimation may be needed for stitching depth images obtained at each frame into a single 3D model. Pose estimation can be obtained using algorithms such as structure from motion or bundle adjustment of all inputs obtained from all image acquisition modules or using sensors accelerometer, gyro, compass etc.

Exemplary Optimization of Exemplary Scanner Components

IOS 100 is a downscaled multi-aperture optics digital intraoral scanner (IOS) having a small form factor. In some embodiments head 150 houses all components necessary to generate a three dimensional (3D) image and measurement data sufficient to at least prepare a tooth prosthetic fitted to the tooth axial surface above and below the gingival border (gum line). This so that to shorten "communication lines" between IOS components by nullifying the need for mirrors, reflectors and other image relaying components and bring the various optic components (e.g., micro light emitters and sensors) as close as possible to the ROI so that to increase accuracy and precision of acquired 3D information. Additionally to utilization of IOS optics to reduce the form factor of IOS head 150, utilization of scanner component optics to reduce IOS head 150 form factor may also contribute to achieve the desired down-sizing of IOS 100 and especially head 150.

In some embodiments image sensor 112 is a semiconductor charge-coupled device (CCD), or such as a complementary metal-oxide-semiconductor (CMOS), with or without a color filter array (CFA) such as, for example, a RGB Bayer Filter or a similar type of optical sensor. In some embodiments image sensor 112 may acquire a single image projected onto its entire active pixel area. In some embodiments, a portion of image sensor or at least one of image sensors does not include CFA to improve sensitivity and a portion of image sensor or at least one of image sensors include CFA for providing color information of oral features and projected pattern.

In some embodiments, image sensor 112 may acquire a plurality of overlapping images projected onto its entire active pixel area. In some embodiments image sensor 112 may acquire a plurality of images each projected by an individual imaging microlens 110 or imaging microlens element onto a corresponding segment or fraction of image sensor 112 active pixel area. In some embodiments image sensor 112 can be formed be an array of image sensory elements formed on a wafer. In some embodiments, a plurality of image sensors 112 may be disposed deep within IOS head 150 first surface 106 about elongated element 108.

In some embodiments, imaging microlenses 110 may be segmented or fractionized, manufactured by WL optics technology using semiconductor-like techniques that produce an array of optical elements. In some embodiments a plurality of imaging microlenses 110 are manufactured as an array of imaging microlenses 110.

In some embodiments, an array of imaging microlenses 110 may be manufactured together with and bonded to a layered plurality of image sensors 112. In some embodiments an image sensors wafer may be diced together with the imaging microlens 110 array to provide individual image acquisition modules each including at least one imaging microlens 110 attached to one image sensor 112.

In some embodiments image sensor 112 and imaging microlens 110 array may not be diced and fitted as such in IOS 100 head 150. In some embodiments, WL microlenses may be made of metamaterials.

In some embodiments imaging microlenses 110 may be attached to a plurality of image sensors 112 using mechanical alignment. In some embodiments, imaging microlenses 110 may be bonded to a plurality of image sensors 112 and be aligned using active alignment. In some embodiments the imaging microlens 110 array may be bonded to a single image sensor 112. In some embodiments, the imaging microlens 110 array may be a glass-molded array. In some embodiments, the imaging microlens 110 array may be made of polymer microlenses on a glass support (e.g., UV molding of microlenses and application of cured polymer on glass wafers). In some embodiments, imaging lenses 110 may be made by other microlens array fabrication methods known in the art.

In some embodiments, projection microlenses 120 may be produced as a WL projection microlens array in an above described fashion similar to that of imaging microlenses 110 array. In some embodiments, an array of projection microlenses 120 may be manufactured together with and bonded to one or more micro light emitters 118 to form light emitting modules.

In some embodiments light emitters 118 may be micro optics light emitter such as, for example, a Surface-Mounted-Device Light-Emitting Diode (SMD LED) Module, Chip on Board (COB) LED, multi-COB (MCOB), Laser and vertical-cavity surface-emitting laser (VCSEL).

In some embodiments image sensor 112 may acquire image segments in which the imaging microlenses create a number of non-overlapping microimages on the image sensor active pixel area. The microimages represent part of the total FOV. Processing unit 116 may digitally or optically stitch the image segments (microimages) received from the image sensor to combine the received images and generate a single image of the FOV. This supports use of WL microlens arrays having a relatively narrow field of view (FOV). In some embodiments, multi-aperture optics may increase the effective imaging by having each WL microlens array segment project a low-resolution image of the full FOV on the image sensor. Processing unit 116 may then analyze the received images to create the final image of high resolution from partial images (e.g. from all partial images) (e.g., super resolution techniques).

In some embodiments, multi-aperture optics may increase effective 3D image acquisition by having each WL microlens array segment project an image of the full FOV on the image sensor, each image taken at a slightly different angle (shift). Processing unit 116 may then analyze the received images to create the final 3D image from all partial images.

Reference is now made to FIG. 12, which is a cross-section view simplified illustration of an embodiment of a multiaperture optics intraoral scanner (IOS), shows an IOS head 1250 including one or more color image acquisition modules 1202 (for instance, CMOS with RGB Bayer filter) and diffractive optic element (DOE) 1204 receiving one or more laser beams from one or more laser source 1206 in one or more wavelengths. In some embodiments, DOE 1204 may also include a collimating effect cone and a diffraction grating to create light stripes. In the embodiment of FIG. 12, laser source 1206 generates three laser beams at RGB wavelengths via a single optical fiber 1214 to DOE 1204 that casts a pattern 1210 on a ROI (e.g., tooth) 1212. In accordance with the grating equation [$\sin(\theta)=m\lambda/d$] the diffracted light pattern depends on its wavelength hence various portions of cast pattern 1210 will be modulated by a wavelength of the light beam creating the respective portion.

The RGB cast pattern forms three individual patterns each at one of the RGB wavelengths and the refracted patterns reflected off ROI 1212 may be acquired by one or more RGB image acquisition modules 1202 and communicated to processing unit 116. Processing unit 116 may process the acquired RGB patterns, for example, to solve ambiguity issues. Use of laser produced RGB wavelength light structured image may contribute to a low cost small form factor easily maneuverable instrument inside the oral cavity and comfortable for the patient.

In another embodiment, IOS head 150 may include at least one monochrome image sensor and at least one color image sensor both having the same FOV including a projected color structured light image. In this configuration, the monochrome and colored image sensors complement each other to provide an accurate acquired image at processing unit 116, the monochrome image sensor having a high sensitivity (approximately 3 times higher sensitivity than the color image sensor) and the color imager may be employed to prevent cross talk at the processing unit 116 level.

Other form of utilization of scanner component optics to reduce IOS head 150 form factor may also optionally include addition of mirrors to fold an optical path in instances in which imagers and/or projectors have a longer equivalent focal length (EFL). Optionally, different imagers may have different EFL to support different magnifications. Optionally, different imaging lenses may have different focal distances thus improving depth of the FOV. Optionally, imagers may be allotted different exposure times (by a processing unit) or include variable apertures to provide a better high dynamic range (HDR).

Figure 13:
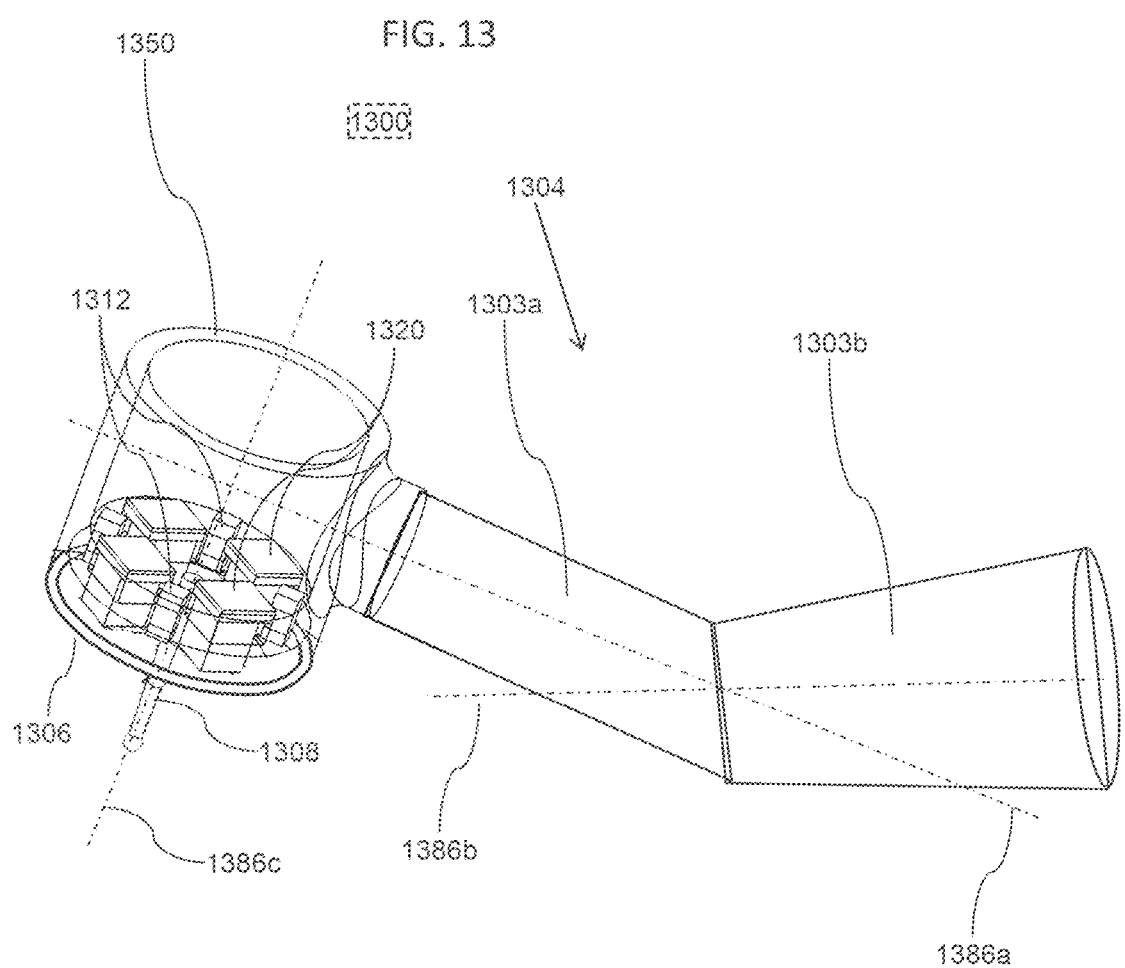
FIG. 13 is a perspective view simplified illustration of an embodiment of an IOS tool in accordance with embodiments of the current disclosure.

FIG. 13 illustrates an IOS scanner in accordance with an embodiment of the current disclosure. In some embodiments, an IOS scanner will be included in a tool having a form familiar to many dentists. For example, the IOS may be mounted on a tool shaped like a dental drill. Alternatively or additionally, the IOS may be mounted on a dental tool, for example a drill and/or probe.

In some embodiments, an IOS 1300 may include two or more sensor modules 1312 and/or two or more light emitters 1320. Optionally the sensor modules 1312 (for example image sensor) and/or light emitters 1320 (for example emitters and/or pattern projectors) may be combined together in a small form factor dental tool 1300. For example, dental tool 1300 may be shaped as a dental drill. For example, turbine shaped intraoral scanner 1300 includes four image sensor modules 1312, four light emitters 1320, a probe 1308 and/or a handle 1304. In some embodiments handle 1304 is angled similar to angled handles of some of dental turbines. Optionally a device may include between 1 to 4 sensor modules and/or between 5 to 10 sensor modules and/or more sensor modules. Optionally a device may include between 1 to 4 emitters and/or between 5 to 10 emitters and/or more emitters. Optionally the mean viewing direction of sensor modules 1320 and/or the mean beam direction of emitters 1320 is approximately parallel to an axis 1386c of the scanning head and/or approximately perpendicular to a surface 1306 facing a ROI. Optionally the mean viewing direction of each sensor module 1320 and/or the mean beam direction of each emitter 1320 are approximately parallel to each other and/or approximately parallel to the axis 1386 of the IOS head and/or approximately perpendicular to a surface 1306 facing a ROI.

In some embodiments, multiple sensor modules 1312 and/or emitters 1320 may be arranged on an IOS head 1350. For example, sensor modules 1312 and/or emitters 1320 may be arranged around probe 1308. For example, various emitters may include pattern generators having similar and/or different patterns and/or may have similar or different frequencies and/or orientation. For example, various sensor modules may include similar and/or different properties. Optionally a single sensor and/or emitter may be selected and/or activated to capture a desired view of a ROI.

Alternatively or additionally, multiple sensors and/or emitters may be selected and/or activated together and/or serially to capture a multiple views of a ROI.

In some embodiments probe 1308 is linear. Optionally an axis of probe 1308 is approximately parallel to an axis 1386c of IOS head 105. Alternatively or additionally probe 1308 may not be straight. For example, 1308 probe may be curved, bent and/or angled. Optionally a probe may include proximal end contacting the IOS head and/or a distal end opposite the proximal end. Optionally, the probe may include a distal portion next to the distal end and/or a proximal portion next to the distal end. Optionally the mean direction of the distal portion and/or the proximal portion may be parallel to axis 1386c of IOS head 1305. Optionally the distal portion and or the proximal portion may be linear.

In some embodiments, optical components (for example sensor modules 1312 and/or light emitters 1320) may be supported with their optical apertures on a single depth and/or on multiple depths with respect to a surface 106, 1306 facing a ROI, and or with respect to a viewing axis. For example, multiple sensor modules 1312 may have their optical aperture on a plane parallel to surface 106, 1306. This may, for example, facilitate acquiring multiple views of a single ROI. Optionally, an optical aperture of emitters 1320 may be on the same plane as sensor modules 1312. In some embodiments, viewing angles of multiple sensor modules 1312 may vary. In some embodiments, viewing angles of multiple light emitters 1320 may vary. In some embodiments, the length of components may vary. For example, the length of sensors 1312 may differ from the length of emitters 1320. Optionally, a compensation feature may align the optical apertures of components of different lengths. For example, for components mounted on a PCB, a compensation layer may lift short components off the face of the PCB and/or a flexible PCB may be flexed to align components and/or multiple rigid PCB's may be placed at different heights. Optionally multiple PCB's may be interconnected. Alternatively or additionally, individual components may be mounted separately at a desired height from a surface. In some embodiments, optical apertures may be mounted at a determined depth from a surface at an angle to the surface. For example, the components may be mounted to and/or positioned with respect to surface 106, 1306 facing the ROI and/or with respect to a curved surface and/or an angled surface.

In some embodiments, handle 1304 may include a distal portion 1303a and/or a proximal portion 1303b. For example, proximal portion 1303b may be adapted for handling by a dentist and/or distal portion 1303a may be adapted for insertion into the mouth of a patient. For example, the length of distal portion 1303a may range between 0 to 1 cm and/or between 1 cm to 3 cm and/or between 3 cm to 6 cm and/or between 6 cm to 20 cm. For example, the length of proximal portion 1303a may range between 0 to 5 cm and/or between 5 cm to 10 cm and/or between 10 cm to 20 cm and/or between 20 cm to 100 cm. In some embodiments an axis 1386a of distal section 1303a and an axis 1386b of distal section 1303b may form an angle ranging between 0 to 10 degrees and/or between 10 to 30 degrees and/or between 30 to 60 degrees. In some embodiments, an axis 1386c of IOS head 1350 and an axis 1386b of distal section 1303b may form an angle ranging between 90 to 80 degrees and/or between 80 to 60 degrees and/or between 60 to 30 degrees. It is understood that angular relationships recited herein also apply to elements that are parallel to a recited element and/or apply with a 90 degree rotation to elements that are perpendicular to a recited element.

In some embodiments, an array of components may be supported with optical apertures at different heights from a surface. For example, the optical apertures of multiple sensor modules may be fixed at different depths with respect to surface 1306.

In some embodiments, varying the depths of the optical aperture may increase a depth of field of the array. Alternatively or additionally, components having different focal lengths may be mounted at a single depth from surface 1306, for example to increase a depth of focus and/or components having different focal lengths may be mounted at a differing depth from surface 1306 to synchronize their focal length and/or get multiple views of a single ROI and/or the depth of a component with respect to surface 1306 may be adjusted according to its distance from a center of focus, for example to compensate horizontal position along plane 1306, for example to facilitate focus of multiple components onto a single point.

Figure 14:
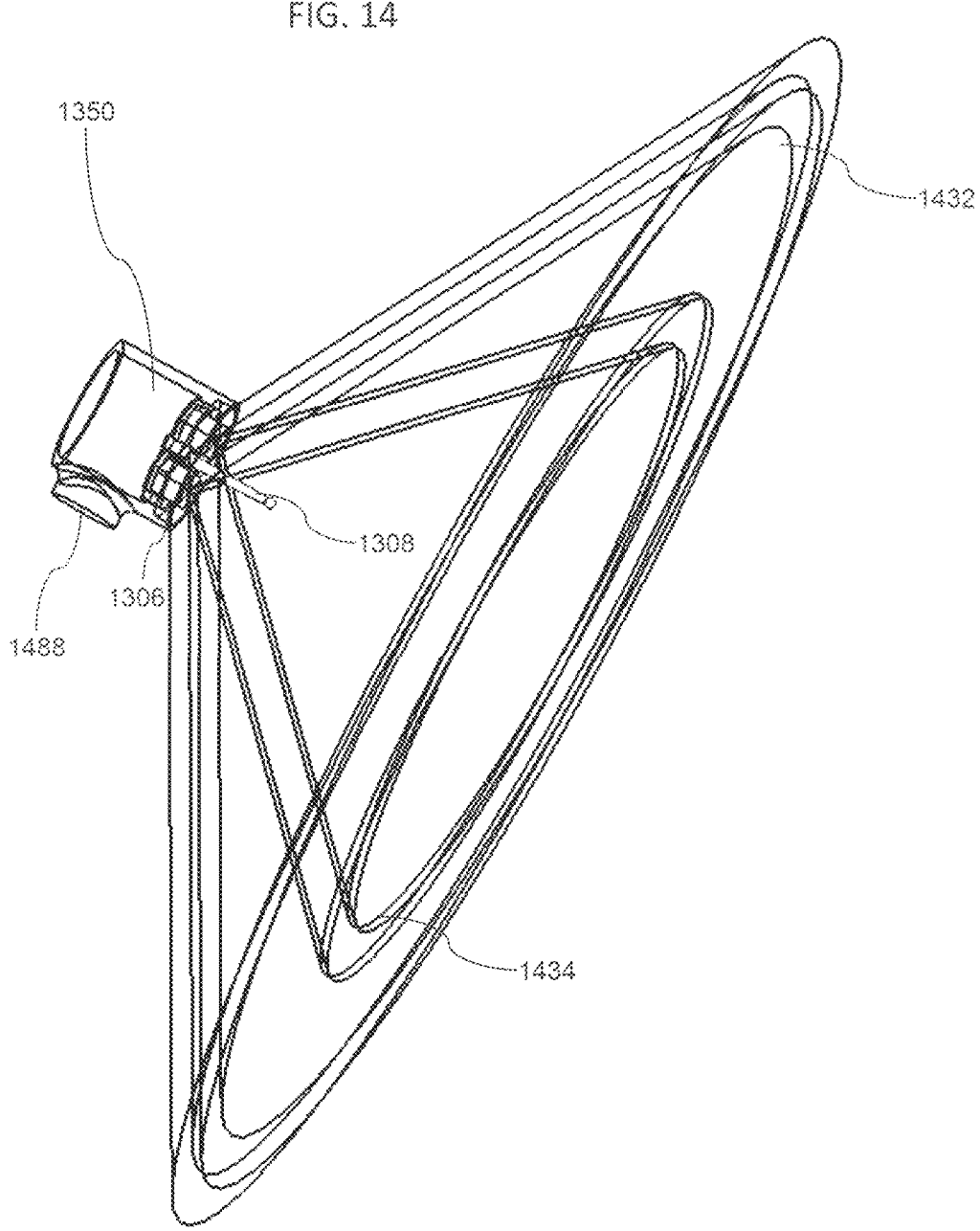
FIG. 14 is a perspective view simplified illustration of an embodiment of an IOS head in accordance with embodiments of the current disclosure.

FIG. 14 illustrates overlapping sensor module FOVs 1434 and/or light emitter FOVs 1432. Optionally, FOVs 1432, 1434 of various components (for example sensor modules 1312 and/or emitters 1320) may overlap and/or cover separate areas. Optionally, FOVs 1432, 1434 of various components may have a similar focal length and/or differing focal lengths. For example, illustrated FOVs 1434 of various sensor modules 1312 partially overlap. For example, illustrated FOVs 1432 of various emitters 1320 partially overlap. Optionally, FOVs 1432 of emitters 1320 surround FOVs 1434 of various sensor modules 1312. Alternatively or additionally, FOVs of emitters may partially surround FOVs of various sensor modules and/or be surrounded by FOVs of various sensor modules. IOS head 1350 includes an optional mount 1488. For example, mount 1488 may be configured to connect head 1350 to handle 1304.

In some embodiments, an IOS head (for example head 1350) may be mounted on a dental tool. For example, an annular IOS head may be mounted to a dental drill.

Optionally while a dentist is working the drill, the IOS head may be making images of a ROI.

In some embodiments, an IOS tool shaped as a dental tool may include a various other components and/or functionalities for example as described herein above. For example, the IOS device may include a built in processor and/or communicate with an external processor. For example, the processor may analyze an image and/or adjust parameters of the IOS. For example, locations of projectors and/or imagers may be adjusted over time according to a position and/or movement of the IOS with respect to an ROI.

FIGS. 15A-C and 16A-C illustrate various geometries of synchronized components and/or mounts. For example, various examples of staggered mounts are illustrated. In some embodiments, staggering components may align and/or disalign optical apertures. For example, the components may be mounted on staggered boards such as staggered rigid interconnected PCB's, a flexible PCB and/or a PCB with spacers.

Figure 15A:
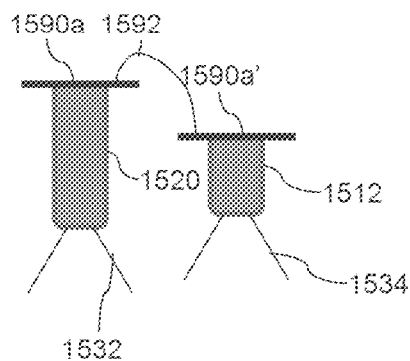
FIGS. 15A-C illustrate exemplary ways to align optical apertures in accordance with embodiments of the current disclosure.
Figure 16A:
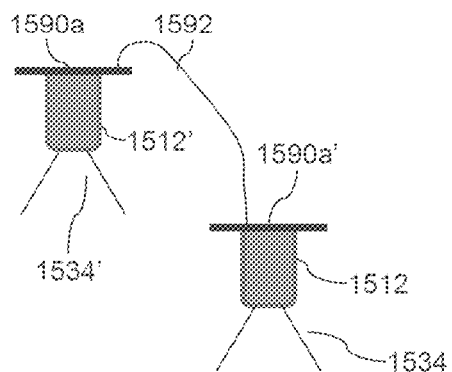
FIGS. 16A-C illustrate exemplary ways to disalign optical apertures in accordance with embodiments of the current disclosure.

In some embodiments (for example as illustrated in FIG. 15A) a long and a short component may be mounted with aligned optical apertures using separate PCBs. For example, a long light emitter 1520 and a short sensor module 1512 are mounted on separated PCB's 1590*a* and 1590*b* such that their optical apertures and/or FOVs 1532 and 1534 respectively are aligned, for example on a single plane. Optionally, PCB's 1590*a* and 1590*a*' are interconnected by a connector, for example a cable 1592.

Figure 15B:
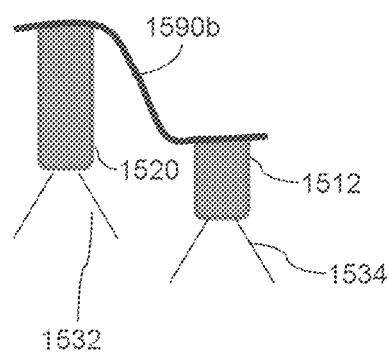
Figure 16B:
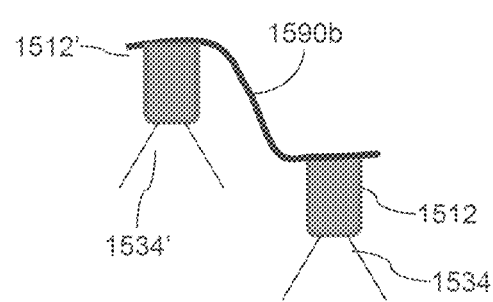
Figure 15C:
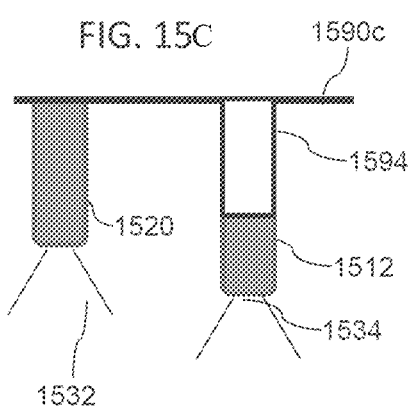
Figure 16C:
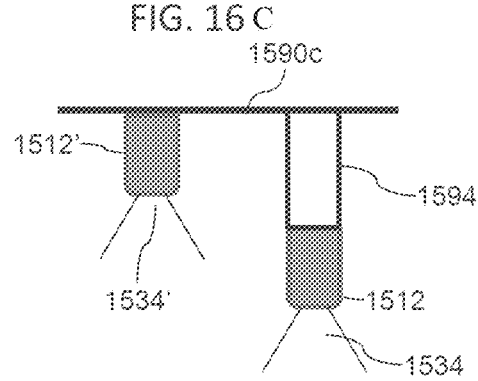

FIG. 15B illustrates mounting two components with disaligned optical apertures using separate PCBs. Optionally two similar sensor module 1512, 1512' are mounted on separated PCB's 1590*a* and 1590*b* such that their optical apertures and/or FOVs 1534 and 1534' respectively are disaligned, for example on separate planes. For example, such a geometry may be used to increase a focal length of a sensor array. For example, sensor 1512' will focus on a POI near the IOS device while sensor 1512' will focus on a POI further from the IOS device.

In some embodiments, FOVs be aligned and/disaligned using a flexible PCB. For example, in FIG. 15B, a long component (for example emitter 1520) and a short component (for example sensor module 1512) are mounted on a single flexible PCB 1590*b*. Optionally, the optical apertures and/or FOVs 1532 and 1534 are aligned by bending flexible PBC 1590*b*. For example, in FIG. 16B two similar components (for example sensor modules 1512 and 1512') are mounted on a single flexible PCB 1590*b*.

Optionally, the optical apertures and/or FOVs 1534 and 1534' are disaligned by bending flexible PBC 1590*b*.

In some embodiments, FOVs be aligned and/or disaligned using a spacer. For example, in FIG. 15C, a long component (for example emitter 1520) and a short component (for example sensor module 1512) are mounted on a single rigid PCB 1590*c*. Optionally, the optical apertures and/or FOVs 1532 and 1534 are aligned by mounting the smaller component on a spacer 1594. For example, in FIG. 16B a two similar components (for example sensor modules 1512 and 1512') are mounted on a single rigid PCB 1590*c*. Optionally, the optical apertures and/or FOVs 1534 and 1534' are disaligned by mounting module 1512 on spacer 1594.

Figure 17:
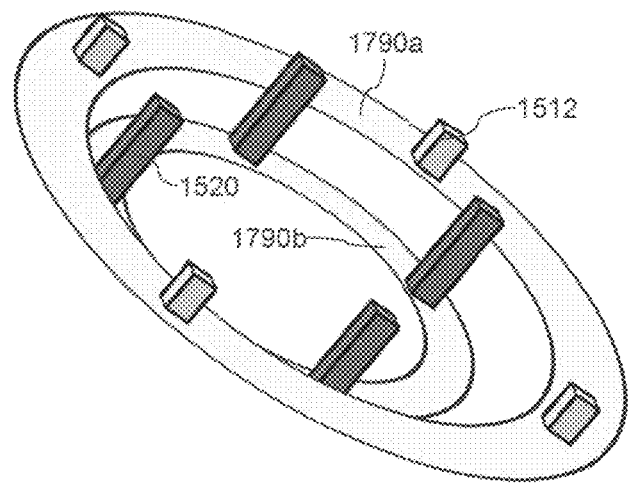
FIG. 17 illustrates staggered mounting of arrays of aligned optical components of an IOS in accordance with embodiments of the current disclosure.
Figure 18:
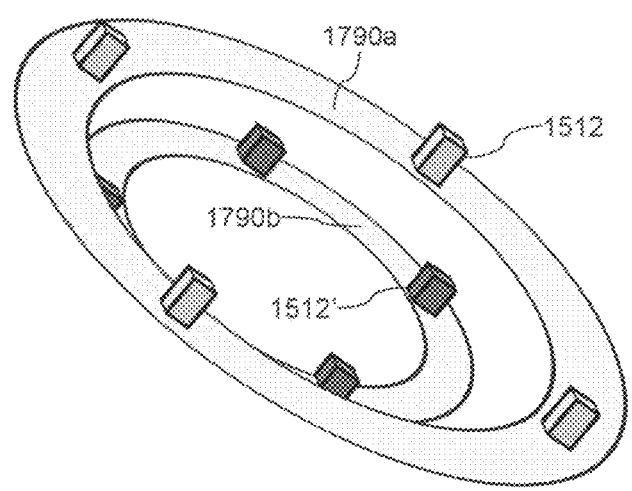
FIG. 18 illustrates staggered mounting of arrays of disaligned optical components of an IOS in accordance with embodiments of the current disclosure.

FIGS. 17 and 18 are illustrations of staggered arrays of sensor modules 1512 and/or emitters 1520. For example, FIG. 17 illustrates aligning optical apertures of an array of different sized emitters 1520 and sensors modules 1512 on staggered mountings 1790*a*, 1790*b*. For example, FIG. 18 illustrates disaligning optical apertures of an array of similar sized sensors modules 1512 and 1512' on staggered mountings 1790*a*, 1790*b*. Alternatively or additionally, mixed arrays of different and/or similar sized components may be may be aligned and/or disaligned. For example, FIGS. 17 and 18 illustrate concentric circular arrays of components. Alternatively or additionally, linear arrays may be staggered (for example like steps) and/or in other shaped arrays (for example rectangular and/or pentagonal and/or hexagonal).

Optionally staggered arrays may be concentric and/or arranged as steps and/or in another geometry.

Exemplary Variable Baseline IOS

FIGS. 19A and 19B are block diagram illustrations of scanners with variable baseline optics in accordance with an embodiment of the current disclosure. For example, an IOS may include more than one set of optical components (for example imagers and/or projectors). For example, one set of optical components with a short baseline between the imager module and the projector module may be used for imaging and/or acquiring a 3D model (for example a depth mapped image) of objects near the IOS and/or for acquiring a 3D model of detailed characteristics of an object. Optionally, a second set of optical components with a longer baseline between the imager module (including one or more imagers) and the projector module may be used for acquiring a 3D model of objects further from the IOS and/or for finding the relative position between objects over a larger area.

In some embodiments, multiple images of a projected pattern are by different imagers in the imager module and/or by a single imager making images from different viewpoints. Differences between images from different viewpoints may be interpreted to determine the depth as in stereo vision and/or to produce a 3D model.

In the exemplary embodiment of FIG. 19A, a first projector 1920*a* is optionally located on the IOS near an imager module 1912*a* (e.g. the baseline 1907*a* distance between the imager module 1912*a* and the projector 1920*a* is small). For example, when the IOS is used to image details on a nearby object (for example an object that is less than 15 mm from the imager module 1912*a*) imager module 1912*a* may be used to detect a pattern produced by projector 1920*a*.

In some embodiments, a second pattern projector 1920*b* may be located on the IOS further from imager module 1912a than projector 1920a (e.g. the baseline 1907b distance between the imager module 1912a and the projector module 1920b is larger than the baseline 1907a distance between the imager module 1912a and the projector module 1920a). For example, when the IOS is used to image details on a relatively far away object (for example an object that is more than 15 mm from imager module 1912a), imager module 1912a may be used to detect a pattern produced by projector 1920b. In some embodiments, the larger baseline 1907b may facilitate more accurate depth mapping.

In some embodiments, various characteristics of optical modules may be may be chosen to facilitate their intended use. For example, the focal distance of pattern projector 1920b may be larger (for example ranging between 15 to 50 mm) than the focus distance of projector 1920a (for example ranging between 1 to 15 mm).

Optionally, projector 1920b may have larger optical power than projector 1920a (which doesn't need to project a pattern at as large a distance as projector 1920b).

In the exemplary embodiment of FIG. 19B, a first imager module 1912b is optionally located on the IOS near a projector 1920c (e.g. the baseline 1907a distance between the imager module 1912b and the projector 1920c is small). For example, when the IOS is used to image details on a nearby object (for example an object that is less than 15 mm from the imager module 1912b) imager module 1912b may be used to detect a pattern produced by projector 1920c.

In some embodiments, a second imager module 1912c may be located on the IOS further from the project 1920c than imager module 1912b (e.g. the baseline 1907b distance between the imager module 1912c and the projector 1920c is larger than the baseline 1907a distance between the imager module 1912b and the projector 1920c). For example, when the IOS is used to image details on a relatively far away object (for example an object that is more than 15 mm from imager module 1912c), imager module 1912c may be used to detect a pattern produced by projector 1920c. In some embodiments, the larger baseline may facilitate more accurate depth mapping.

In some embodiments, various characteristics of optical modules may be chosen to facilitate their intended use. For example, the focus distance of imager module 1912c may be larger (for example ranging between 15 to 50 mm) than the focus distance of imager module 1912b (for example ranging between 1 to 15 mm). Optionally the depth of field of imager module 1912a (which is used for example to image objects at a distance between 5 to 50 mm) may be larger than the depth of field of imager sets 1912b and/or 1912c (which are, for example, intended to be used for either close or near objects, but not both). Optionally the depth of field of projector 1920c (which is used for example to project a pattern at a distance between 5 to 50 mm) may be larger than the depth of field of projectors 1920a and/or 1920b (which are, for example, intended to be used for either close or near objects, but not both).

In some embodiments, multiple imagers may be pared with multiple projectors. For example, in the example of FIG. 19A, two imager sets may be located close to the location of imagers module 1912a. One of the imager sets optionally has a long focus distance and/or is used with projector 1920b. The other imager module optionally has a short focus distance and/or is used with projector 1920a. For example, in the example of FIG. 19B, two projectors may be located close to the location of projector 1920c. One of the projectors optionally has a long focus distance and/or is used with imager module 1912c. The other projector optionally has a short focus distance and/or is used with imager module 1912b.

FIGS. 20A and 20B are schematic illustrations of use of a multiple FOV IOS in accordance with an embodiment of the current disclosure. In some embodiments, an IOS includes a first pair of optical modules (i.e. imager and projector or 2 imagers) having a short baseline and a second pair of optical modules having a longer baseline. For example, the first pair of modules may include an imager module 2012a paired to a projector 2020a. For example, the second pair of modules may include imager module 2012a paired to a projector 2020b.

FIG. 20A illustrates use of a multifocal IOS for scanning a close by object (e.g. tooth 2200b). For example, an object at a distance between 2 to 15 mm from the imager module 2012a may scanned using projector 2020a. Optionally the field of illumination 2034a of projector 2020a is directed and/or sized to overlap with the FOV 2032a of imager module 2012a at the small distance from the scanner. Optionally the base line distance between imager module 2012a and projector 2020a ranges between 0.5 to 5 mm. Optionally, the close FOV 2032a may have a width ranging between 1 to 15 mm (for example approximately the size of a single tooth 2200b In some embodiments, optical modules 2012a, 2020b and/or 2020a are mounted on a handle 2003 of the IOS. Alternatively or additionally, some or all of the optical modules 2012a, 2020b and/or 2020a are mounted on a head of the IOS. Optionally, the IOS includes a processor 2016. For example, processor 2016 may automatically control aspects of an optical component. For example, processor 2016 may switch between projectors 2020a and 2020b. For example, processor 2016 may switch on projector 2020a and/or switch off projector 2020b when the average distance to an object in the foreground of a FOV 2032a of imager module 2012a is less than 15 mm. For example, processor 2016 may switch on projector 2020b and/or switch off projector 2020a when the average distance to an object in the foreground of a FOV 2032a of imager module 2012a is more than 15 mm. Optionally, processor 2016 may be on board. Alternatively processor 2016 may be remote to and/or in communication with the IOS. Alternatively or additionally, an IOS may not be controlled by a processor.

FIG. 20B illustrates use of a multi FOV IOS for scanning an object that is further away (e.g. the three teeth 2200a-2200c). For example, for scanning an object at a distance between 10 to 50 mm from the scanner imager module 2012a may be used with projector 2020b. Optionally the field of illumination 2034b of projector 2020b is directed and/or sized to overlap with the FOV 2032b of imager module 2012a at the larger distance from the scanner. Optionally the base line distance between imager module 2012a and projector 2020b ranges between 5 to 50 mm. Optionally, the far FOV 2032b may have a width ranging between 10 to 50 mm (for example approximately the size of a three teeth 2200a-2200c. Optionally, said base line and/or FOV may be larger. In some, embodiments a far scan may be made with the IOS to determine the relative location of far away objects (for example tooth 2200a and tooth 2200c). In some embodiments, a far scan may be made with the IOS to image an object in a position that is in a difficult to access from nearby.

Figure 21:
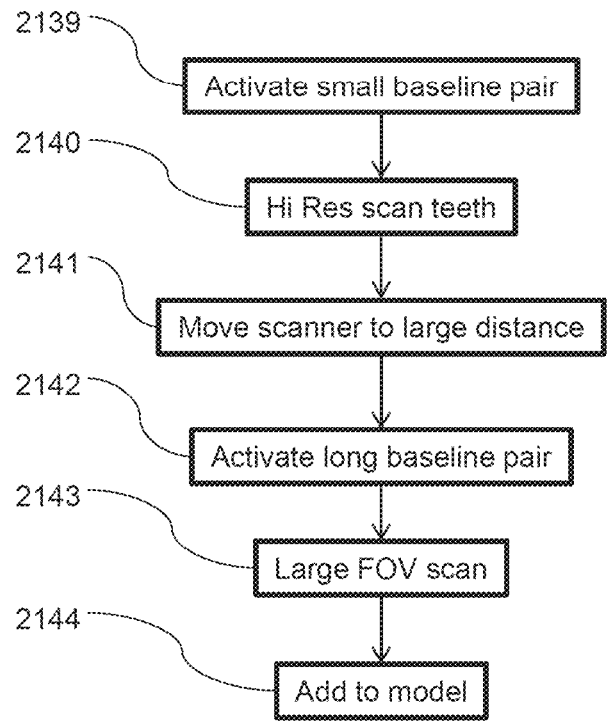
FIGS. 21 and 22 are flow charts illustrating methods of multi FOV scanning in accordance with embodiments of the current disclosure.
Figure 22:
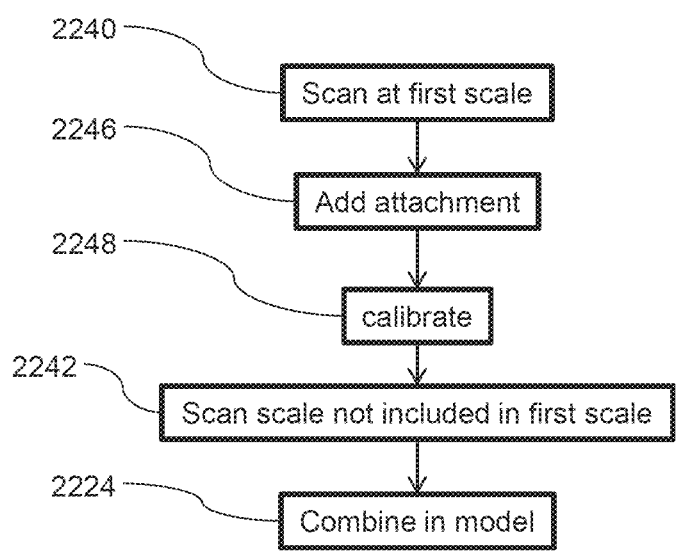

FIGS. 21 and 22 are flow charts illustrating methods of multi FOV scanning in accordance with embodiments of the current disclosure. In some embodiments, base line length will be increased as the distance to the scanned object increases. For example, increasing the baseline, may allow more accurate scanning of far away objects and/or large regions of interest.

FIG. 21 illustrates a method of scanning using multiple pairs of optical modules.

Optionally, a pair of optical modules that may be selected to produce an image with a desired characteristic and/or that is suited to a desired application. For example, a pair of modules having a long baseline may be chosen for scans a further distance and/or a shorter baseline for scans of a nearby object. Optionally, optical modules may be chosen with other characteristics to improve the scan, for example an appropriate focal distance, FOV, illumination power, pattern, etc.

In some embodiments, a pair of optical modules having a short baseline 2007*a* is selected and/or activated 2139 for scanning a close by object. For example, the short baseline pair may be used to scan 2140 a close-by object at a high resolution. For example, a portion of a tooth surface may be scanned 2140 at high resolution and/or some or all of a subject's teeth may be scanned 2140 at high resolution. In some embodiments, the high resolution scan may be made of small regions. Optionally, the relative positions of scanned objects may be computed by stitching together small FOV images.

In some embodiments, a scanner may be moved 2141 to a position further from a scanned object. Optionally, a pair of optical modules having a long baseline 2007*b* is selected and/or activated 2142. For example, the long baseline pair may be used to scan 2143 an object from far away and/or to scan a large region. In some embodiments, the scan is optionally added to a model of the scanned area 2144.

In some embodiments, the method illustrated in FIG. 21 may be performed using a scanner including multiple pairs of optical modules (for example as illustrated in FIGS. 19A, 19B, 20A, 20B, 32A-B and/or 33.

In some embodiments, a processor may integrate images. For example, by integrating images with large and small fields of view to reduce cumulative error and/or to achieve a small measurement uncertainty over a large region. For example, stitching small images together may achieve a positional accuracy of between 10 to 30 and/or between 30 to 50 μm and/or using large FOV images together may achieve a positional accuracy of between 10 to 30 and/or between 30 to 50 μm over the whole large FOV and/or reduce the effect of the accumulated error caused by stitching small FOV scans together. A few distant sections of the mouth may be scanned in the large FOV scan and the data used to correct relative positions throughout a model of the mouth. For example, the relative positions of between tooth 1 and tooth 16 on opposite sides of an arch may be measured and used to correct position data throughout the arch.

In some embodiments optical modules may be selected automatically. For example, a processor may track the distance between an imager and an object being imaged and/or the processor may select an appropriate optical module. Alternatively or additionally, the user may select the optical module. For example, the IOS may include a user interface, for example a button and/or a touch screen or the like by which the user may control the optical module selected. Alternatively or additionally, the user may select certain module by means of a gesture (for example the IOS may include a motion sensor that switches between modules when the device is moved suddenly and/or rotated. For example, the long baseline pair may be one side of the scanner and/or the short baseline pair on another side. Twisting the device one way may activate a first pair of modules and/or twisting the device in an opposite way may activate a different pair of modules. Alternatively or additionally, selecting an optical module may be by a combination of user action and/or automated action. For example, a processor may detect the distance to a scanned object and indicate to a user which optical module to select and/or when another module may give an improved image.

FIG. 22 is a flow chart illustrating a method of performing multi FOV scans using a FOV changing attachment in accordance with an embodiment of the current disclosure. In some embodiments, an IOS is used to scan with a first FOV and/or an attachment will be placed on the device to scan a different FOV. For example, the first FOV may be a small region measured at close range and/or the second FOV may be a further distance and/or a larger region. Optionally, one of the FOVs may be split, for example including a non-continuous region.

In some embodiments, an IOS will be used to scan 2240 a region at hi resolution. For example, the scan 2240 may be made using small FOV imager and/or possibly stitching together a large number of small FOV images. Optionally an attachment is added 2246 the IOS that changes the FOV of the device. For example, the attachment may change to FOV to include objects that are distant from each other. In some embodiments, the attachment may increase the size of the FOV. Alternatively or additionally the attachment may be change the shape of the FOV such that two locations may be seen simultaneously. Optionally the two location may be far apart (for example the distance between the locations may be larger than the FOV of the scanner, for example the FOV may be discontinuous). Optionally the relative positions of objects in the FOV may be known with a good precision. For example, the relative positions of objects in the FOV may be known to an accuracy ranging between 5 μm and 40 μm.

Optionally the attachment may be calibrated 2248 before use. For example, the relative position between the attachment and IOS may be measured and/or the device may be used to make an image of objects having a known relative positions and/or the positions of the object in the figure may be use to calibrate the image to determine the relative locations of objects in space based on their relative positions in the image.

In some embodiments, a region is scanned with the attachment. Optionally, the region scanned with the attachment includes scale that are not included in images made without the attachment 2242. For example, the device without the attachment may produce images at a scale of between 10 to 30 mm. Optionally, with the attachment two objects will be imaged that have a separation distance of greater than 30 mm. Optionally a 3D model will be made combining measurements at different scales 2224. For example, small features may be mapped to a high precision corresponding to small scale images and/or large scale relative positions in the image may be mapped to high precision based on images including far apart objects.

Exemplary Multi Projector IOS

Figure 32A:
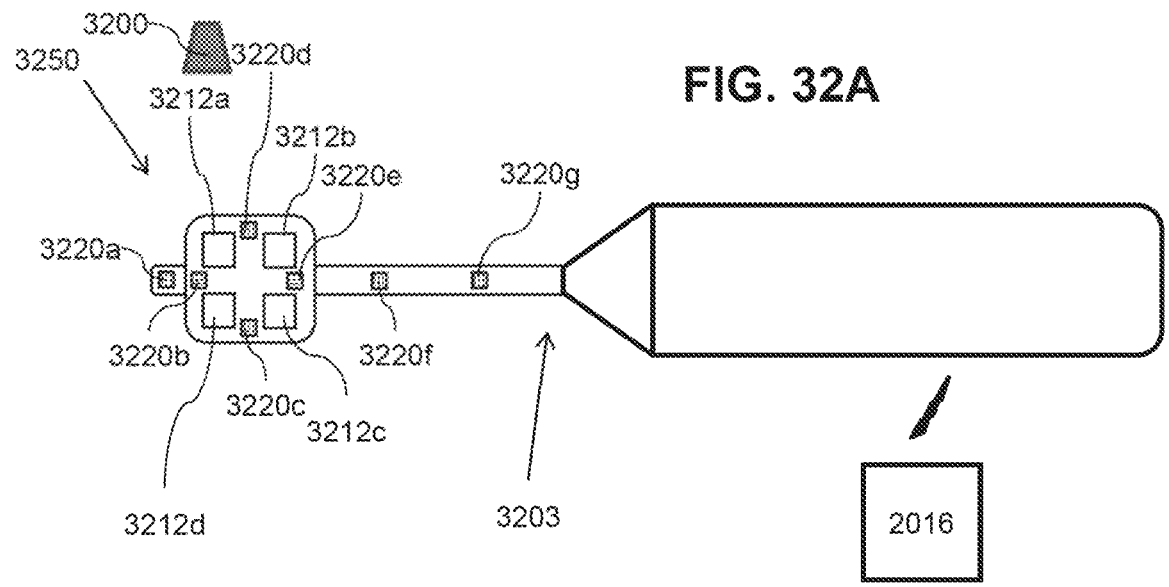
FIGS. 32A and 32B are schematic illustrations of an IOS's having adjustable baselines in accordance with an embodiments of the current disclosure.

FIG. 32A is a schematic illustration of an IOS having an adjustable baseline in accordance with an embodiment of the current disclosure. Optionally, the IOS includes multiple pattern projectors. For example, a pair of an imager module and a pattern projector module are selected according to the distance and/or direction to an object being measured. In some embodiments, an IOS may include one or more imagers 3212*a*-3212*d* and/or one or more pattern projectors 3220*b*-3220*e* located on an imaging head 3250. Further pattern projectors are optionally located further from the imagers 3212*b*-3212*d*. For projectors 3220*f* and 3220*g* are positioned on a handle 3203 of the IOS and projector 3220*a* is located on projection from head 3250. Imagers 3212*a*-3212*d* are optionally implemented as separate imagers, for example using separate CMOS sensors. Alternatively or additionally, separate imagers may be implemented using separate lenses and/or a single larger CMOS sensor and 4 optical apertures.

In some embodiments, projectors 3220*b*-3220*e* are located on the IOS close to imagers 3212*a*-3212*d* and/or are used for scanning short depth distances (form example when working with the IOS close to the tooth being scanned). For example, projectors 3220*b*-3220*e* may be used at working distances of 1-10 mm between the imager and the object being scanned. Optionally, projectors 3220*a*, 3220*f* and 3220*g* are located at a larger baseline distance from imagers 3212*a*-3212*d*. For example, projectors 3220*a*, 3220*f* and 3220*g* are used for scanning at larger distances (i.e. scanning with IOS several teeth) than projectors 3220*b*-3220*e*. For example, projector 3220*a* may be configured for use at distances of 10-20 mm, projector 3220*f* may be configured for use at distances of 20-30 mm and/or projector 3220*g* may be configured for use at distances of 30-40 mm.

In some embodiments, the selection of which projector to operate may be done manually by the user (i.e. the dentist) or automatically by an algorithm running on a processor 2016. For example, when processor 2016 detects that a working depth is between 20-30 mm (for example because the majority of the foreground of the images are between 20-30 mm from imagers 3212*a*-3212*d*), processor 2016 optionally turns off projectors 3220*a*-3220*e* and 3220*g* and activates projector 3220*f*. When processor 2016 detects that the working depth is larger than 30 mm it turns off projector 3220*f* and activates projector 3220*g*.

In some embodiments, as an alternative to and/or in addition to having additional projectors for the larger working baselines, there may be additional imagers with larger baseline and/or configured for larger working distance. In some embodiments, projectors and/or imagers with larger baseline are configured for larger working distance (for example with larger focal lengths and/or higher projection power and/or higher sensitivity).

In some embodiments, pattern projectors 3220*a*-3220*g* project patterns including line and/or linear patterns. Alternatively or additionally the projectors may project other shapes. For example, the lines and/or other shapes may be configured for removing the ambiguity in the resulting images. For example, lines and/or breaks, and/or color.

Optionally the general direction of the linear features is called the lines direction.

In some embodiments projectors (for example projectors 3220*b*-3220*e*) have line pattern which are perpendicular to the line that that connects the 2 closest imagers. For example, lines projected by projector 3220*b* are perpendicular to a line joining imagers 3212*a* to 3212*d*. For example, lines projected by projector 3220*c* are perpendicular to a line joining imagers 3212*d* to 3212*c*. In some embodiments, depth extraction is based on the difference between images from the two closest imagers to the pattern projector.

Optionally, the depth is computed based on the difference between the patterns visible in each of the images obtained by each the two closest imagers. Projected pattern are optionally configured to emphasize this difference for example by making pattern lines perpendicular to the gap.

In some embodiments projectors (for example projectors 3220*a*, 3220*f* and 3220*g*) which are more distant from the imagers 3212*a*-3212*d* have a line pattern which is parallel to the line that that connects the 2 closest imagers. For instance for projector 3220*a*, pattern line/s are optionally parallel to the line that that connects the 2 closest imagers (e.g. imagers 3212*d* and 3212*a*). Optionally, the depth can be extracted from the difference between the patterns obtained in each of the images obtained in each the two closest imagers (e.g. imagers 3212*d* and 3212*a*). In some embodiments the known projected pattern from projectors 3220*f*, 3220*g* and 3220*a* has a higher depth accuracy than from projectors 3220*b*-3220*e* due to the increased baseline.

In some embodiments the width of imagers (e.g. imagers 3212*a*-3212*d*) ranges between 1 to 10 mm. Optionally the distance between the centers of imagers 3212*a*-3212*d* ranges between 10 to 25 mm. Optionally the width of a projector (e.g. projectors 3220*a*-3220*g*) ranges between 1 to 10 mm. Optionally, the distance from a line connecting the centers of two imagers (for example imagers 3212*a* and 3212*b*) to the closest projector (for example projector 3220*d*) optionally ranges between 1 to 15 mm.

Optionally, the distance from a line connecting the centers of two imagers (for example imagers 3212*a* and 3212*d*) to projector 3220*a* optionally ranges between 5 to 20 mm. Optionally, the distance from a line connecting the centers of two imagers (for example imagers 3212*b* and 3212*c*) to projector 3220*f* optionally ranges between 10 to 30 mm. Optionally, the distance from a line connecting the centers of two imagers (for example imagers 3212*b* and 3212*c*) to projector 3220*g* optionally ranges between 20 to 40 mm.

Figure 32B:
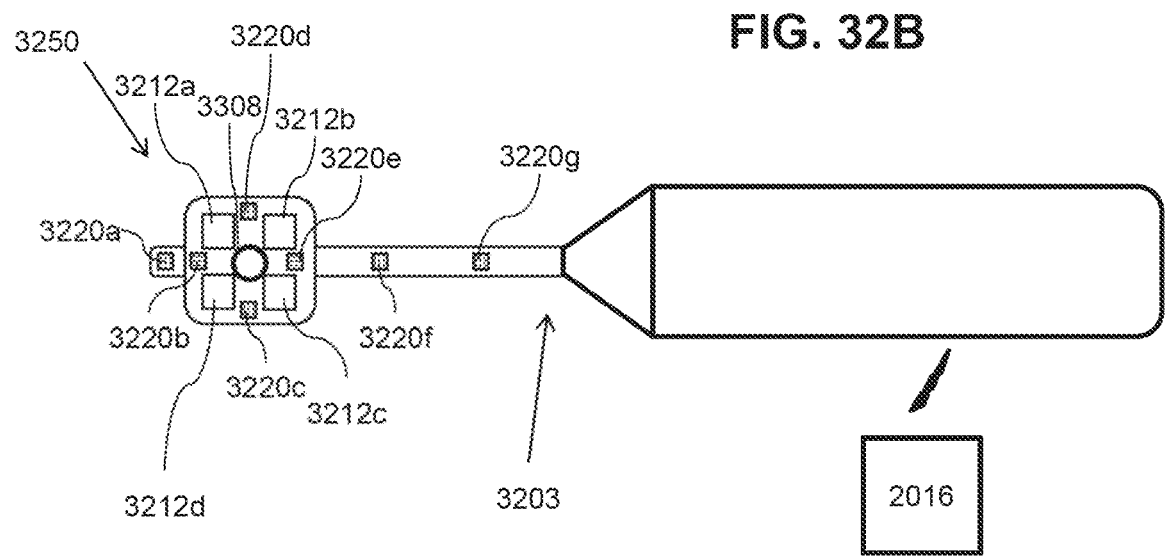

FIG. 32B is a schematic illustration of a multifocal IOS including a probe in accordance with an embodiment of the current disclosure. In some embodiments, a probe may be used to increase the accuracy of measurement of exposed (e.g. supergingival) surfaces and/or to measure hidden surface (for example subgingival tooth surfaces under a gum line). Optionally, when probe 3308 touches a surface being measured (which implies that the surface is at a distance equal the length of the probe for example between 6 and 10 mm) one of projectors 3220*b*-3220*e*, which are near the imagers 3212*a*-3212*d* is activated.

Figure 32C:
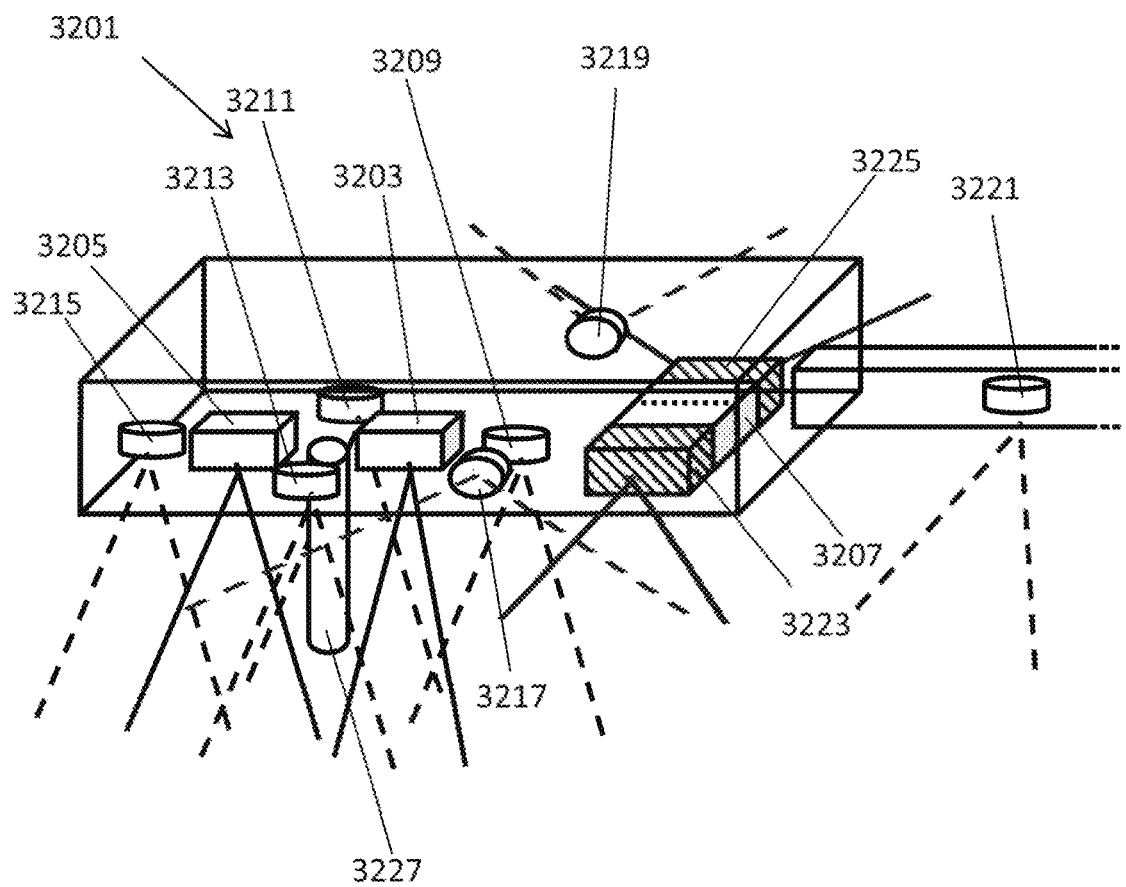
FIG. 32C is a simplified schematic illustration of a multifocal IOS including a probe and a plurality of imagers directed in different directions, according to some embodiments of the invention.

FIG. 32C is a simplified schematic illustration of a multifocal IOS 3201 including a probe and a plurality of imagers directed in different directions, according to some embodiments of the invention. In some embodiments, FIG. 32C illustrates FOV of imagers with solid lines and FOV of projectors with dashed lines.

In some embodiments IOS 3201 includes a one or more imager 3203, 3205 including FOV directed in a first direction. In some embodiments, IOS 3201 includes one or more projector with FOV directed in the first direction 3209, 3211, 3213, 3215, 3221. In some embodiments, IOS 3201 additionally includes one or more imager 3207 with FOV directed in at least a second direction.

In some embodiments, an imager is a split imager 3207 where, in some embodiments, prisms 3223, 3225, a FOV of the imager 3207 in at least two directions.

In some embodiments, more than one imager 3203, 3205, is directed in a first direction, the "multiple apertures" enable measurement of dental features from more than one angle potentially improving accuracy of measurements.

In some embodiments, at least one or, in some embodiments, all FOVs of imager 3207 are directed in different directions to that of imagers 3203, 3205. For example, perpendicular to the direction of FOVs of imagers 3203, 3205.

A potential advantage of FOVs of imagers being directed sideways is the ability to image sideways (e.g. when imagers are directed downwards) potentially increasing accuracy of full arch and/or edentulous measurements.

In some embodiments, IOS 3201 includes one or more projector 3217, 3219, including FOV/s directed in a different direction (e.g. perpendicular to) from that of projectors 3209, 3211, 3213, 3215, 3221. In some embodiments, projectors 3217, 3219, have FOVs directed in the same directions as imager 3207 FOVs.

Figure 23B:
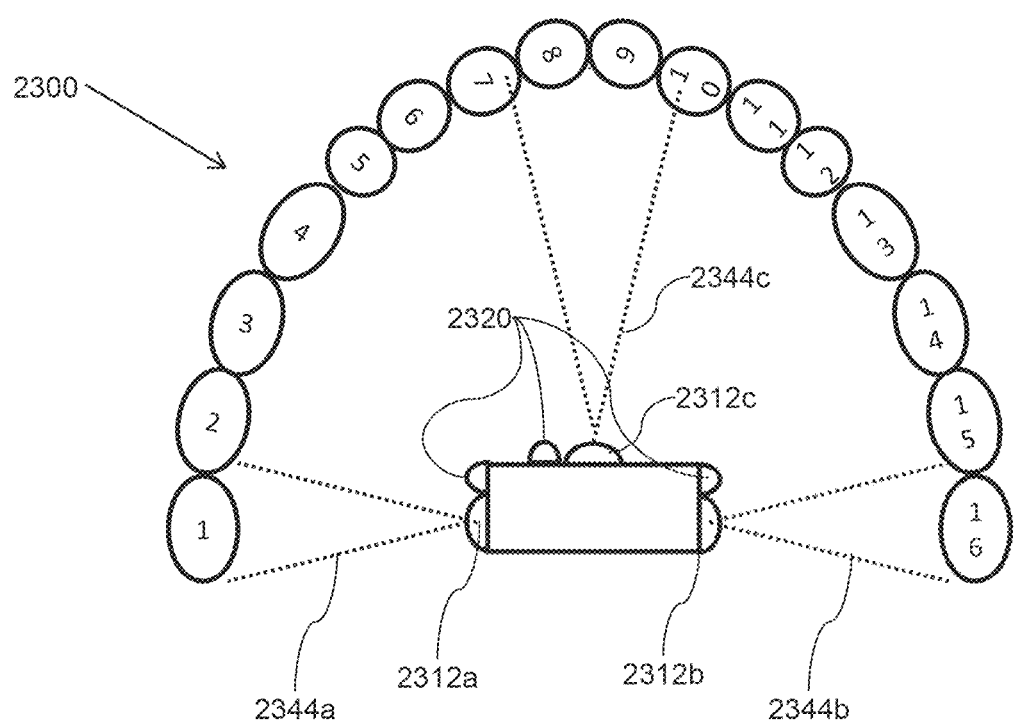

In some embodiments, projector 3221 is positioned at a distance from other device imagers and/or projectors (e.g. including one or more feature as described and/or illustrated regarding elements 3220f FIG. 32A and element 3220g FIG. 23B). A potential advantage being higher accuracy measurements associated with the large baseline between projector 3221 and the imagers (e.g. imager/s 3205, 3203).

In some embodiments, FOV of projector 3221 is tilted towards a distal end of the scanner (e.g. towards one or more imager e.g. imagers 3203 and 3205, e.g. as illustrated in FIG. 32C). A potential advantage being that projected light from projector 3221, in some embodiments, is captured in FOV of one or more of imagers 3203 and 3205.

In some embodiments, IOS 3201 includes a probe 3227. Where, in some embodiments, probe 3227 is an elongated element which extends in a direction of FOVs of imagers 3203, 3205 and/or a direction of FOVs of projectors 3209, 3211, 3213, 3215.

In some embodiments, an IOS includes at least two projector-camera pairs for which the FOVs are directed in a same direction (e.g. downwards e.g. perpendicular to a long axis of the IOS e.g. perpendicular to a distal/proximal axis of the IOS). In some embodiments, the projector-camera pairs do not have overlapping FOVs. For example, in some embodiments, an additional imager (not illustrated) is located in proximity to projector 3221. In some embodiments, the additional imager provides imaging (e.g. along with projector 3221) of dental object/s from a different angle to that of imagers 3203, 3205. For example, where imagers 3203, 3205 are positioned directly above dental objects (e.g. teeth), in some embodiments the additional imager captures images of a side view of the dental objects, optionally from a greater distance than that collected by imagers 3203, 3205. In some embodiments, the additional imager image/s are used to correct measurements (e.g. accumulated error/s) collected by imagers 3203, 3205.

Exemplary Timing

In some embodiments, the timing of frame capture of multiple imagers is coordinated. For example, frame capture may be staggered. For example, staggered and/or interleaved frame capture increase the effective frame rate. Optionally this may lead to higher rate sampling of the probe location (i.e. each imager is read at a different time period using the same FPS rate where the frame rate of the CMOS in Frames per second may range for example between 5 to 200 and/or between 200 to 500). For example, by interleaving an array of n sensors, the effective frame rate of the array may range between 1.1 times the frame rate of an individual sensor to the n times the frame rate of an individual sensor where n is the number of imagers.

Figure 33:
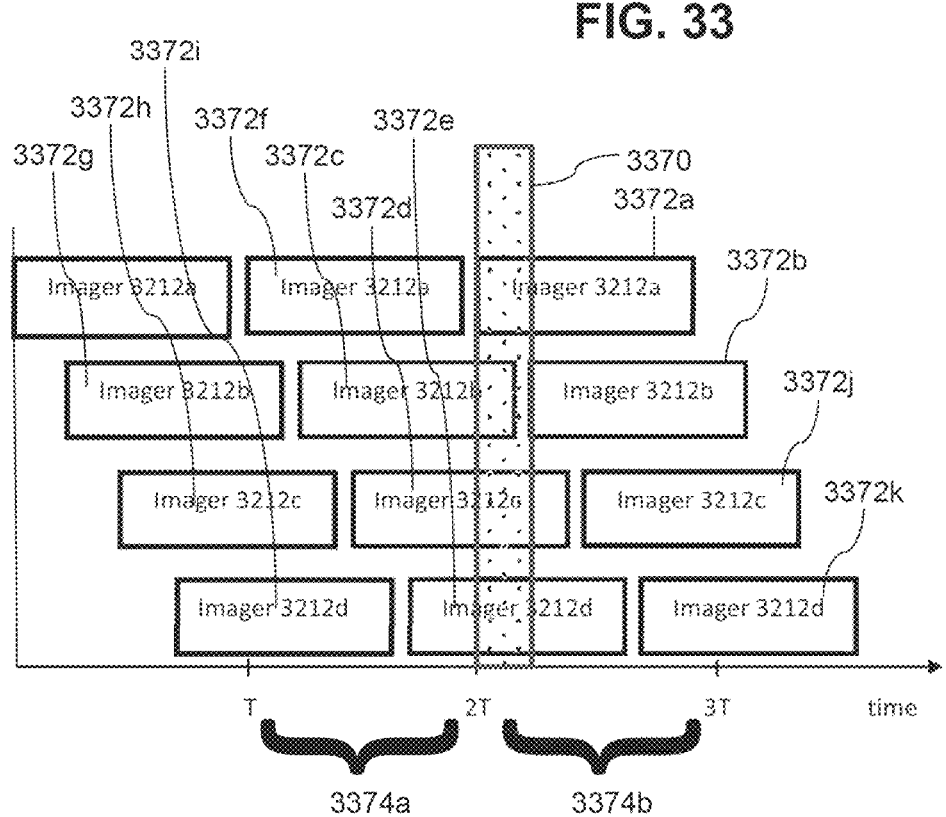
FIGS. 33 to 36 are time line diagrams illustrating interleaving of optical modules in accordance with an embodiment of the current disclosure.

FIG. 33 is a time line illustration of a frame integration of an array of four imagers in accordance with an embodiment of the current disclosure. The horizontal axis is the time, T is the period of a single frame (i.e. T=1/FPS). In some embodiments, the different imagers are read at different times over each readout period T. Optionally the location of the IOS head in the 3D model, which is obtained using the relative location (e.g. in 6 Degrees Of Freedom) of the IOS to the scanned oral features is updated at a rate that is faster than the FPS of an individual sensor. For example, the IOS location may be updated at a rate up to 4 times the FPS of an individual sensor. In some embodiments the effective frame rate of the array of 4 sensors is 4 times more than an image timing scheme, in which all the imagers are read together.

In some embodiments, movement of an IOS may be unsteady. For example, the device may be moved quickly for a short time and then be held steady and or move slowly. In a case where all of the imagers capture images simultaneously, a burst of movement may destroy (e.g. smear) all of the images of all of the sensors for the entire time interval. In some embodiments, when the imagers sampling is interleaved, for example as in FIG. 33, a burst of movement may smear some of the images in a time interval and not affect others. For example, a fast movement 3370 happened during the time between the start of an integration period 3372a of imager 3212a and the start of integration period 3372b of imager 3212b. In some embodiments, images from imagers 3212a, 3212b, 3212c and 3212d from periods 3372a, 3372c, 3372d and 3372e will be affected by the movement and/or may be discarded. Optionally, there still remains in the second time interval 3374a images from imagers 3212a, 3212b, 3212c and 3212d from periods 3372f, 3372g, 3372h and 3372i and/or there still remain in the 3rd time interval 3374b images from imagers 3212b, 3212c and 3212d from periods 3372b, 3372j and 3372k. The time break without an image is only between the end of time period 3372f of imager 3212a and the beginning of time period 3372b of imager 3212b which is less than T. In some embodiments, the sensors may be grouped activated in larger groups, for example 3 at a time or 4 at a time. Optionally, the effective frame rate of an array of n sensors activated in groups of m at a time may range between 1.2*FPS to n/m*FPS (where FPS is the frame rate of a single sensor).

Figure 34:
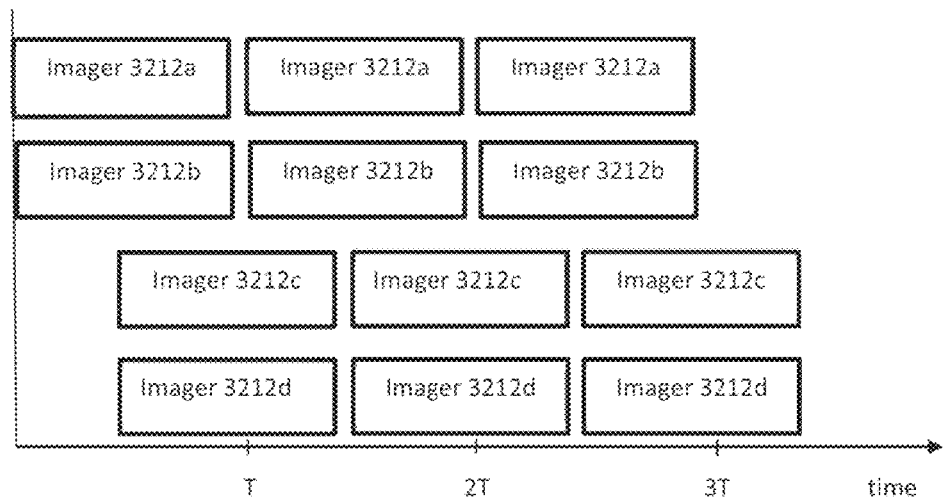

In some embodiments, imagers may be activated in pairs. For example, as illustrated in FIG. 34, pairs of imagers may be activated together. Optionally, pairs of imagers activated together will allow 3D imaging by stereoscopic methods between imagers that are activated simultaneously. Alternatively or additionally, a pair of imagers may have non-continuous FOVs that have a known spatial relationship. For example, the pair may be sampled simultaneously to compute a measurement over a long distance between the non-contiguous FOVs. Pairs of imagers that are activated together may be selected in order to achieve a goal in the imaging. For example, when imaging an object 3200 beside head 3250 of the IOS of FIGS. 32A-B, imager 3212a may be activated simultaneous to imager 3212b and/or imager 3212c may be activated simultaneous to imager 3212d to improve stereoscopic depth (where the difference between the locations of the sensors is perpendicular to the line pattern of the projector and/or where the sensors that are activated simultaneously see similar features of the surface and/or where the line of sight at the midpoint between the pair of sensors to the feature being imaged is more nearly perpendicular to the baseline offset between the imagers of the pair). Optionally, during the entire imaging period, projector 3220d may be activated. Alternatively or additionally, during the entire imaging period, projector 3220c may be activated. Alternatively or additionally, projectors 3220d and 3220c may be switched over various time intervals. For example, projector 3220d may be activated with imagers 3212a and/or 3212b and projector 3220c with imagers 3212c and 3212d.

Optionally the interleaving may be adjusted so that an imager integration period does not overlap a time when projectors are switched. For example, by interleaving pairs of n imagers, an effective frame rate of the array may be n/2 times the frame rate of an individual sensor. In some embodiments, the sensors may be grouped activated in larger groups, for example 3 at a time or 4 at a time. Optionally, the effective frame rate of an array of n sensors activated in groups of m at a time may range between 1.2*FPS to FPS n/m*FPS (where FPS is the frame rate of a single sensor).

In some embodiments, a pairs of imagers and/or an imager and projector pair may create its own depth map in every frame. Optionally each pair (including some or all of the optical modules) creates a depth map in all or some time frames. Optionally, a 3D model is created from those depth maps in every frame or in some time frames.

Optionally, the 3D model becomes more precise with the integration of more depth maps into the 3D model, for example using the next frame's depth maps.

Figure 35:
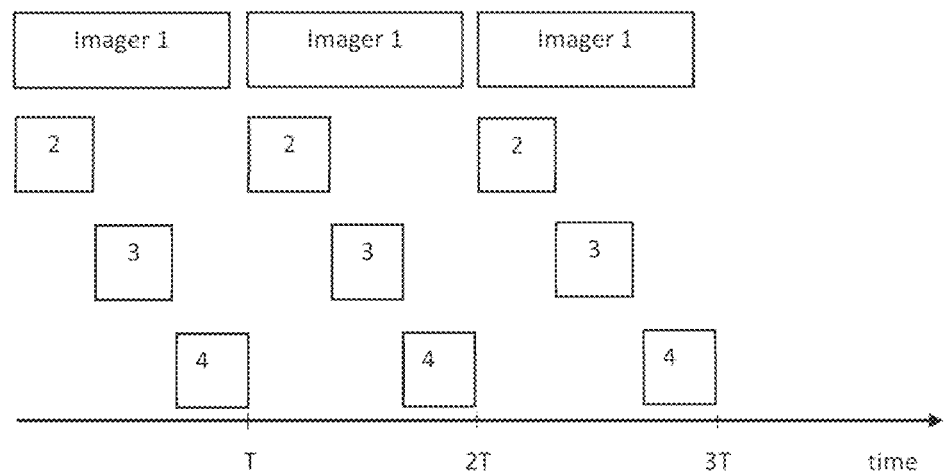

FIG. 35 illustrates a time line of an IOS having an imager (imager 1) with a long integration time and three imagers (e.g. 1, 2, 3) with short integration time in accordance with an embodiment of the current disclosure. In some embodiments, an imager with a long integration period is used to capture the precise geometry of the pattern on a tooth. Optionally, an imager with a short integration time is used to capture the position of the IOS head in accordance with an embodiment of the current disclosure. For example, the imager with the short integration time may not need as high resolution and/or signal to noise ration SNR as the imager with the long integration time. The high resolution and/or SNR may be desirable to achieve a highly accurate 3D model of a tooth. The interleaved frame rate may give a better time interpolation of movement that a traditional scanner where the sampling of location is only once in a time period. The short integration period of the short integration period scanners may help prevent image smear due to movement. The imager used to capture the position of the probe optionally images features on the tooth and/or the structured light pattern on the tooth and/or other navigation features (for example recognizable features in the oral cavity). Optionally, there may be a plurality of imagers imaging the tooth and/or a plurality of imagers used to capture the position of the probe. Optionally there may be a plurality of imagers with long integration times. Optionally there may be more than two different kinds of scanners and/or more than two types of imagers. For example, there may be more than two different integration times. Optionally, the imager that captures the pattern on the tooth is also used to capture the position of the probe. Alternatively or additionally, an imager with the short integration time may have enough SNR even in short integration time for mapping features of a ROI.

In some embodiments, a ROI is scanned and/or a position of the scanner is determined during the exposure time of a Frames [0, T] and [T, 2T] of imager #1. The position of the scanner is optionally estimated between the positions in frame [0, T] and [T, 2T] using interpolation. Alternatively or additionally a new position for the position scanner is calculated using imagers #2, 3, 4 at intermediate times.

Figure 36:
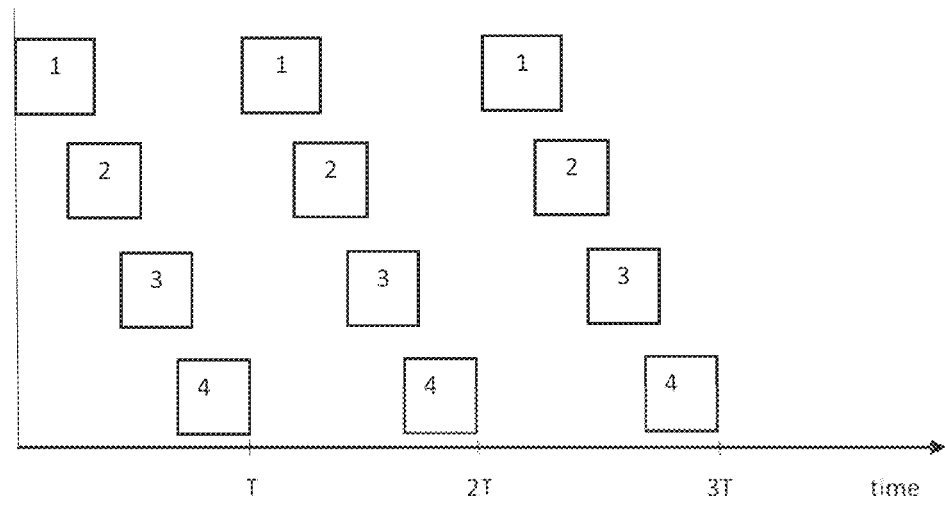

In some embodiments, the exposure time is reduced. For example, where the movements of the IOS is faster, to prevent image smear as the timing diagram shown in FIG. 36 illustrates, the integration time is 3 times shorter than in FIG. 33. In order to keep a high image signal to noise ratio (SNR) with the shorter integration time of the imager, the projectors and/or other illumination power may be increased.

Alternatively or additionally, to keep a high image SNR an imager SNR may be increased.

Exemplary Compound FOV

FIGS. 23A, 23B, 24 and 25 are schematic illustrations of an IOS configured to produce a compound FOV image in accordance with an embodiment of the current disclosure. Optionally, the FOV of the IOS covers locations that are distant from each other. For example, the FOV instead of being concentrated around one location (for example a circular FOV concentration around a central spot) the FOV is shaped to include relatively distant points. For example, the FOV of the scanner may cover an area between 10 to 300 mm2 and/or between 300 to 1000 mm2 and include points whose relative location range between 20 to 60 mm apart. Optionally the FOV will include non-continuous areas with a known geometric relationship. For example, the compound FOV scanner may measure accurately a spatial relationship between two far away points.

In some embodiments, it is important to know precise locations on multiple scales. For example, it may be important to know details of individual teeth on a small scale and/or the precise relative locations of teeth with respect to each other on a much longer scale. For example, due to pixel limitations, the required detail on the small scale may be achieved in small FOV image of tooth. In some cases, stitching the small scale images into a 3D large scale model introduces cumulative errors on the larger scale. For example, in some embodiments a single depth mapped image will including teeth from opposite sides of a dental arch will be made. The single depth mapped image may give an improved accuracy of calculations of the relative position of the ends of the arch. The large scale measurements of the rest of the arch are optionally conditioned on the measurement of other large scale features, increasing the precision thereof.

Alternatively or additionally, multitooth and/or compound FOV images may be made of different sets of teeth (not just 2 ends of arch). For example, #2 and #15, #3, 14 etc. or #6 and #12 (third and 2 thirds of the arch). In some embodiments, more than one image can be taken of distant objects. For example, images may be made of the same teeth from different positions and heights. Different angles can be done to capture the side of the teeth or the upper surface or both. The locations of other features may be conditioned on these features and/or the stitched map of the small FOV images.

In some embodiments, it may be desired to place a bridge over a few teeth and/or over one or more implants located a few cm apart. In some embodiments, an implant may have a very low flexibility and/or to fit the bridge to an implant may require very precise data on the shape and position of the implants. In some embodiments the position of an implant may be measured using by replacing a prosthetic tooth with a measuring abutment. Alternatively or additionally, using a scanner in accordance with the current disclosure a prosthetic tooth and/or an implant may be measured without an abutment. Precise data may also be needed in some embodiments to achieve proper closure of the top and bottom of the mouth and/or to fit a prosthetic between teeth and/or implants. Optionally, a single image is made with a FOV that includes objects on both ends of the bridge and/or along the path of the bridge. For example, two small FOV images, including a high resolution image of a portion of multiple features along the path for example one or more implants may be made. Optionally, the spatial relationship between the FOVs may be known to a high precision such that the precise spatial relationship between the features may be computed. For example, the precision of the relative positions of the features may be known to between 0.01 to 0.03 mm and/or between 0.03 mm to 0.1 mm.

FIG. 23A illustrates a IOS scanner with a compound FOV making high a resolution image of teeth #1 and #16 at opposites ends of a dental arch 2300. Optionally, small FOV hi resolution images of the dental arch allow a processor to produce a 3D model of the arch with high local resolution (for example with an error of less than 0.01 mm and/or between 0.01 to 0.05 mm and/or between 0.05 to 0.1 mm. By stitching together the small FOV errors, the processor may produce a model of the entire arch with a cumulative error that is between 5 to 50 times the local error). For example, the error across the full dental arch may range between 1.0 to 0.7 mm and/or between 0.7 to 0.3 mm and/or between 0.3 to 0.1 mm. Optionally a compound FOV image is made including images of distant location at high relative precision. The high precision relative positions may be added to a 3D map. Adding the large scale measurement optionally increases the accuracy of the entire map.

In some embodiments, an IOS head 2350 includes opposing side facing imager sets 2312a and 2312b and/or projectors 2320. For example, the compound field of view may include a subfield 2334a with includes a portion of tooth #1 and/or a separate subfield 2334b that includes a portion of tooth #16. The relationship between the subfield's 2334a and 2334b may be known to a high precision. A single depth mapped image including both tooth #1 and #16 may be produced with a spatial error of for example less than 10 µm and between 10 to 30 µm and/or between 30 to 100 µm.

Optionally, using the known precise positions of teeth #1 and #16, the model of the entire dental arch may be improved to have a spatial error less than 10 µm and between 10 to 30 µm and/or between 30 to 100 µm. For example, the cumulative error over the dental arch may be reduced from 5 to 20 times and/or from 2 to 4 times.

FIG. 23B shows a compound FOV IOS scanner with an extra imager module 2312c and/or projector 2320. For example, the extra FOV 2344c of imager 2312c may be used to improve knowledge of the pose of the imagers 2312a, 2312b and/or 2312c during imaging. This may leaded to higher precision in the large scale map of the IOS.

Figure 25:
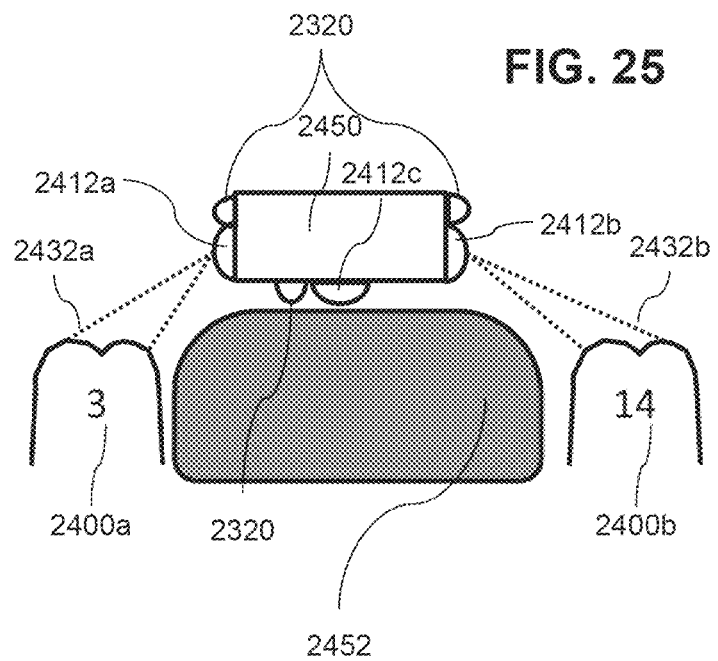

In some embodiments, the two side viewing imagers 2312a and 2312b may be used for the large scale and/or compound FOV scanning. Alternatively or additionally, the system may not include the 3rd imager 2312c and/or an imager may point downward into the page, for example as illustrated in FIG. 25. Alternatively or additionally the third imager 2312b may be used in local small FOV mapping. Alternatively or additionally, the scanner may be used to scan the mouth simultaneously at a large and small scale using multiple imagers and/or projectors. Alternatively or additionally, multiple imagers may be used to scan a large area of the mouth while keeping precise track of the location of the scanning head 2350. In some embodiments, the third imager 2312c may be a standard IOS imager. Optionally a handle 2003 of the IOS is optionally connected to head 2350 for example as shown in FIG. 23A. Optionally, the handle over lies imager 2312c. The handle 2003 is not shown in FIG. 23B.

Figure 24:
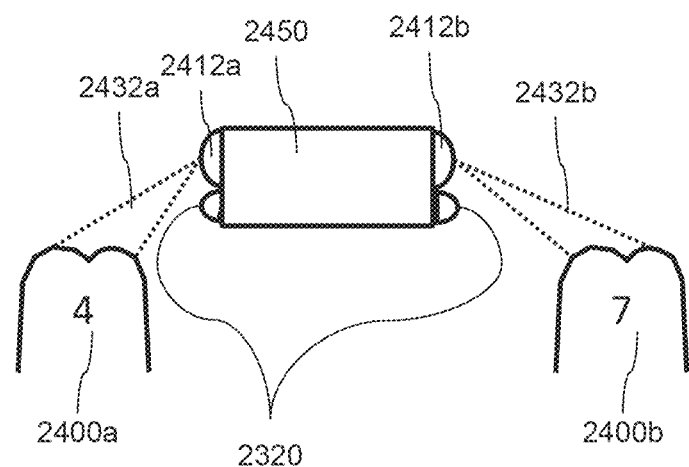

FIGS. 24 and 25 illustrate an alternative geometry for scanning a compound FOV in accordance with an embodiment of the current disclosure. Optionally, the compound FOV may include non-continuous subfields (for example subfields 2432a and 2432b).

Optionally multiple imagers may be angled with respect to each other. For example, the subfields 2432a and 2432b may be at less than 180 degrees to each other and/or the subfields 2432a and 2432b may be directed not in the same plane.

FIG. 24 illustrates an IOS scanner for scanning a non-continuous compound FOV in accordance with an embodiment of the current disclosure. Optionally, multiple imagers 2412a and 2412b may image a compound FOV made of subfield 2432a and subfield 2432b respectfully. Optionally subfield 2432a and subfield 2432b are not in the same plane. In the exemplary embodiment imagers 2432a and 2432b are imaging two teeth on the same side of a dental arch. For example, subfield 2432a includes a portion of tooth #4 and subfield 2432b includes a portion of tooth #7. For example, imaging two teeth on one side of a dental arch may be useful for fitting a bridge between the teeth. In some embodiments, it may be useful when subfields 2432a and 2432b are not in a single plane. For example, non-planar subfields 2432a and 2432b allow simultaneous imaging of teeth #4 and #7 when an obstacle between teeth #4 and #7 may makes it difficult to fit the scanner head 2450 in the space between the teeth.

FIG. 25 illustrates a compound FOV IOS scanner in accordance with an embodiment of the current disclosure. For example, when scanning a mandibular arch a tongue 2452 may block a region between teeth on opposite sides of the arch.

Optionally FOVs 2432a and 2432b are outside of a plane and/or allow scanning of opposite sides of the arch (e.g. teeth #3 and #14) without requiring positioning of head 2450 between the teeth. Optionally, head 2450 may include a third imager 2412c.

Alternatively or additionally, head 2450 may include only two imagers 2412a and 2412b and/or head 2450 may include more than three imager sets. Optionally IOS can be used for pressing the tongue down and clear FOV obstructions.

Exemplary IOS Attachment for Exemplary Compound FOV

Figure 31:
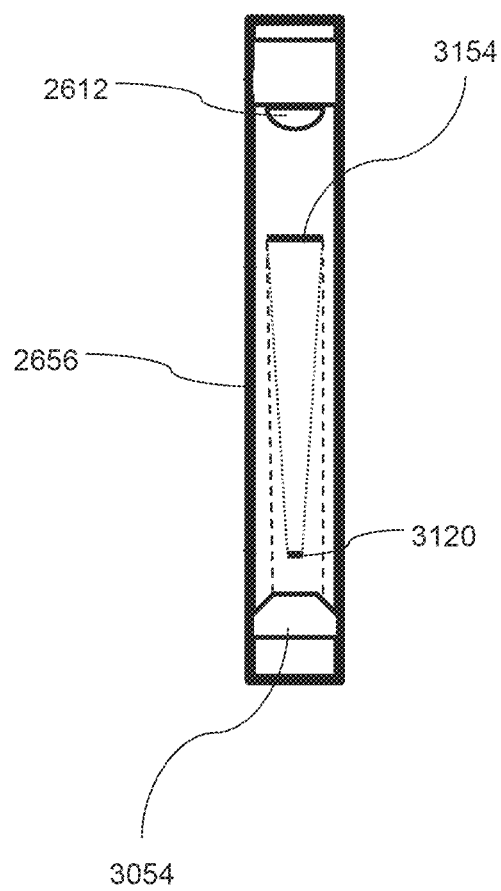

FIGS. 26A-B to 31 are schematic illustrations of IOS scanners including attachments for scanning a compound FOV in accordance with embodiments of the current disclosure. For example, an attachment may split a FOV of a scanner to multiple subfields in accordance. For example, a conventional scanner may be configured to capture a simple and/or concentrated FOV. Optionally the attachment may facilitate capturing a compound FOV (for example as described above in relation to FIGS. 23A, 23B, 24 and/or 25) with the conventional scanner. The conventional scanner with the attachment may be used to produce a multi-scale model for example as described in connection to FIGS. 22 to 25. Optionally a splitter attachment may be affixed to a head of a scanner (for example an attachment may be affixed to a fixed scanning head scanner such as the Condor scanner by Condor Zuiderlaan 1-3, 9000 Gent, Belgium and/or the True definition scanner by 3M Center St. Paul, Minn. 55144 and/or the Aadva IOS scanner by GC Interleuvenlaan 33, 3001 Leuven, Belgium). Alternatively or additionally, a splitter attachment may replace a removable scanning head (for example the mirror sleeve of the CEREC Omnicam scanner by Sirona, Susquehanna Commerce Center, 221 W. Philadelphia Street, Suite 60W, York, Pa. 17401 USA and/or TRIOS 3 scanner by 3Shape A/S, Holmens Kanal 7, 1060 Copenhagen, Denmark and/or CS3600 scanner by Carestream and/or the Emerald scanner by Planmeca USA, Inc., 100 North Gary Avenue, Suite A, Roselle, Ill. 60172 and/or the disposable sleeve of a Carestream 150 Verona Street, Rochester, N.Y. 14608, USA). Alternatively or additionally, a splitter attachment may be affixed to an arced scanning head. For example, where, in some embodiments, a splitter attachment is fixed to a scanner such as DWOS by Dental Wings 2251 Letourneux, Montreal (Quebec) H1V 2N9, Canada. For example, the splitter illustrated in FIG. 39B which, in some embodiments, is attached to the scanner illustrated in FIG. 39A.

FIG. 26A is a schematic side view illustration of an IOS scanner with an attachable FOV splitter in accordance with an embodiment of the current disclosure. For example, a mount 2656 holds a splitter 2654 (for example a mirror and/or a prism) in a FOV 2034a of the IOS. In some embodiments, the splitter includes a curved mirror, potentially providing a wider FOV.

FIG. 26B is a schematic head-on view illustration of an IOS scanner with an attachable FOV splitter in accordance with an embodiment of the current disclosure. Splitter 2654 optionally splits FOV 2034a of a scanner including a FOV or imager 2012a and/or a projected pattern of pattern projector 2020a into a compound FOV with two subfields 2634b and 2634c. For example, subfields 2634b and 2634c may be focused on teeth #3 and #14 on opposite sides of a dental arch. Optionally, the system is calibrated to allow determination of surface features on teeth #3 and/or #14 and/or a relative position of the teeth from a compound depth mapped image including both subfields 2634b and 2634c. Optionally, with the attachment, an image produced by sensor 2012a will include images of the subfields 2634a, 2634b (e.g. in the example of FIG. 26B teeth 3 and 14). Optionally, the subfields may not be continuous. Optionally, a processor is programmed to compute the relative location of objects in one subfield 2634b, 2634c in respect to an object in one the other subfield 2634b, 2634c from the compound image. Optionally, the computation of relative location may depend of calibration data (for example as described herein below).

In some embodiments of an IOS, an imager is directed at an angle to an axis of a handle 2003. For example, imager 2012a is directed substantially perpendicular to the axis of handle 2003. Optionally, mount 2656 hold splitter 2654 away from handle 2003. For example, mount 2656 may be mounted to handle 2003. For example, mount 2656 may hang parallel to the direction of focus of imager 2012a. Alternatively or additionally, imager 2012a may be directed at a different angle to the axis of handle 2003. Alternatively or additionally, mount 2656 may be directed at a different angle to the axis of handle 2003. Optionally, mount 2656 holds splitter 2654 in the FOV 2034a of the scanner whether the angle of the focal direction of imager 2012a be the same as that of mount 2656 and/or whether the angles differ. For example, if the angles differ, mount 2656 may be connected to handle 2003 at a location different from imager 2012a. In some embodiments, a splitter may split the FOV 2034a into two parallel subfields (e.g. 2634a and 2634b which for example are coaxial but in opposite directions). Alternatively or additionally a splitter may split the FOV into non-parallel subfields and/or subfields that are not coplanar (for example as illustrated in FIGS. 27A-C).

Figure 27A:
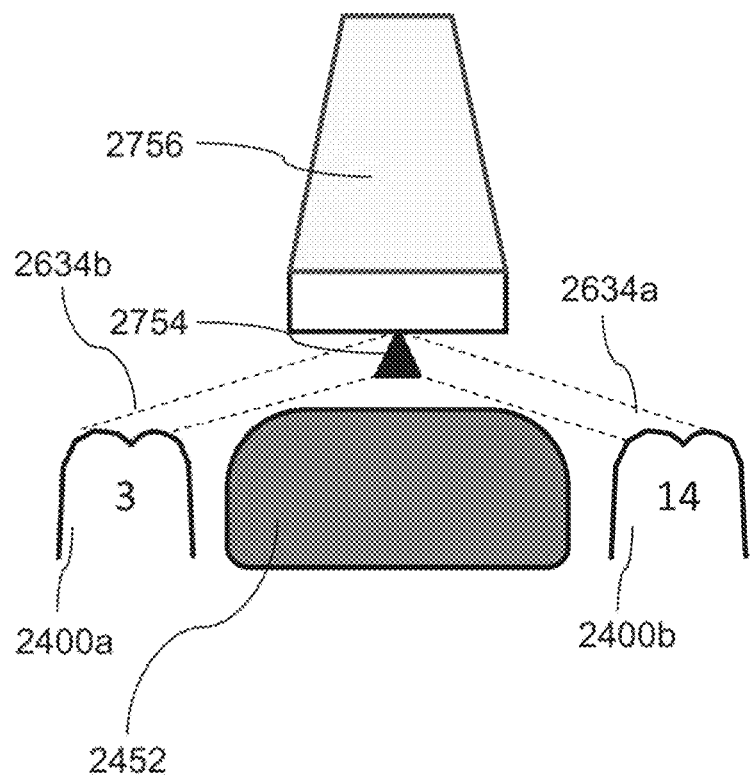

FIG. 27A illustrates an alternative mount and/or splitter. For example, in some embodiments, an imager may be directed along an axis of handle of the IOS. Optionally a mount 2756 is axially mounted to handle. For example, the mount 2756 may include a sleeve that slide over the handle and or head of the IOS.

Figure 27B:
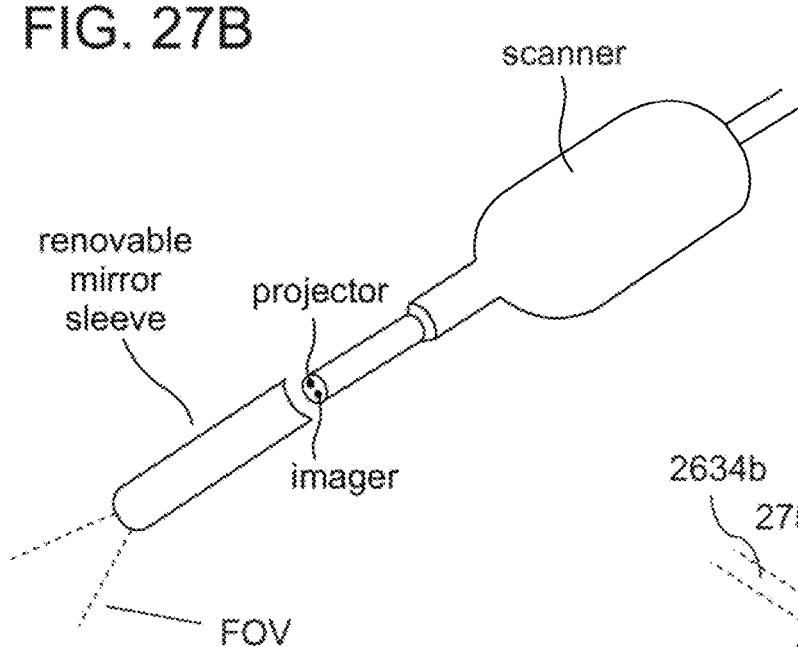

FIG. 27B illustrates a removable sleeve scanning system (for example similar to the CEREC Omnicam scanner by Sirona, Susquehanna Commerce Center, 221 W. Philadelphia Street, Suite 60W, York, Pa. 17401 USA).

Figure 27C:
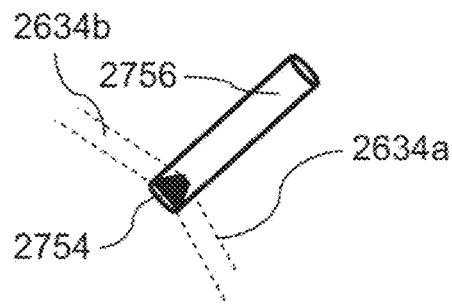

FIG. 27C illustrates a FOV splitter sleeve in accordance with an embodiment of the current disclosure. For example, sleeve 2756 may fit the scanner of FIG. 27B in place of the standard mirror sleeve. Optionally replacing the mirror sleeve would convert the scanner into a compound FOV scanner as illustrated for example if FIG. 27A. Optionally, splitter 2754 may be rotated 90 degrees (such that subfields 2634a and 2634b are directed up and down). Rotating splitter 2754 may make it easier to direct the FOV of the projector and imager of the scanner of FIG. 27B to the same FOV. For example, in such a case, a dentist may twist the scanner to get a compound view of two sides of a dental arch. Optionally splitter 2754 may be a simple FOV splitter. In some embodiments, splitter 2754 includes one or more curved element (e.g. a curved mirror) potentially enlarging the FOV reflected by the mirror.

Alternatively or additionally, splitter 2754 may include a calibration area, for example as explained with regard to FIGS. 29A-31.

Exemplary Multiple FOV Attachments

Figure 37A:
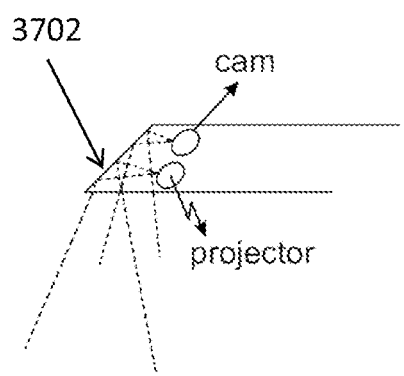
FIGS. 37A-C, 38A-C to 39A are schematic illustrations of attachments for various forms of IOS's in accordance with embodiments of the current disclosure.

FIG. 37A is a side view schematic illustration of an IOS with a fixed head in accordance with an embodiment of the current disclosure. In this figure an exemplary scanner is composed from an imager ("cam" in FIG. 37A) and a projector that are one above the other and a mirror 3702 to transform the FOV from looking forward to looking down (see dashed lines of FIG. 37A).

Figure 37B:
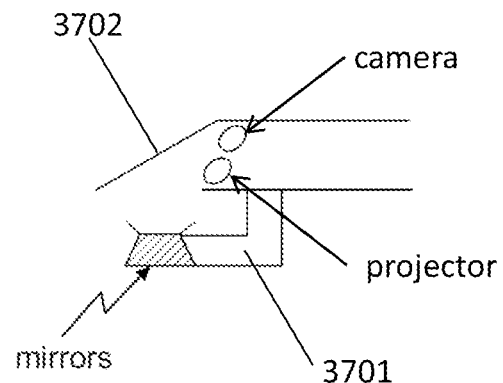

FIG. 37B is a side view schematic illustration of a FOV splitting attachment 3701 to an IOS with a fixed head in accordance with an embodiment of the current disclosure. In some embodiments, the IOS with a fixed head is the IOS of FIG. 37A. In FIG. 37B an attachment 3701 is connected to the bottom of the scanner in accordance with embodiment of the current disclosure. In some embodiments, the attachment splits both the FOV of the camera and that of the projector e.g. in two different directions. For example, sideways e.g. including one or more feature as illustrated and/or described regarding one or more of splitter 2654 FIGS. 26A-B, 2754 FIGS. 27A-C, 2654 FIG. 28, 2954 FIGS. 29A-B, 3054 FIG. 30, 3054 FIG. 31.

In some embodiments, the splitting attachment of FIG. 37B (and/or splitter FIGS. 26A-B, 2754 FIGS. 27A-C, 2654 FIG. 28, 2954 FIGS. 29A-B, 3054 FIG. 30, 3054 FIG. 31) includes one or more curved element (e.g. a curved mirror) potentially enlarging the FOV reflected by the mirror.

Figure 37C:
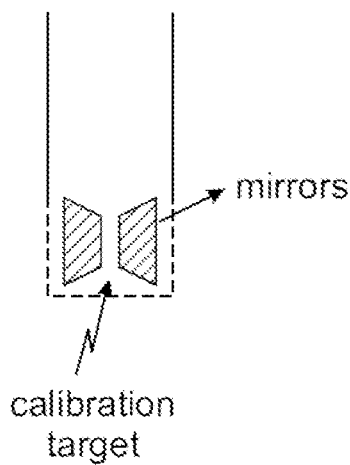

FIG. 37C is a top view schematic illustration of a FOV splitting attachment to an IOS with a fixed head in accordance with an embodiment of the current disclosure. In some embodiments, shaded areas of FIG. 37C each indicate a mirror. In this figure an exemplary attachment also includes a calibration target to calibrate the scanner while imaging the teeth. For example, in some embodiments, FIG. 37C illustrates a top view of the IOS of FIG. 37B further including a calibration target.

Figure 38A:

FIG. 38A is a side view schematic illustration of an IOS with a fixed head in accordance with an embodiment of the current disclosure. In this figure an exemplary scanner is composed from two imagers that are side by side with FOVs looking down. Where an imager is indicated with a circle.

Figure 38B:
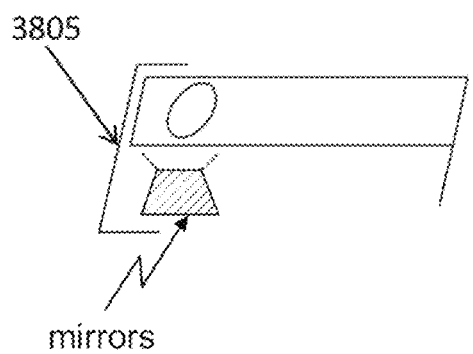

FIG. 38B is a side view schematic illustration of a FOV splitting attachment to an IOS with a fixed head in accordance with an embodiment of the current disclosure. Where the IOS with a fixed head is, in some embodiments, as illustrated and/or described regarding FIG. 38A. In this figure an exemplary attachment 3805 is connected to the front of the scanner. In some embodiments, attachment 3805 includes one or more mirror.

Figure 38C:
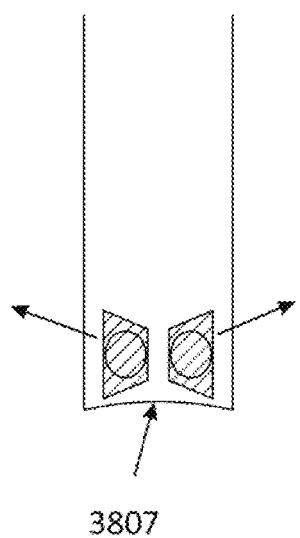

FIG. 38C is a top view schematic illustration of a FOV splitting attachment to an IOS with a fixed head in accordance with an embodiment of the current disclosure. In this figure an exemplary attachment also includes a calibration target 3807 to calibrate the scanner while imaging the teeth. In some embodiments, mirrors are indicated by shaded areas. In some embodiments, imagers are indicated by circular elements.

Figure 39A:
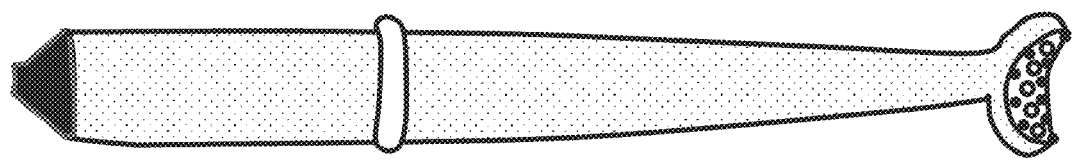

FIG. 39A is a side view schematic illustration of an IOS with an arch head in accordance with an embodiment of the current disclosure.

Figure 39B:
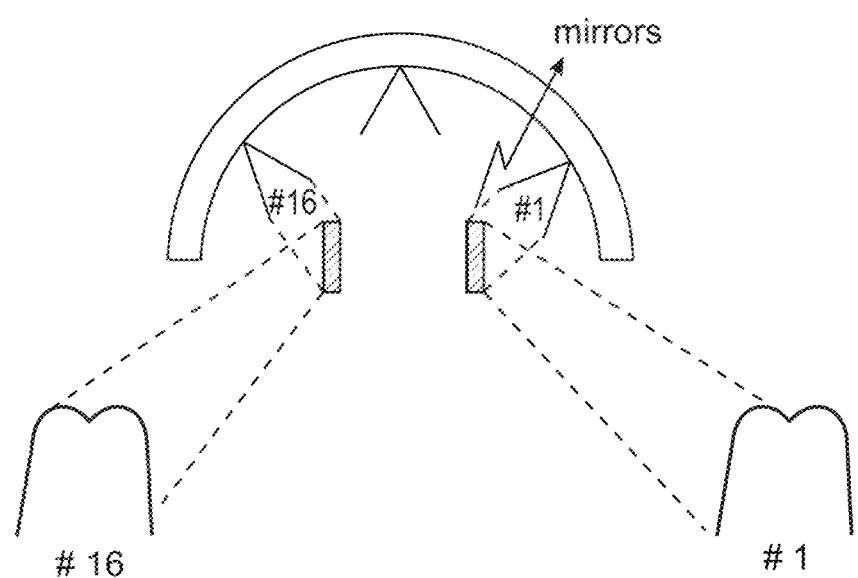
FIG. 39B is a front end view schematic illustration of an FOV splitting attachment on an arch head in accordance with an embodiment of the current disclosure.

FIG. 39B is a front end view schematic illustration of an FOV splitting attachment on an arch head in accordance with an embodiment of the current disclosure.

Exemplary Calibration of an Exemplary Compound FOV Attachment

FIGS. 28 to 31 illustrate methods of calibrating compound field of view attachments in accordance with embodiments of the present disclosure. For example, calibration may facilitate precise calculation of the distance between points in different subfields of a compound field of view. In some embodiments, calibration is performed once or a few times (for example at the begging and/or end of a scan and/or periodically). For example, a connection between the IOS and the attachment may be stable and/or the calibration substantially unchanging. Alternatively or additionally, calibration may be performed online (for example during scanning, constantly and/or at close intervals). For example, online calibration may facilitate accurate measurement in cases where the connection between the IOS and the attachment is unstable. For example, mount 2756 may replace a removable sleeve of an existing scanner.

Figure 28:
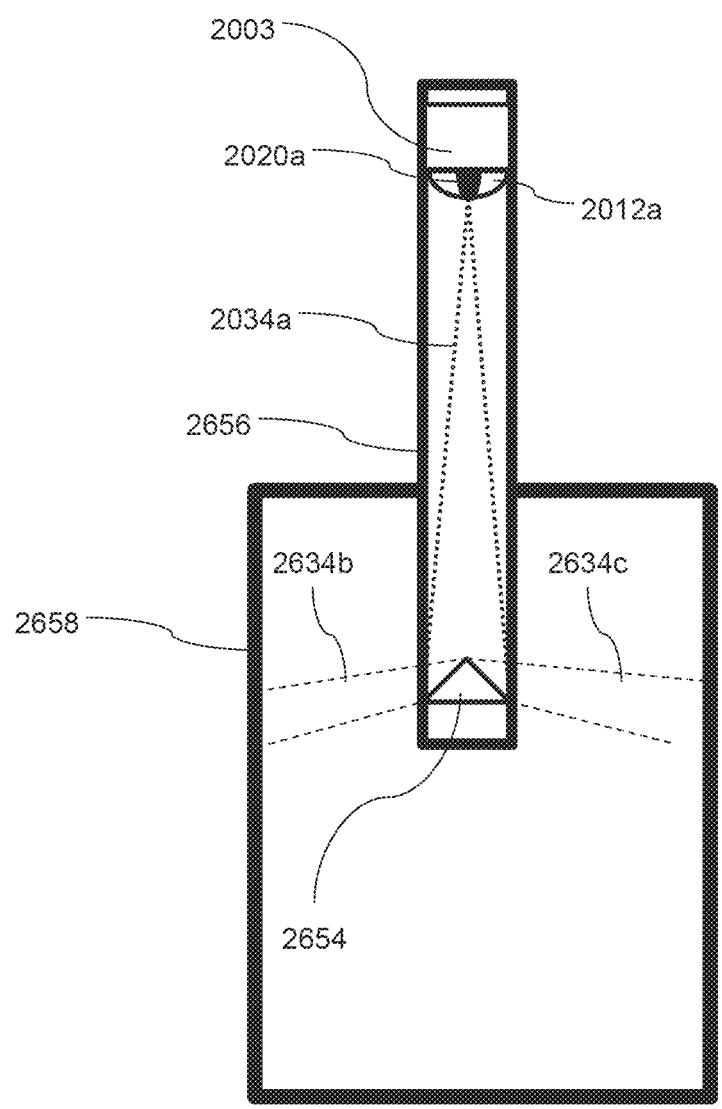

FIG. 28 is a schematic illustration of calibration of an IOS attachment using an external target. For example, an external target may take the form of a sleeve 2658 with known dimensions and/or parallel walls at a known distance. Optionally the target will include fiducial markings. Based on the known size and shape of the target and the scaling detected in subfields 2634a and 2634b the IOS with the attachment is optionally calibrated. Based on the calibration, the IOS may be used to measure distances between objects within compound FOV. For example, calibration device 2658 may include two parallel walls with three fiducial markers on each wall. Inserting the scanner between the walls allows calibrating the 6 degrees of freedom between two FOVs. In some embodiments it is not necessary to know the position of the IOS, only the relative positions of the FOVs one to another. Optionally, the target is attached to the scanner body and/or measurements of known targets are compared to measurements that were taken during the manufacturing process. The difference between the measurements is optionally used to calibrate the movement of the IOS attachment relative to the scanner body.

FIGS. 29A-31 illustrate online calibration of an IOS scanner with an attachment in accordance with an embodiment of the current disclosure. Optionally, an attachment may include a calibration area. For example, the calibration area may be including in a FOV of an imager. For example, an image may cover one or more subfields and/or the calibration are. The calibration area may include, for example, a known calibration pattern (fringe like), known sizes, known orientations, a white surface onto which a pattern is projected, multiple small markers (for example small reflective balls).

Optionally inline calibration may be used in place of calibration using an external target. Alternatively or additionally, online calibration may be used in addition to calibration on using an external target. The depth to the calibration area may be found using the depth measuring ability of the IOS. For example, the calibration area may include a diffusively reflective area that reflects a portion of a pattern projected by a projector module of the IOS. The depth to the calibration area is optionally found by reconstruction of the projected structured light. The lateral alignment and the angular alignment are optionally found from the depth of the calibration area, as well as other features and/or fiducials on the calibration area and/or elsewhere.

In some embodiments, the splitter will split a portion of the image toward the fiducial object. For example, splitter may include a reflective surface and/or the fiducial object may be distanced from the splitter and/or seen in the reflection. Optionally, the fiducial object is distanced from the splitter to adjust the focal length between the imager and the fiducial object. For example, the focal distance between the fiducial object and the imager is similar to the focal distance between the scanned object and the imager. For example, splitter 2954 includes mirrored surfaces splitting one area of FOV 2034a to a subfield 2634b and/or a second area of FOV 2034a to a second subfield 2634c and/or a third the calibration area. Optionally, when the attachment is connected to the IOS the image produced includes three subimages. For example, one subimage includes an image of subfield 2634b (e.g. in the example FIGS. 29A-B tooth #3), a second subimage includes an image of subfield 2634c (e.g. in the example FIGS. 29A-B tooth #14), a third subimage includes an image the calibration area.

In some embodiments, from the image of calibration area, a processor computes the spatial relationship (for example distance, direction and/or relative orientation) between imager 2012a and splitter. Optionally, based on the properties of imagers 2012a, the properties of splitter, and the compound image including subimages of object 2960 and subfields 2634b and 2634c the relative location and orientations of objects in the image in either or both subfields 2634b, 2634c are computed. For example, the computations may be performed by an on-board processor and/or an external processor. In some embodiments, when the attachment moves with respect to the IOS (for example because mount 2656 and/or the connection between mount 2656 and handle 2003 is not stable), the subimage of the calibration area in each image is used to correct the effect of the movement and/or compute an accurate relative location of between features visible in either or both subfields 2634b, 2634c.

In some embodiments, an external calibration is used to calibrate the location of objects based on their location in the compound image produced by IOS with the attachment for example as described in the description of FIG. 28. Optionally, a spatial relationship between objects in subsequent images is corrected based on the subimage of the calibration area. Optionally, the calibration area may be between the subfields.

Alternatively or additionally, a calibration area may appear in one of the subfields and/or elsewhere in the compound image.

FIGS. 29A and 29B illustrate an attachment with a splitter and a calibration area including a fiducial object 2960 in accordance with an embodiment of the current disclosure.

FIG. 29A illustrates an embodiment where fiducial object 2960 is directly connected to the splitter 2954 and/or is directly viewed in FOV 2634a. FIG. 29B illustrates an embodiment where splitter 2954 includes a third splitting zone (for example a spectrally reflective surface 2921) in FOV 2634a. For example, fiducial object 2960 is positioned at a distance from splitter 2954. Optionally, a reflection of object 2960 is viewed in FOV 2634*a*. For example, the distance between splitter and object 2960 can be tuned to fit the depth of focus of imager 2612*a*. Optionally object 2960 does not interrupt the line of sight between splitter 2954 and an optical module of the IOS (for example imager 2012*a* and/or projector 2020*a*). For example, object 2960 may be translated in the third dimension (e.g. into or out of the page) to avoid interrupting the line of sight. In some embodiments, the focal length to the fiducial object may be further lengthened, for example by including a set of beam folders for example as illustrated in FIG. 31.

Figure 30:
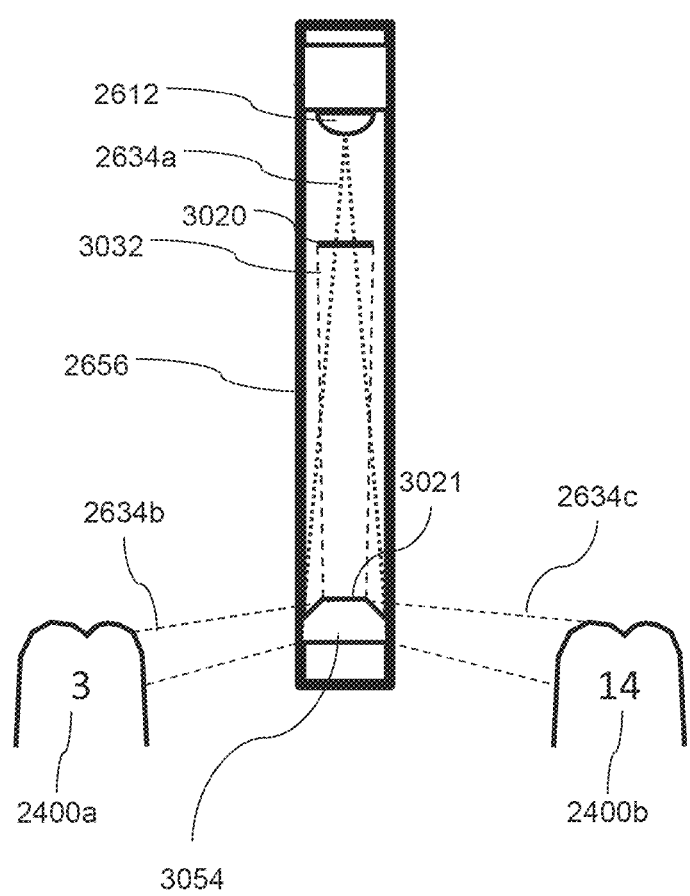

FIG. 30 illustrates an IOS attachment where the calibration area includes a diffusely reflective surface 3021 and a pattern projector 3020. The pattern projector 3020 optionally projects 3032 a pattern onto the surface 3021. From the image of the projected pattern on surface 3021, the relative distance, direction and/or orientation between imager 2612 and splitter 3054 may be computed. Optionally, projector 3020 may include the pattern projector of the IOS (for example projector 2020*a*). Projector 3020 is optionally set backward or forward (e.g. into or out of the page) for example to avoid interrupting the FOV 2634*a* between imager 2612 and splitter 3054.

FIG. 31 illustrates an IOS with a reflector to adjust a depth of focus between a calibration pattern projector and an imager in accordance with an embodiment of the current disclosure. In some embodiments, for example when the working depth of field of the IOS limited, a folding mirror 3154 is added that increases the distance to the calibration area. For example, the focal distance between the imager 2612 and calibration projector 3120 area may be similar to the distance to the measured teeth (for example as illustrated in subfields 2634*b* and 2634*c* in FIG. 30). Alternatively or additionally, the calibration pattern may be projected by the pattern projector of the IOS (e.g. projector 2020*a* of FIG. 26A) and/or a set of beam folders (for example reflectors and/or refractors for example prisms) may be supplied between the pattern projector and the splitter.

Exemplary Mirror Heating

In some embodiments, an IOS attachment (the attachment for example, including one or more feature as illustrated and/or described regarding IOS attachments and/or mounts of FIGS. 26A-B to 31) includes a mirror configured to remain fog-free. For example, when the mirror is exposed to temperature and/or humidity change/s.

In some embodiments, one or mirror of an attachment is thermally coupled to one or more heat source. For example, in some embodiments, heat is transferred from one or more IOS LED to the mirror. For example, by metal connection/s e.g. provided by a body of the IOS and/or of the attachment.

Alternatively or additionally, in some embodiments one or more heating element is thermally coupled to a mirror. In some embodiments, one or more heating element is flexible, for example, includes a Kapton® polyimide heater. In some embodiments, heating element/s are housed within the attachment.

A potential advantage of heating mirror/s is potential reduction of fogging of the mirror, for example, associated with introducing a room temperature attachment into a patient's mouth, where, in some embodiments, a heated mirror will accumulate less condensation e.g. from warm moist patient breath than, for example, a room temperature mirror.

Exemplary Measurement of Edentulous Dental Arch

Figure 43:
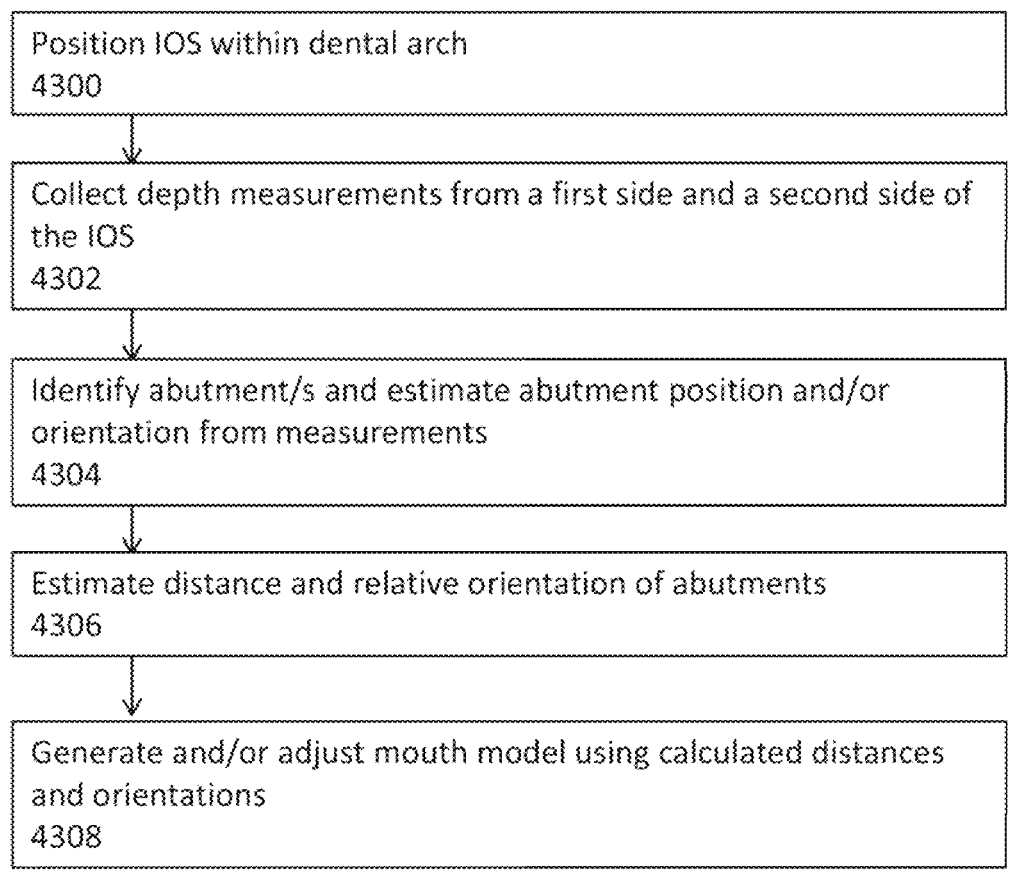
FIG. 43 is a flow chart of a method of measurement of an edentulous dental arch, according to some embodiments of the invention.

FIG. 43 is a flow chart of a method of measurement of an edentulous dental arch, according to some embodiments of the invention. In some embodiments, an "edentulous dental arch" is defined as a jaw lacking one or more tooth. In some embodiments, the method of measurement is used to collect measurements from an edentulous dental arch entirely lacking teeth.

At 4300, in some embodiments, an IOS including imaging FOVs at least on two sides of the IOS (e.g. an IOS including a compound FOV e.g. as described elsewhere in this document) is positioned such that at least a portion of a dental object (e.g. tooth and/or dental implant abutment and/or dental arch gingiva) are within at least one FOV of the IOS.

Figure 44A:
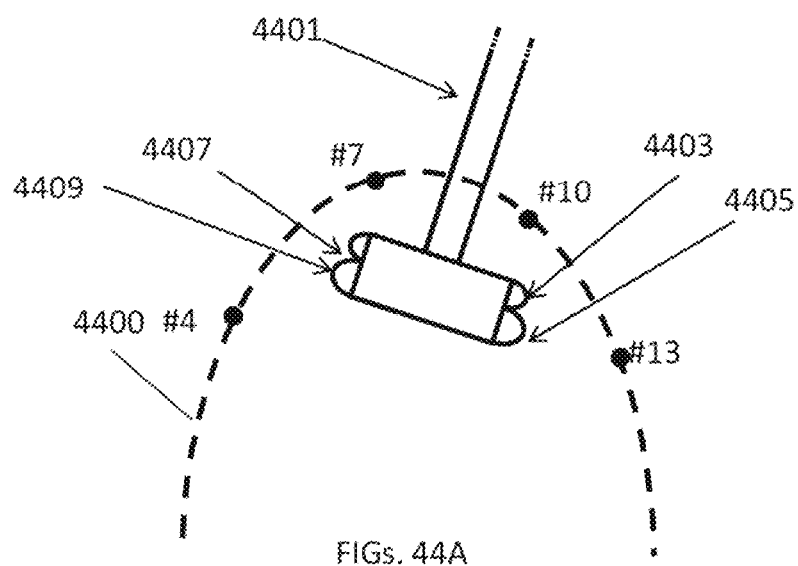
FIGS. 44A-C are schematic illustrations of measurement of an edentulous dental arch using IOSs configured to produce a compound FOV image, according to some embodiments of the invention.
Figure 44B:
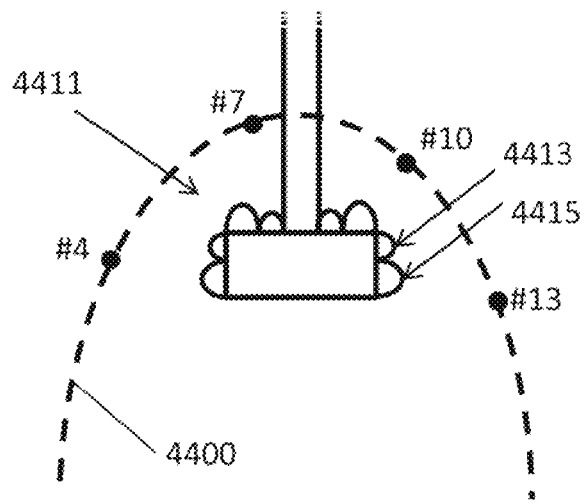
Figure 44C:
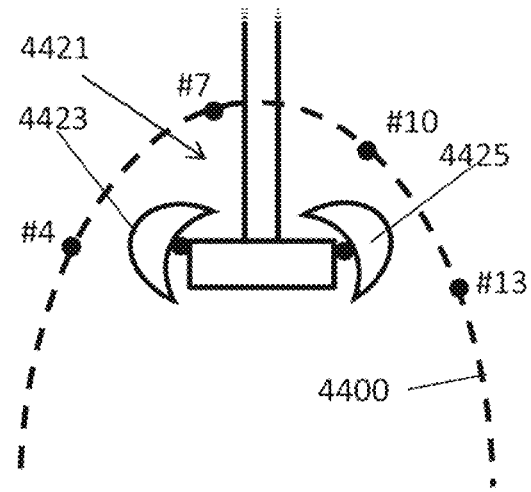

In some embodiments, the IOS is positioned within a dental arch (e.g. as illustrated in FIGS. 44A-C), for example, so that a first FOV on a first side of the IOS captures at least a portion of a first dental object and a second FOV on a second side of the IOS captures at least a portion of a second dental object, where, in some embodiments, the first and second dental objects are on opposite sides of the dental arch. In some embodiments, more than two FOVs capture two or more dental objects. For example, as illustrated in FIG. 44B where, in some embodiments, IOS 4411 includes four imager-projector pairs (e.g. pair 4413, 4415) where, in some embodiments, an FOV of each imager-projector pair captures an abutment.

In some embodiments, measurements are collected from a first pair of dental objects (object A and B), for example, a first pair of abutments. Then, in some embodiments, the IOS is moved and/or FOVs of the IOS are moved and measurements are collected from a second pair of dental objects where the second pair includes one of the dental objects of the first pair. For example, the second pair is object B and a new object C. In some embodiments, measurements of the first and second pair provide relative position and orientation between three sets of dental objects. Where, for example, spatial relationship between object pair A-C is estimated from measurements of pairs A-B and B-C. Optionally, in some embodiments, pair A-C is also measured. Potentially, the A-C estimation combined with the A-B measurement increases the accuracy estimation of object position and/or orientation. In some embodiments, the same technique is used for three pairs or four pairs or 2-10 pairs, or lower or higher or intermediate numbers or ranges of pairs.

Figure 45:
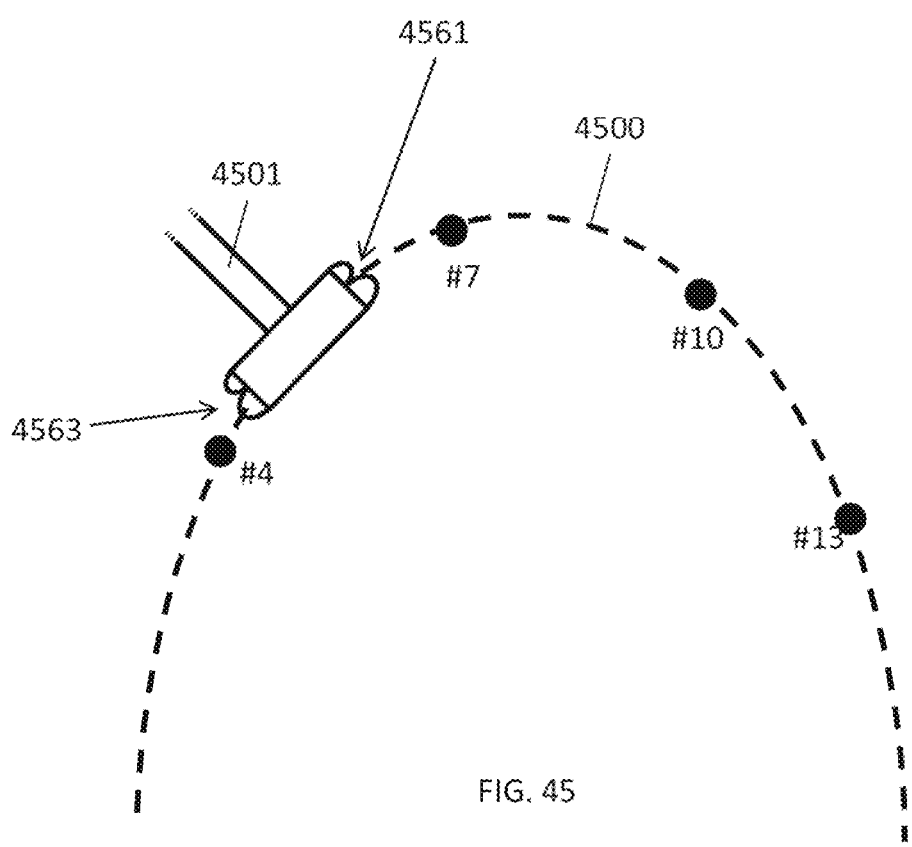
FIG. 45 is a simplified schematic of an IOS collecting measurements whilst positioned between abutments, according to some embodiments of the invention.

In some embodiments, the IOS is positioned between dental features, for example, between abutments e.g. as illustrated in FIG. 45. In some embodiments, the IOS is positioned at a tooth and/or abutment height above gum level In some embodiments, for two FOVs or a compound FOV with two FOV portions, gingiva are captured in both FOV parts or gingiva on one part and at least a portion of an abutment on the other part or one or more portion of an abutment is captured in each part.

At 4302, in some embodiments, depth measurements are collected (e.g. using imaging and pattern projection) from the first FOV and from the second FOV. For example, simultaneously and/or when the IOS is in the same spatial position.

In some embodiments, depth measurements are collected using LED produced light structured image/s (e.g. RGB wavelength light e.g. as described elsewhere in this document).

Alternatively or additionally, in some embodiments, depth measurements are collected using laser produced light. In some embodiments, distances are measured using time for a laser light signal to be reflected from an object being measured. In some embodiments, the distances measured using the laser light are used in addition to structured light depth measurements where the laser reflection time is used as course "range finder" depth measurement, for example, in some embodiments, guiding (e.g. providing a focal distance for structured light measurements). In some embodiments, at least 6 distance measurements are collected between two objects, (e.g. abutments), 6 distance measurements enabling estimation of relative position and/or orientation of the two objects.

In some embodiments, positioning and/or movement of the IOS and/or of IOS FOVs is controlled (e.g. automatically e.g. by one or more actuator) and/or directed (e.g. by indications to a user through a user interface) based on the known implant and/or abutment position/s. In some embodiments, before and/or during automatic movement, the planned and/or current movement is communicated to the user, e.g. through one or more user interface. In some embodiments, control of IOS FOV direction is by movement of one or more actuator which, for example, change a direction of the FOV with respect to a body of the IOS.

In some embodiments, position of one or more implant and/or abutment (e.g. within the dental arch) is known (e.g. before commencement of measurements). For example, from one or more of user input (e.g. a user inputs number references for tooth positions including an abutment) and/or received data e.g. imaging (e.g. previous IOS data, CT, MRI, ultrasound).

For example, in some embodiments, direction and/or angle that the FOVs are directed to (e.g. by movement of the IOS) are selected before and/or during measurements, e.g. based on known implant and/or abutment position. Additionally or alternatively, other data is used to direct the FOVs. For example, other anatomical information than abutment position (e.g. jaw bone and/or teeth position and/or orientation). For example, during scanning based on amount of collected measurement data and/or accuracy of measurement data.

Potentially, directing measurements using known implant and/or abutment position increase scan speed and/or increase ease of scanning for the dental practitioner collecting measurements.

At 4304, in some embodiments, one or more dental abutment is identified (e.g. by a processing unit of the IOS) from the collected measurements collected in step 4302 (e.g. images). In some embodiments, abutment/s are identified as being different objects than gingiva (and/or teeth) e.g. identified from surrounding gingiva. In some embodiments, position and/or orientation of one or more dental abutment is estimated. In some embodiments, identifying abutment/s from measurements includes using or more abutment parameter e.g. one or more of shape, height, color e.g. where one or more abutment parameters is known e.g. received from a database.

At 4306, in some embodiments, distance/s between dental abutments (and/or other dental features) and/or orientation of one or more abutment are estimated (e.g. by a processing unit) using collected IOS measurements. In some embodiments, relative orientation between abutments is estimated.

In some embodiments, dental abutment position (e.g. with respect to other dental object/s e.g. additional abutment/s) estimated in 6 Degrees Of Freedom (6 DOF); measurements on 3 axes for position and/or distance and 3 angles for orientation.

In some embodiments, for one or more abutment pair, distance between the pair and/or relative orientation of the abutments in the pair is estimated.

Additionally or alternatively, estimation of distance/s between and/or orientation of abutment/s is estimated using known IOS parameters. For example, known distances between one or more IOS component e.g. between imager/s and/or projector/s and/or mirror/s and/or prism/s e.g. as identified during calibration of the side FOVs of the IOS is used in the estimation.

Where, in some embodiments, calibration (which, in some embodiments, is performed during manufacture and/or assembly of the IOS e.g. upon connection of the IOS attachment to the IOS) includes calibrating measurements collected from imager/s with FOVs extending at different angles from the IOS (e.g. on different sides of the IOS e.g. as illustrated in FIG. 44A).

In some embodiments, the calibration is performed using parallel planes e.g. including one or more feature as described and/or illustrated regarding FIG. 28 and/or FIGS. 29A-31.

Additionally or alternatively, estimation is using additional data. For example, known position of one or more implant and/or abutment (e.g. within the dental arch). For example, data from one or more of user input (e.g. a user inputs number references for tooth positions including an abutment) and/or received data e.g. imaging (e.g. previous IOS data, CT, MRI, ultrasound).

At 4308, in some embodiments, a mouth model (and/or partial mouth model e.g. a single dental arch) is generated and/or adjusted using calculated distance and/or relative orientation of one or more abutment and/or one or more additional dental object (e.g. another abutment e.g. a tooth).

In some embodiments, during generation and/or adjustment of the model, the abutment/s are first fixed (and, in some embodiments, other rigid mouth structure/s e.g. teeth) within the model. In some embodiments, soft tissue (e.g. gingiva) is then added to the model.

In some embodiments, generating the model includes combining relative position and orientation of dental objects (e.g. the objects including two or more abutments) with model/s of the dental objects. Where the relative position and orientation is, for example, estimated using measurements from an IOS including an attachment (e.g. according to one or more embodiment as described in this document).

In some embodiments, one or more dental object model is generated from IOS (e.g. lacking an attachment) measurements. Where, in some embodiments, the IOS measurements are accurate for short range (e.g. for an abutment, e.g. for 1-3 teeth). But, in some embodiments, are not accurate regarding the relative position and/or orientation of dental objects at larger distances e.g. dental objects at different ends of a dental arch.

Additionally or alternatively, in some embodiments, one or more dental object model is a model of a type of abutment (or other artificial dental object). Where, for example, in some embodiments, for one or more abutment (or other artificial dental object), a model (e.g. from a subset of models) is selected. In some embodiments, the model is based on known abutment dimensions (e.g. from manufacture). In some embodiments, replacing abutment measurements with a model of the abutment increases accuracy of the model.

In some embodiments, a user selects abutment model/s to be used (e.g. through a user interface). In some embodiments, selection of one or more model uses additional data (e.g. as described above regarding step 4306).

In some embodiments, measurements of an abutment are used to identify a type of the abutment (e.g. in order to select a model for use in generating and/or adjusting the mouth model). For example, in some embodiments, using shape and/or size and/or color of the abutment identified from collected image/s, abutment (and/or other artificial dental object model/s) are selected based on collected IOS measurements, e.g. including one or more feature as described regarding step 4302.

A potential advantage of using a model of an abutment (or other dental feature), is the ability to provide a mouth model with full abutments when measurement images of one or more abutment e.g. in a single position of the IOS, capture only a portion of the abutment (or other dental feature).

In some embodiments, estimated position and/or orientation of abutments (e.g. in 6 DOF) are sent to dental design software which, for example, generates and/or adjusts a mouth model. For example Exocad® dental software.

FIGS. 44A-C are schematic illustrations of measurement of an edentulous dental arch 4400 using IOSs configured to produce a compound FOV image, according to some embodiments of the invention.

In some embodiments, one or more dental arch region lacking a tooth includes a dental implant and, optionally, one or more abutment connected (e.g. screwed into) to an implant where, in some embodiments, the abutment is visible in contrast to surrounding gingiva.

In some embodiments, an IOS is selected for a given patient's mouth and/or for a type of mouth e.g. IOS selected based on and/or type based on one or more of; number of missing teeth, mouth size. For example, in some embodiments, an IOS attachment is selected based on the mouth and/or dental arch to be measured.

In some embodiments, FIGS. 44A-E, illustrate a dental arch 4400 including four implants and four abutments; #4, #7, #10 and #13. In some embodiments, dental arch 4400 entirely lacks teeth (e.g. as illustrated in FIGS. 44A-C).

In some embodiments, an attachment is selected so that, when the IOS s positioned within the patient's mouth, more than one abutment is located within IOS attachment FOVs. For example, referring to FIG. 44A in some embodiments, IOS 4401 has two imagers 4405, 4409 and a projector associated with each imager 4403, 4407 respectively (or less imager/s and/or projector and one or more splitter). In some embodiments, more than one abutment is captured in one or more FOV (e.g. when IOS 4401 remains stationary within dental arch 4400). For example, in some embodiments, abutments #4, #7 are captured within a FOV of imager 4409 and projector 4407. For example, in some embodiments, abutments #10, #13 are captured within a FOV of imager 4405 and projector 4403.

In some embodiments, IOS 4401 lacks non-sideways imagers (e.g. referring to FIG. 44A, imager 4401 lacks an imager with FOV directed downwards towards the gingiva and/or upwards). For example, in some embodiments, IOS 116 illustrated in FIG. 9B lacks imager 800-1. For example, in some embodiments, IOS 116 illustrated in FIG. 10 lacks elements 1002,1010.

Referring now to FIG. 44B, in some embodiments, IOS 4411 includes n FOVs. For example, 4 imager FOVs 4415 and 4 associated projector FOVs 4413 (e.g. the IOS including 4 imagers or less than four imagers, where one or more FOV is split e.g. using mirror/s). In some embodiments, the IOS attachment includes at least two FOVs. In some embodiments, an attachment has the same number (or more) of FOVs as there are abutments in the dental arch to be measured. For example, four FOVs for four abutments e.g. as illustrated in FIG. 44B.

Referring now to FIG. 44C, in some embodiments, an IOS 4421 includes at least one curved lens and/or mirror 4423, 4425, where, in some embodiments, one or both of lenses 4423, 4425 are fisheye lenses. For example, in some embodiments an IOS attachment includes one or more curved lens (and/or mirror). Potentially, a FOV reflected by a curved lens (and/or mirror) has a wider FOV, for example so that, in some embodiments, a single imager collects an image including features spaced apart from each other on a dental arch 4400. For example, abutments for non-adjacent teeth. For example, in some embodiments FOV of mirror 4425 collects an image including both abutment #10 and #13.

In some embodiments, the IOS including curved lenses (and/or mirrors) is calibrated (e.g. before collecting measurements), for example, to compensate for distortion introduced into images by the lenses (and/or mirrors), in some embodiments, enabling estimation of true distance/s from collected measurements.

In some embodiments, directions of FOVs of the IOS are selected (e.g. by moving IOS mirror/s and/or imager/s and/or a body of the IOS itself). Where, in some embodiments, selection is based on aiming to maintain the abutment/s and/or other dental features within FOV/s of the IOS.

In some embodiments, directions of FOVs are selected by a user before and/or during scanning. For example, by manually positioning and/or moving the IOS before and/or during collection of measurements. For example, by the user selecting directions (e.g. FOV directions) at a user interface e.g. based on the user's assessment of position of abutment/s and/or other dental features to be measured. In some embodiments, a user selects direction for one or more FOV from a set of predefined directions.

Additionally or alternatively, in some embodiments, selection is automatic. In some embodiments, selection is based on known position of present abutments (and/or dental features). Where, for example, a user inserts numeral indications of present abutment/s and/or teeth. In some embodiments, selection is based, additionally or alternatively on other data, for example imaging data (e.g. CT) e.g. showing position and/or number of abutments.

In some embodiments, selection is based on processor commands, where, in some embodiments, the processor identifies (e.g. from collected measurements) whether a FOV is capturing an abutment (or other dental feature). The processor, in some embodiments, selects one or more FOV direction based on the presence and/or absence of abutment/s within the FOV. In some embodiments, the processor tracks position of one or more abutment e.g. using historical measurement data from the scan and/or movement data. In some embodiments, the processor sends control signals to move one or more FOV (e.g. to one or more actuator) for example, based on selected direction. Alternatively, or additionally, in some embodiments, the processor sends an alert (e.g. to a user through a user interface) to indicate that abutment/s (and/or other dental feature/s) are absent from one or more FOV.

In some embodiments, for example, where measurement is of sets (e.g. pairs) of dental objects (e.g. abutments), for example, as described in step 4300. The processor identifies once enough measurements are collected so that an orientation and position of a set (e.g. pair of abutments) is successfully estimated. In some embodiments, the processor then sends an alert to a user (e.g. to a user through a user interface) to indicate to the user to move the IOS and/or IOS FOVs for collection of more measurements e.g. of additional dental object sets. Alternatively or additionally, in some embodiments, upon identifying successful estimation of orientation and position of a set, the processor generates and/or sends control signals to actuator/s instructing movement of the IOS and/or FOVs of the IOS.

FIG. 45 is a simplified schematic of an IOS 4501 collecting measurements of a dental arch 4500 whilst positioned between abutments #4, #7, according to some embodiments of the invention.

In some embodiments, IOS 4501 is positioned between dental features, for example, between abutments #4, #7. In some embodiments, the IOS is positioned at a tooth and/or abutment height above gum level.

In some embodiments, IOS 4501 includes one or more FOV directed towards (downwards) dental arch 4500 (not illustrated in FIG. 45). In some embodiments, calibration of side imagers 4561, 4563 and the one or more FOV directed in a non-sideways direction (e.g. perpendicular to a direction of the side imagers) is used in measurement of gingiva between the abutments #4, #7 between which the IOS is positioned. For example, to provide a position of the gingiva with respect to abutments #4, #7. Where, in some embodiments, calibration includes using known distance and/or angle between imager/s. In some embodiments, elements 4561, 4563 are imager-projector pair/s.

In some embodiments, position of the IOS within the mouth (e.g. as a user moves the IOS around within the mouth to collect measurements) is estimated (e.g. by a processing unit) using distance measured between the IOS and abutment/s.

Exemplary Enlargement of Baseline

In some embodiments, an IOS attachment is configured to increase a baseline of an IOS to which it is attached. A potential advantage of an enlarged baseline is increased accuracy of IOS measurements of distant objects, for example, when scanning teeth from different regions (e.g. opposite sides, different ends) of a dental arch.

In some embodiments, an attachment includes different mirrors and/or different mirror angle for an imager and a projector where the mirrors are positioned to enlarge the baseline of the imager-projector pair.

Figure 46A:
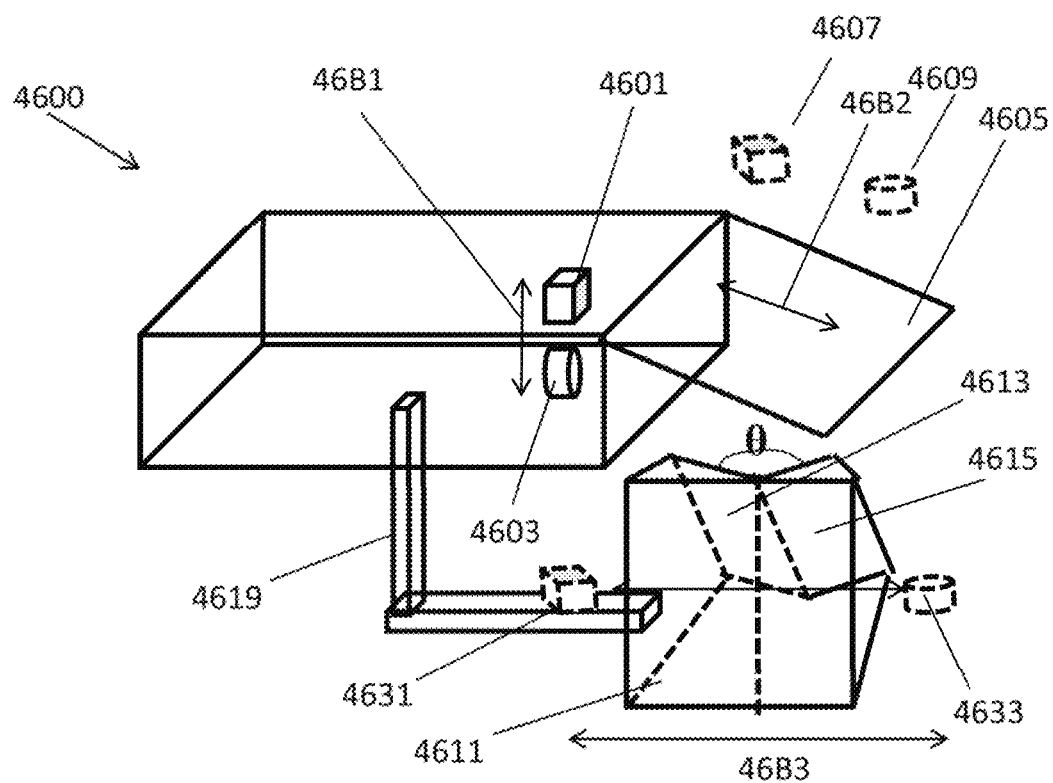
FIGS. 46A-B are a simplified schematic of IOS with attachments that increase the baseband of the IOS, according to some embodiments of the invention.
Figure 46B:
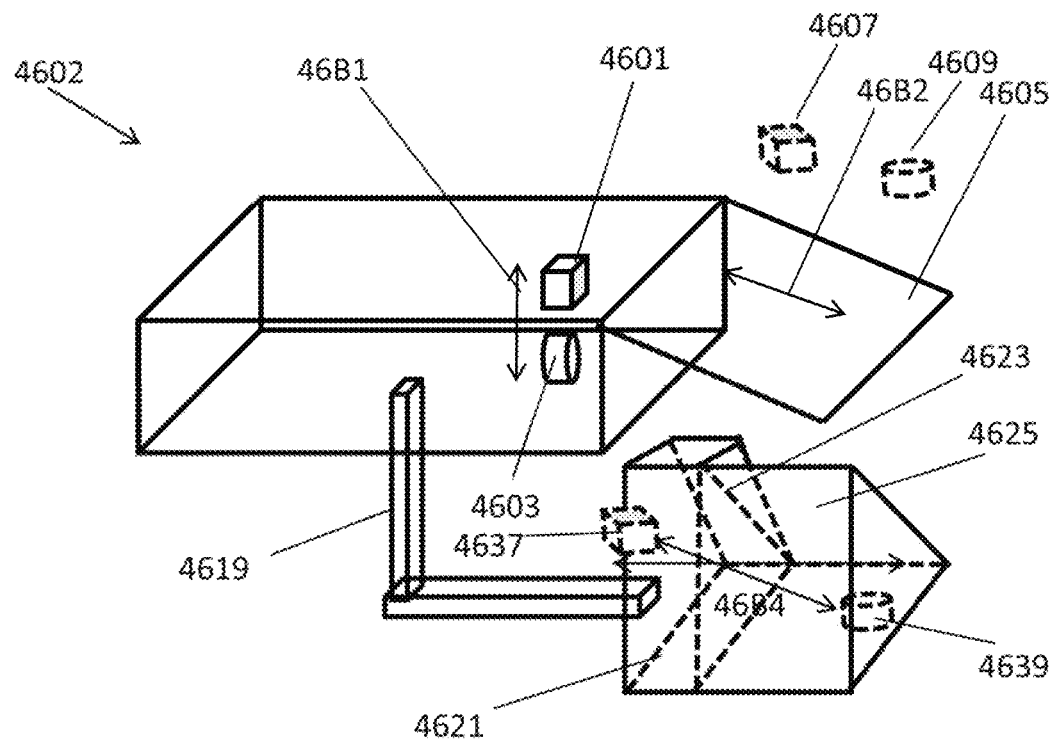

FIGS. 46A-B are a simplified schematic of IOSs 4600, 4602 with attachments that increase the baseline of the IOS, according to some embodiments of the invention. In some embodiments, baseline between an imager and a projector is increased by reflecting the FOVs using different angled reflective surfaces for the imager FOV and the projector FOV.

Referring now to FIG. 46A in some embodiments, IOS 4600 includes an imager 4601 and a projector 4603. In some embodiments, a first surface 4605 (mirror or prism) changes direction of FOVs of imager 4601 and projector 4603 e.g. by about 90°, e.g. from sideways (e.g. center of FOVs parallel with a long axis of imager 4601) to downwards (e.g. center of FOVs perpendicular to a long axis of imager 4601). In some embodiments, reflection at mirror rotates FOVs of imager 4601 and projector 4603 to a position of first virtual imager 4607 and first virtual projector 4609. In some embodiments, rotation of the FOVs does not change a size of the baseline, for example, baseline 46B1 is the same as first virtual baseline 46B2.

In some embodiments, a second surface 4611 which in some embodiments includes a mirror surface and/or more than one mirror surface and/or one or more prism. In some embodiments, second optical component 4611 further rotates the FOVs of the imager and projector moving the imager and projector to a position of a second virtual imager 4631 and a second virtual projector 4633. Where a baseline 46B3 between second virtual imager 4631 and second virtual projector 4633 is larger than that of imager 4601 and projector 4603, 46B3>46B1.

In some embodiments, second optical component 4611 includes an imager surface 4613 and a projector surface 4615. Where, in some embodiments, the imager surface 4613 is positioned to reflect the imager FOV and/or the projector surface 4615 is positioned to reflect the projector FOV. In some embodiments, second optical component 4611 is configured so that an increase in baseline from 46B1 to 46B3 is in a direction of a long axis of the IOS. For example, in some embodiments, an angle, $\theta$, between planes of the imager and projector surfaces is in a plane at an angle (e.g. perpendicular as illustrated in FIG. 46A) to a long axis of the IOS. A potential advantage being that the FOVs converge. In some embodiments, surfaces 4613, 4615 are angled so that the FOVs converge at a distance (and/or range of distances) from the IOS where dental objects (e.g. teeth, gingiva, abutments) are located. For example the distance being 0.5-15 cm, or 1-10 cm or 1-5 cm, or lower or higher or intermediate ranges or distances.

In some embodiments, the imager surface and/or projector surface are planar surfaces. In some embodiments, the imager surface and the projector surface are angled towards each other, for example, with an angle, $\theta$, between the planes of the surfaces of 30-170°, or 90-120°, or lower or higher or intermediate angles or ranges.

In some embodiments second optical component 4611 is connected to the IOS by a connector 4619. In some embodiments, second optical component 4611 is part of an IOS attachment In some embodiments, an IOS attachment includes both first surface 4605 and second optical component 4611.

Referring now to FIG. 46B in some embodiments, IOS 4602 includes one or more feature as described regarding IOS 4600 FIG. 46A where, in some embodiments like elements have like reference numerals.

In some embodiments, a second optical component 4621 of IOS 4602, includes a virtual imager surface 4625 and a virtual projector 4639 surface 4623 configured to increase a baseline of the imager-projector pair 46B1 to 46B4. In some embodiments, surfaces 4625, 4623 are angled so that an increase in baseline is 10 in a direction perpendicular to a long axis of the IOS.

In some embodiments, imager and projector surfaces of a second surface are angled to increase a baseline in both a direction parallel and a direction perpendicular to a long axis of the IOS.

In some embodiments, the second optical component (e.g. 4611 and/or 4621) includes non-planar surfaces, for example one or more curved reflector (e.g. mirror).

In some embodiments, the second surface is also a FOV splitter, where, for example, in some embodiments, the second surface includes four surfaces, a first imager surface, a second imager surface, a first projector surface and a second projector surface. Where each imager-projector pair includes one or more feature as described regarding surfaces 4613, 4615 FIG. 46A and/or surfaces 4623, 4625 FIG. 46B. In some embodiments, the first imager surface and first projector surface are angled to direct a portion of the FOVs of the imager and projector in a first direction at an angle to a long axis of the projector and the second imager surface and second projector surface are angled to direct a portion of the FOVs of the imager in a second direction at an angle to the long axis of the projector.

Figure 47A:
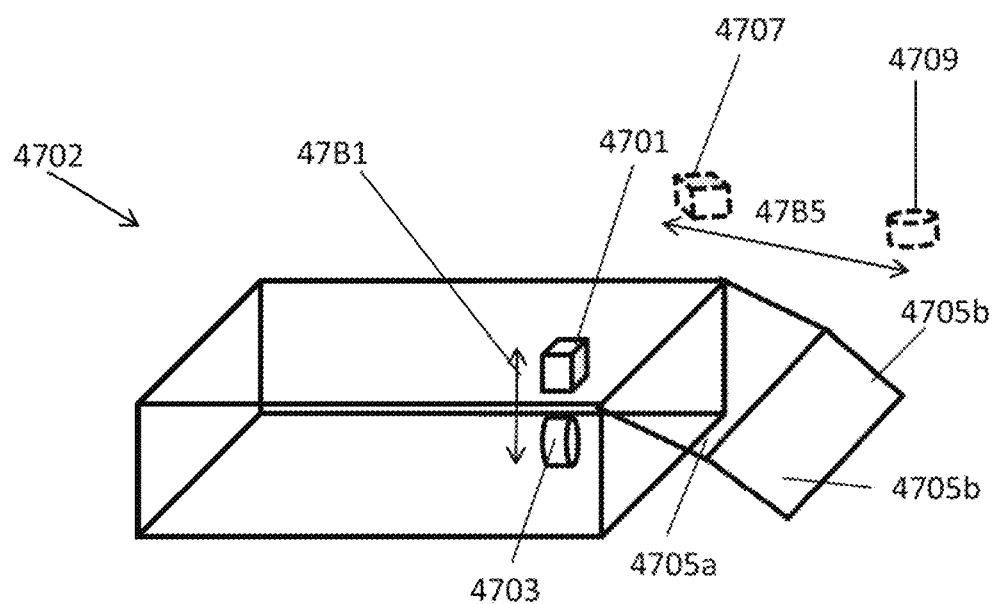
FIGS. 47A-B are a simplified schematic of an IOS with attachments that increase the baseline of the IOS, according to some embodiments of the invention
Figure 47B:
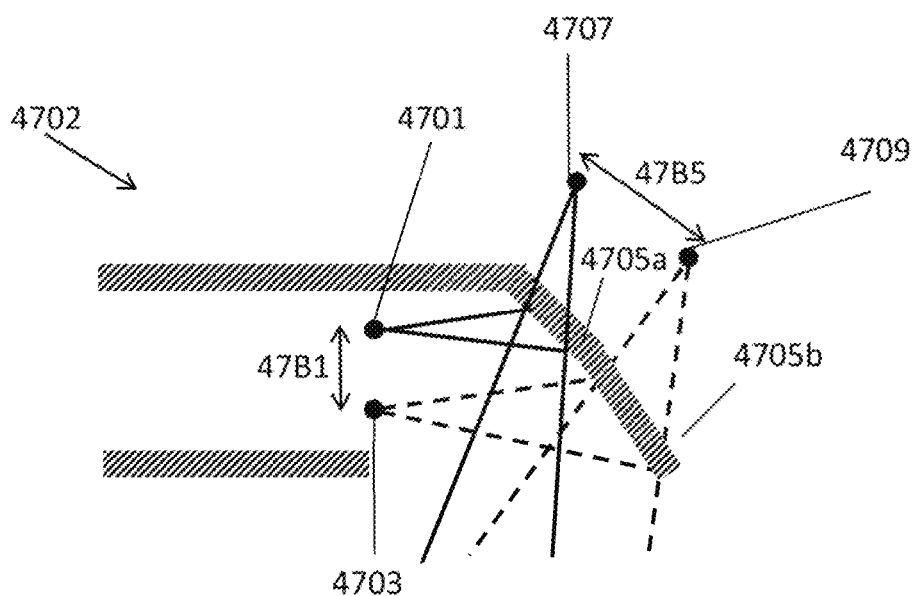

FIGS. 47A-B are a simplified schematic of an IOS 4702 with attachments that increase the baseline of the IOS, according to some embodiments of the invention. In some embodiments, IOS 4702 includes an imager 4701 and a projector 4703.

In some embodiments, FIG. 47B shows a side view of the IOS of FIG. 47A and further illustrates FOVs of imager 4701 (solid line) and projector 4703 (dashed line).

In some embodiments, an IOS baseline 47B1 between the imager 4701 and the projector 4703 is increased by a single reflection. Where, in some embodiments, IOS 4702 has a single reflection. For example, in some embodiments, a first surface 4705 includes at least two different mirror surfaces at different angles 4705*a*, 4705*b*. Which increase the baseline from 47B1 to a baseline 47B5 between a virtual imager 4707 and a virtual projector 4709. In some embodiments, a multi-angle first mirror surface is used with the embodiments, of FIG. 27B and/or FIG. 27C.

Alternatively, in some embodiments, an IOS increases baseline at more than one reflection, for example, in some embodiments, an IOS includes mirrors 4705*a*, 4705*b* and an additional reflective surface which increases baseline e.g. surfaces 4613, 4615 FIG. 46A, e.g. surface 4623, 4625 FIG. 46B.

Exemplary Attachment Including Lenses

In some embodiments, an IOS attachment (e.g. one or more attachment and/or mount as described elsewhere within this document) includes one or more element to change a focal distance of the IOS (e.g. focal distance of one or more FOV of the IOS e.g. FOV of one or more projector and/or FOV of one or more imager and/or FOVs of one or more projector—imager pair). In some embodiments, the focal distance adjusting element/s include one or more lens.

Potentially, the ability to change a focal distance of an IOS enables an IOS configured to measure short differences to collect longer distance measurements with higher resolution. Potentially, the ability to change a focal distance of an IOS enables an IOS configured to measure long differences to collect short distance measurements with higher resolution.

Where, in some embodiments, "short distance" is defined as where the focus is 1-20 mm, or 5-20 mm or 5-10 mm, or lower or higher or intermediate ranges or distances. Where, in some embodiments, "long distance" is defined as where the focus is 20-50 mm, or 20-30 mm, or lower or higher or intermediate ranges or distances.

In some embodiments, an attachment is configured to change a IOS (e.g. including a FOV with a focal distance) to an a-focal system. For example, using one or more lens. In some embodiments, an a-focal IOS (e.g. an IOS to which an a-focal attachment is connected). In some embodiments, one or more lens is used to maintain the focal distance of one or more FOV of the IOS whilst changing an extent of the FOV. For example, increasing an extent of an FOV to capture a larger portion of the dental scene (e.g. larger portion of a dental arch) with the same IOS. For example, decreasing an extent of an FOV to capture a larger portion of the dental scene (e.g. smaller portion of a dental arch) with the same IOS.

Exemplary Correcting of a Composite Image

Figure 40:
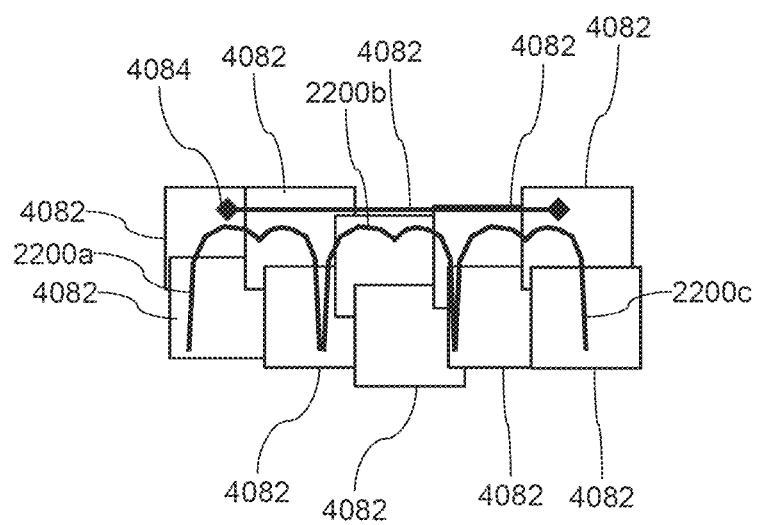
FIG. 40 is a schematic view illustrating correcting a composite model using a large scale measurement in accordance with an embodiment of the current disclosure.

FIG. 40 is a schematic view illustrating correcting a composite model using a large scale measurement in accordance with an embodiment of the current disclosure. In some embodiments, a composite model of a dental object (for example a few teeth 2200*a*-2200*c*) is produced by stitching together a set of small scale models 4082.

In some embodiments, a composite model includes small scale models where one or more small scale model is from a different angle. For example, where, in some embodiments, small scale models include side and/or top view/s of one or more dental feature (e.g. tooth, abutment).

Optionally, the composite model may include a composite image, a composite depth mapped image and/or a full 3D composite model. Optionally, one or more of the small scale models 4082 may include an image, a depth mapped image and/or a 3D model. In some embodiments, stitching together small scale models 4082 creates an additive error over a long distance (covering a few small stitched together zones).

Optionally the locations of features in the model are corrected based on a large scale measurement 4084. For example, measurement 4084 may be derived from a large scale image and/or a compound image that includes features in distant locations. For example, the 3D model may be conditioned on one or more large scale measurements 4084. In some embodiments, a large scale measurement is collected by an IOS using imager/s at different location/s within the IOS. For example, referring to FIG. 32C, in some embodiments, IOS 3201 includes an additional imager located at a distance from imagers 3203, 3205, e.g. located next to projector 3221.

Figure 41:
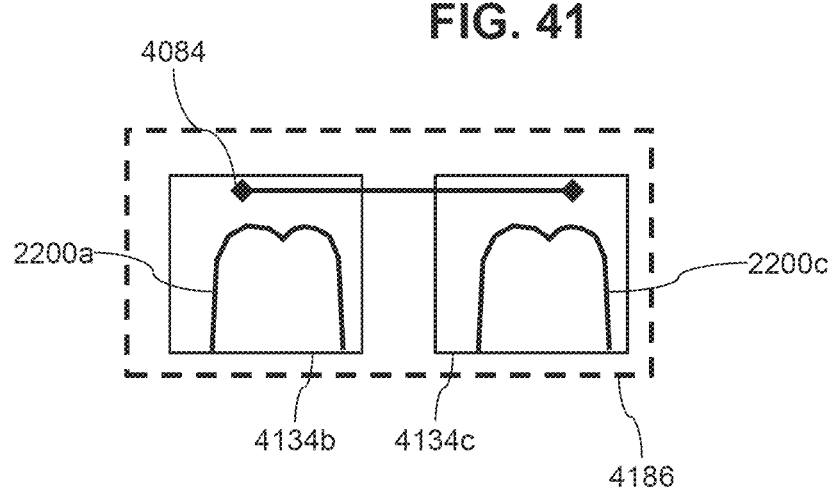
FIG. 41 is a schematic illustration of a compound image including a calibration area in accordance with an embodiment of the current disclosure.

FIG. 41 is a schematic illustration of a compound image in accordance with an embodiment of the current disclosure. For example, a compound image 4186 may include a plurality of subfields, for example subfields 4134*b* and 4134*c*. For example, subfield 4134*b* may include tooth 2200*a* and subfield 4134*c* may include tooth 2200*c*.

Optionally the two subfields 4134*b*, 4134*c* are non-continuous. For example, the compound image 4186 may not include the area between the teeth 2200*a*, 2200*c*. For example, the compound image 4186 does not include tooth 2200*b* which is located between teeth 2200*a* and 2200*c*. Optionally, the relative locations of objects between subfields 4134*b* and 4134*c* is known and/or can be computed. For example, from the compound image 4186, a distance 4084 between a feature on tooth 2200*a* and 2200*c* is calculated. For example, this distance 4084 may be used to correct a composite model, for example as described herein above with respect to FIG. 40 and/or FIGS. 22-25.

Figure 42:
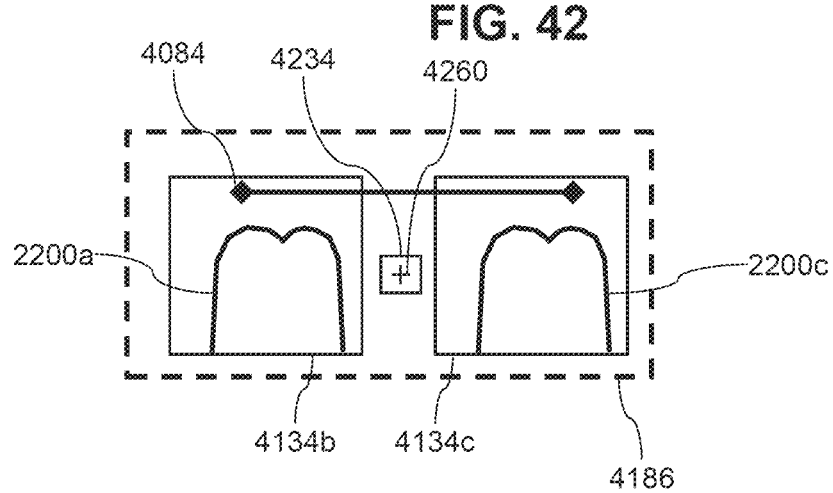
FIG. 42 is a schematic illustration of a compound image including a calibration area in accordance with an embodiment of the current disclosure.

FIG. 42 is a schematic illustration of a compound image including a calibration area in accordance with an embodiment of the current disclosure. Optionally, a compound image 4186 includes a subfield 4234 that includes an image of a calibration area 4234. For example, the calibration area 4234 may include a fiduciary marker 4260 and/or a diffuse reflection of a projected pattern and/or a specular reflection of a fiduciary object (for example as explained in FIGS. 28-31. In some embodiments, there are more than one subfields that include an image of a calibration. Optionally, the plurality of subfields hold images of different targets in different places that may facilitate the calibration process and/or generate a more accurate calibration.

General

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub combination or as suitable in any other described embodiment of the disclosure. Certain features described in the context of various embodiments are not to be considered essential features of those embodiments, unless the embodiment is inoperative without those elements.

Although the disclosure has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. Moreover, some embodiments of the present disclosure are distinguishable from the prior art for specifically lacking one and/or another feature present in the prior art. Thus, claims to some embodiments of the disclosure can include negative limitations.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting.

What is claimed is:

1. An intraoral scanner (IOS) comprising:
   a plurality of imagers;
   a plurality of pattern projectors, wherein each of the plurality of pattern projectors is configured to:
   project a pattern of structured light, and
   include a baseline length from each of said plurality of imagers;
   and
   a processor configured to:
   determine a working distance of a region of interest (ROI) from said intraoral scanner (IOS) using one or more images acquired by one or more of said plurality of imagers,
   select a baseline length separating a pattern projector of said plurality of projectors and an imager of said plurality of imagers, at a given time, based on said working distance, and
   automatically select said pattern projector and said imager for illumination and imaging the region of interest (ROI).

2. The intraoral scanner (IOS) of claim 1, wherein a field of view (FOV) of said imager overlaps a field of view (FOV) of said first projector at a first working distance from said imager and a field of view (FOV) of said imager overlaps a FOV of said second projector at a second working distance greater than said first working distance.

3. The intraoral scanner (IOS) as in claim 2, wherein a first field of view (FOV) of said overlapping field of views (FOVs) of a first pattern projector of said plurality of pattern projectors, which includes a shorter baseline with said at least one imager of said plurality of imagers, is optimized for a first working distance shorter than a second working distance of a second field of view (FOV) of said overlapping field of views (FOVs) of a second pattern projector of said plurality of pattern projectors, which includes a longer baseline with said at least one imager of the plurality of imagers, wherein said first pattern projector and said second pattern projector each project a properly focused image at said first working distance and said second working distance respectively.

4. The intraoral scanner (IOS) as in claim 1, further comprising a probe and including at least two imagers of the plurality of imagers each of which includes with a given readout time per frame (1/frames per second (FPS)), wherein:
   each of said at least two imagers is configured to be read at a different time, such that a time difference is less than said readout time, and
   a depth obtained from each of said at least two imagers is used for locating said probe at a frequency which is larger than said frames per second (FPS).

5. The intraoral scanner (IOS) as in claim 4, wherein said (IOS) is configured to:
   acquire an image of a first region of interest (ROI) in an oral cavity using a first imager of the plurality of imagers, and said first imager includes a first frame period, and
   acquire a second image of a feature in said oral cavity using a second imager of the plurality of imagers, wherein a second image is acquired within a time lag of more than $1/100$th of said frame period and less than said $3/4$ of said frame period.

6. The intraoral scanner (IOS) as in claim 1, wherein said plurality of imagers comprises:
   a first imager configured to obtain a first image of a first region of interest (ROI) of at least a portion of a dental arch, and
   a second imager configured to obtain a second image of a second region of interest (ROI) of the dental arch, wherein the first region of interest (ROI) and the second region of interest (ROI) do not overlap.

7. The intraoral scanner (IOS) as in claim 6, wherein said processor is configured to:
   reconstruct depth information for said first image and said second image; and
   generate a single model of said portion of said dental arch by using said depth information.

8. The intraoral scanner (IOS) as in claim 6, wherein said selection of a baseline length is according to said representative distance and comprises moving one or both of said two optical modules.

9. The intraoral scanner (IOS) as in claim 6, wherein said selection of a baseline length is according to said representative distance and comprises selecting a longer baseline length as said representative distance increases.

10. The intraoral scanner (IOS) as in claim 6, wherein said first imager and said second imager are configured to image said first region of interest (ROI) and said second region of interest (ROI) simultaneously.

11. The intraoral scanner (IOS) as in claim 6, wherein said first imager and said second imager are configured to image said first region of interest (ROI) and said second region of interest (ROI) within a time period of less than a frame rate of an imager.

12. The intraoral scanner (IOS) as in claim 1, wherein said intraoral scanner (IOS) includes a splitter which splits a field of view (FOV) of at least one imager of the plurality of imagers into a first field of view (FOV) and a second field of view (FOV).

13. The intraoral scanner (IOS) as in claim 12, wherein said splitter comprises one or more mirrors, and at least one of the mirrors increases at least one baseline.

14. The intraoral scanner (IOS) as in claim 12, wherein said splitter comprises one or more lenses, and at least one of the lenses changes at least one focus of at least one image or one projector.

15. The intraoral scanner (IOS) as in claim 12, wherein said splitter is part of an attachment connected to said intraoral scanner (IOS).

16. The intraoral scanner (IOS) as in claim 1, wherein said processor is further configured to:
    acquire a plurality of small scale images;
    stitch together said plurality of small scale images to form a large scale 3D model; acquire with said IOS a correction image including two disconnected small scale images and two features distanced by a scale greater than a maximum breadth of any of said plurality of small images;
    determine a relative position of said two features from said correction image; and
    adjust a position of a feature in said large scale 3D model based on said relative position.

17. The intraoral scanner (IOS) as in claim 16, wherein said correction image is configured for calibration based on a calibration subfield.

18. The intraoral scanner (IOS) as in claim 1, wherein:
    the plurality of imagers include a given readout time per frame (1/frames per second (FPS)), and
    each of said plurality of imagers is configured to be read at a different time, such that a time difference is less than said readout time and a depth obtained from each of said at least two imagers is used for locating said IOS at a frequency which is larger than said frames per second (FPS).

19. The intraoral scanner (IOS) according to claim 1, wherein:
    said first and second pattern projectors are configured to project respective first and second patterns onto a region of interest (ROI), said first and second patterns illuminating respective first and second portions of the regions of interest (ROI); and
    said processor is configured to acquire and process first and second images imaged by said imager to determine which of said first and second portions is larger, and to automatically select a pattern projector corresponding to the larger of said first and second portions.

20. The intraoral scanner (IOS) of claim 1, wherein said plurality of pattern projectors comprise:
    a first pattern projector distances from an imager of said plurality of imagers by a first baseline length; and
    a second pattern projector distanced from said imager of said plurality of imagers by a second baseline length greater than said first baseline length, wherein said second pattern projector is configured to operate at a larger focus distance than said first pattern projector.

* * * * *